(12) United States Patent
Fischer et al.

(10) Patent No.: US 7,087,616 B2
(45) Date of Patent: Aug. 8, 2006

(54) PYRAZOLYL PYRIMIDINES

(75) Inventors: Rüdiger Fischer, Pulheim (DE); Bernd Alig, Königswinter (DE); Thomas Bretschneider, Lohmar (DE); Mazen Es-Sayed, Langenfeld (DE); Christoph Erdelen, Leichlingen (DE); Peter Lösel, Leverkusen (DE); Udo Reckmann, Köln (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/468,371

(22) PCT Filed: Feb. 11, 2002

(86) PCT No.: PCT/EP02/01400

§ 371 (c)(1),
(2), (4) Date: Dec. 11, 2003

(87) PCT Pub. No.: WO02/068413

PCT Pub. Date: Sep. 6, 2002

(65) Prior Publication Data

US 2004/0102465 A1    May 27, 2004

(30) Foreign Application Priority Data

Feb. 22, 2001    (DE) .................. 101 08 480

(51) Int. Cl.
*C07D 403/04*    (2006.01)
*A01N 43/54*    (2006.01)
(52) U.S. Cl. .................. 514/274; 514/275; 544/317; 544/323; 544/324; 544/328
(58) Field of Classification Search ........ 544/317, 544/323, 324, 328; 514/274, 275
See application file for complete search history.

(56) References Cited

FOREIGN PATENT DOCUMENTS

| EP | 165 448 | 12/1985 |
|---|---|---|
| EP | 967 212 | 12/1999 |
| WO | 94/29268 | 12/1994 |

OTHER PUBLICATIONS

Bondavalli et al., CAPLUS Abstract 118:139216, 1993.*
Aust. J. Chem., 33, (month unavailable) 1980, pp. 2291-2298, Desmond J. Brown, William B. Cowden, Geoffrey W. Grigg and Diana Kavulak, "Unfused Heterobicycles as Amplifiers of Phleomycin. I Some Pyridinyl- and Pyrazolylpyrimidines, Bithiazoles and Thiazolylpyridines".
Chem. Ind., 37, (month unavailable) 1985, pp. 730-732, Harry R. Ungerer, "Schiffsfarben —eine Spezialität der seenahen Lackindustrie".
**Chemical Abstracts, vol. 55, No. 21, 1961, Columbus, Ohio, US; abstract No. 21137c KH Feldman: "2- or 6 Substituted Pyrimidines." Seite 21137; Spalte 1; XP002202312 Zusammenfassung & Zhur. Obshchei Khim. Bd. 30, 1960, Seiten 3835-9, USSSR.

* cited by examiner

*Primary Examiner*—Deepak Rao
(74) *Attorney, Agent, or Firm*—Richard E. L. Henderson

(57) ABSTRACT

This invention relates to novel pyrazolylpyrimidines of the formula

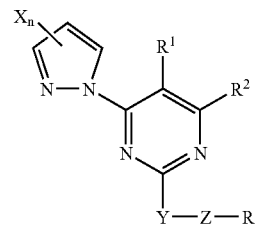

in which $R^1$, $R^2$, X, n, Y, Z and R have the meanings given in the disclosure, to a plurality of processes for preparing these substances, and to their use for controlling pests.

43 Claims, No Drawings

PYRAZOLYL PYRIMIDINES

The present invention relates to novel pyrazolylpyrimidines to a plurality of processes for their preparation and to their use as pesticides.

Specific pyrazolylpyrimidines have already been described in connection with the synthesis of activity enhancers for the tumour static phleomycin (cf. Aust. J. Chem. 1980, 33, 2291–2298). However, the only compound mentioned explicitly, 2-{[4-(3,5-dimethyl-1H-pyrazol-1-yl)-2-pyrimidinyl]thio}acetamide, had no enhancing effect on phleomycin.

Insecticidally active pyrazolylpyrimidines have hitherto not been disclosed.

This invention now provides substituted pyrazolylpyrimidines of the formula (I)

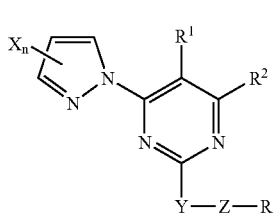

in which $R^1$ and $R^2$ independently of one another represent hydrogen, halogen, nitro, cyano, alkyl, halogenoalkyl, alkoxy, halogenoalkoxy, alkenyl, alkinyl, alkenyloxy, halogenoalkenyloxy, alkinyloxy, halogenoalkinyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl;

or represent aryl, arylalkyl, saturated or unsaturated heterocyclyl having 1 to 4 heteroatoms from the group consisting of nitrogen, oxygen and sulphur, each of which radicals is optionally substituted by substituents from the group consisting of halogen, alkyl, halogenoalkyl, alkoxy and halogenoalkoxy, $R^1$ and $R^2$ furthermore together represent alkylene or alkenylene, where the carbon chain may be interrupted by 1 to 3 heteroatoms from the group consisting of nitrogen and oxygen and where the ring formed in this manner for its part may optionally be substituted by halogen or alkyl, X represents halogen, nitro, cyano, hydroxyl, alkyl, halogenoalkyl, alkoxy, halogenoalkoxy, alkenyl, alkinyl, alkenyloxy, halogenoalkenyloxy, alkinyloxy, halogenoalkinyloxy, —S(O)$_p$R$^3$, —SO$_2$NR$^4$R$^5$, —NR$^4$R$^5$, —COR$^6$, —CO$_2$R$^7$, —CSR$^6$, —CONR$^4$R$^5$, —NHCO$_2$R$^8$, cycloalkyl;

or represents aryl, arylalkyl, saturated or unsaturated heterocyclyl having 1 to 4 heteroatoms from the group consisting of nitrogen, oxygen and sulphur, each of which radicals is optionally substituted by substituents from the group consisting of halogen, alkyl, halogenoalkyl, alkoxy and halogenoalkoxy;

or, if n represents 2 or 3, two adjacent radicals X furthermore together represent alkylene or alkenylene, where the carbon chain may be interrupted by 1 or 2 heteroatoms from the group consisting of nitrogen and oxygen, n represents 0, 1, 2 or 3, where X represents identical or different radicals if n represents 2 or 3, Y represents a direct bond, oxygen, —S(O)$_p$— or —NR$^9$—, p represents 0, 1 or 2, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$— or —(CH$_2$)$_r$—C(R$^{12}$)=C(R$^{13}$)—(CH$_2$)$_w$—, r represents 1, 2, 3, 4, 5 or 6, t and w independently of one another represent 0, 1, 2, 3 or 4, R represents the grouping

or represents a carboxylic acid bioisostere (acid mimic), in particular from the group consisting of

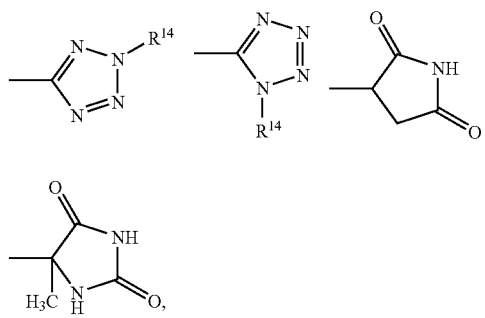

A represents oxygen, sulphur or NR$^{15}$,

E represents —OR$^{16}$, —SR$^{16}$, —O$^-$M, —S$^-$M or —NR$^{17}$R$^{18}$,

M represents ammonium which is optionally mono- to tetrasubstituted by identical or different radicals from the group consisting of alkyl, aryl and arylalkyl, or represents an alkali metal ion, M furthermore represents an alkaline earth metal ion, where in each case two molecules of a compound form a salt with such an ion, $R^3$ represents hydrogen, alkyl, halogenoalkyl, cycloalkyl, cycloalkylalkyl;

or represents aryl, arylalkyl, saturated or unsaturated heterocyclyl or heterocyclylalkyl having 1 to 4 heteroatoms from the group consisting of nitrogen, oxygen and sulphur, each of which radicals is optionally substituted by substituents from the group consisting of halogen, alkyl, halogenoalkyl, alkoxy, halogenoalkoxy, alkylthio and halogenoalkylthio, $R^4$ represents hydrogen, alkyl, halogenoalkyl, cycloalkyl or alkylcarbonyl, $R^5$ represents hydrogen, amino, formyl, alkyl, alkenyl, alkinyl, halogenoalkyl, cycloalkyl, alkoxy, alkoxyalkyl, alkylcarbonyl, alkoxycarbonyl, oxamoyl, $R^4$ and $R^5$ furthermore together represent alkylidene; or represent optionally halogen-, nitro-, alkyl-, halogenoalkyl-substituted benzylidene;

$R^4$ and $R^5$ furthermore together with the nitrogen atom to which they are attached form a saturated or unsaturated heterocycle which may optionally contain a further nitrogen, oxygen or sulphur atom and which may optionally be substituted by alkyl, $R^6$ represents hydrogen, alkyl, halogenoalkyl or arylalkyl, $R^7$ represents hydrogen, alkyl, halogenoalkyl, cycloalkyl, cycloalkylalkyl, aryl or arylalkyl, $R^8$ represents alkyl or halogenoalkyl, $R^9$ represents hydrogen, alkyl, halogenoalkyl, cycloalkyl, cycloalkylalkyl;

or represents aryl, arylalkyl, saturated or unsaturated heterocyclyl or heterocyclylalkyl having 1 to 4 heteroatoms from the group consisting of nitrogen, oxygen and sulphur, each of which radicals is optionally substituted by substituents from the group consisting of halogen, alkyl, halogenoalkyl, alkoxy, halogenoalkoxy, alkylthio and halogenoalkylthio, $R^{10}$ represents halogen, alkyl, alkylcarbonyl, alkoxycarbonyl, cycloalkyl, cycloalkylalkyl;

or represents aryl or arylalkyl which for their part may be substituted in the aryl moiety by halogen or alkyl, $R^{11}$ represents hydrogen or alkyl, $R^{12}$ and $R^{13}$ independently of one another represent hydrogen, hydroxyl, alkyl or alkoxy, $R^{14}$ represents hydrogen, alkyl or halogenoalkyl, $R^{15}$ represents hydrogen, alkyl, alkoxy, cyano or dialkylamino, $R^{16}$ represents hydrogen or represents $-NR^4R^5$;

represents alkyl, alkenyl, alkinyl, each of which radicals is optionally substituted by substituents from the group consisting of halogen, amino, hydroxyl, cyano, nitro, alkoxy, halogenoalkoxy, alkylthio, halogenoalkylthio, alkoxycarbonyl, alkenyloxycarbonyl, alkylcarbonyloxy, oxyalkyleneoxy, aryloxy, halogenoaryloxy, $-CONR^4R^5$, $-NR^4R^5$, $-ONR^4R^5$ and $-C(R^{14})=N-OR^{14}$ substituted;

or represents aryl, arylalkyl, cycloalkyl, cycloalkylalkyl, saturated or unsaturated heterocyclyl or heterocyclylalkyl having 1 to 4 heteroatoms from the group consisting of nitrogen, oxygen and sulphur, each of which radicals is optionally substituted by substituents from the group consisting of halogen, alkyl, halogenoalkyl, alkoxy, halogenoalkoxy, alkylthio, halogenoalkylthio, alkoxycarbonyl and alkylcarbonyloxy, $R^{17}$ represents hydrogen or alkyl, $R^{18}$ represents hydrogen, hydroxyl, amino, $-SO_2R^8$, alkyl, alkenyl;

or represents cycloalkyl, cycloalkylalkyl, aryl, arylalkyl, heteroaryl or heteroarylalkyl having 1 to 4 heteroatoms from the group consisting of nitrogen, oxygen and sulphur, each of which radicals is optionally substituted by substituents from the group consisting of halogen, hydroxyl, alkyl, halogenoalkyl, alkoxy, halogenoalkoxy, alkylthio, halogenoalkylthio and oxyalkyleneoxy, $R^{17}$ and $R^{18}$ furthermore together with the nitrogen atom to which they are attached represent a 5- or 6-membered saturated or unsaturated heterocycle which may contain 1 or 2 further heteroatoms from the group consisting of nitrogen, oxygen and sulphur and which may optionally be substituted by alkyl, except for the compound 2-{[4-(3,5-dimethyl-1H-pyrazol-1-yl)-2-pyrimidinyl]thio}acetamide.

Depending on the type and number of substituents, the compounds of the formula (I) may, if appropriate, be present as geometrical and/or optical isomers or regioisomers or isomer mixtures thereof of varying compositions. What is claimed by the invention are both the pure isomers and the isomer mixtures. Furthermore, compounds of the formula (I) can, if appropriate, be present in various tautomeric forms, depending on the type and number of substituents. What is claimed by the invention are all tautomers.

The invention also claims all salts of compounds of the formula (I), for example with mineral acids such as hydrochloric acid.

Furthermore, it has been found that pyrazolylpyrimidines of the formula (I-a)

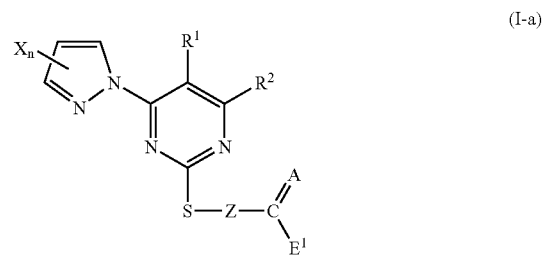

(I-a)

in which $R^1$, $R^2$, X, n, Z and A have the meanings given above and $E^1$ represents $-OR^{16}$, $-SR^{16}$ or $NR^{17}R^{18}$, are obtained by reacting halogenopyrimidines of the formula (II)

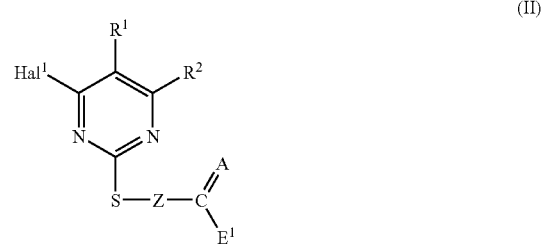

(II)

in which $R^1$, $R^2$, Z, A and $E^1$ have the meanings given above and $Hal^1$ represents halogen, with pyrazole compounds of the formula (III)

(III)

in which

X and n have the meanings given above

A) in the presence of a base and, if appropriate, in the presence of a diluent, or B) under the action of microwaves, if appropriate in the presence of a base and if appropriate in the presence of a diluent, or C) in the presence of a catalyst, if appropriate in the presence of a base and if appropriate in the presence of a diluent, or D) pyrazolylpyrimidines of the formula (I-b)

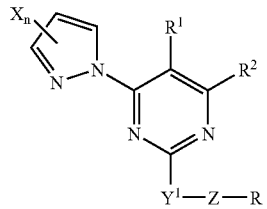
(I-b)

in which
R¹, R², X, n, Z and R have the meanings given above and
Y¹ represents —SO— or —SO²—,
are obtained by oxidizing
pyrazolylpyrimidines of the formula (I-c)

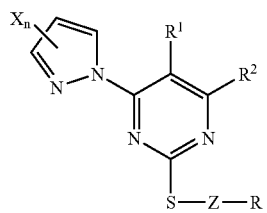
(I-c)

in which
R¹, R², X, n, Z and R have the meanings given above,
with an oxidizing agent, if appropriate in the presence of a diluent, if appropriate in the presence of an acid binder and if appropriate in the presence of a catalyst, or E) pyrazolylpyrimidines of the formula (I-d)

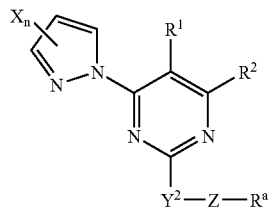
(I-d)

in which
Y² represents oxygen or —NR⁹—,
Rᵃ represents one of the groupings below

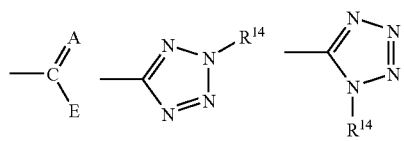

R¹, R², X, n, Z, R⁹ and R¹⁴ have the meanings given above,
are obtained by reacting
halogenopyrimidines of the formula (IV)

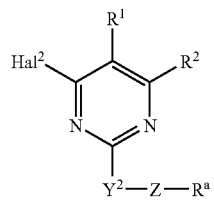
(IV)

in which
R¹, R² Y², Z and Rᵃ have the meanings given above,
Hal² represents halogen,
with pyrazole compounds of the formula (III)

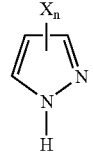
(III)

in which
X and n have the meanings given above,
if appropriate in the presence of a base, if appropriate in the presence of a diluent and if appropriate in the presence of a catalyst, or F) pyrazolylpyrimidines of the formula (I-e)

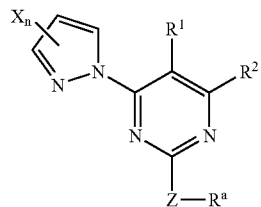
(I-e)

in which
R¹, R², X, n, Z and Rᵃ have the meanings given above,
are obtained by reacting
pyrazolylpyrimidine halides of the formula (V)

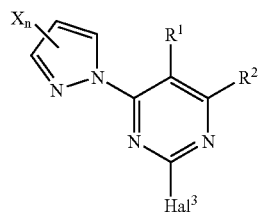
(V)

in which
R¹, R², X and n have the meanings given above,
Hal³ represents halogen, F1) either with organometallic compounds of the formula (VI)

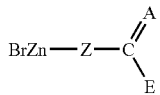
(VI)

in which
Z, A and E have the meanings given above,
if appropriate in the presence of a base, if appropriate in the presence of a diluent and if appropriate in the presence of a catalyst, or F2) in a first step with organometallic compounds of the formula (VI)

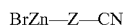
(VII)

in which
Z has the meanings given above,
if appropriate in the presence of a base, if appropriate in the presence of a diluent and if appropriate in the presence of a catalyst,
and reacting the resulting nitrites of the formula (VIII)

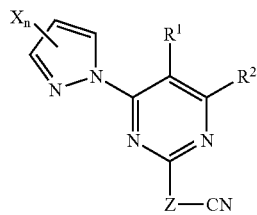
(VIII)

in which
R¹, R², X, n and Z have the meanings given above,
with trialkyltin azides, if appropriate in the presence of a diluent, or G) pyrazolylpyrimidines of the formula (I-f)

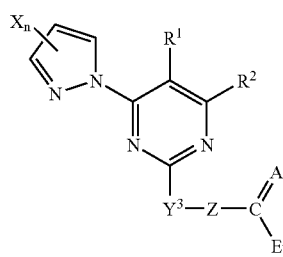
(I-f)

in which
Y³ represents a direct bond, oxygen, sulphur or —NR⁹—,
E² represents —O⁻M or —S⁻M and
R¹, R², X, n, Z, A, M and R⁹ have the meanings given above,
are obtained by reacting pyrazolylpyrimidines of the formula (I-g)

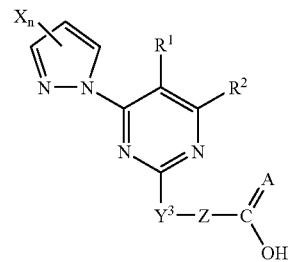
(I-g)

in which
R³, R², X, n, Y³, Z and A have the meanings given above,
with hydroxides of the formula (IX)

(IX)

in which
M has the meanings given above,
if appropriate in the presence of a diluent, or H) pyrazolylpyrimidines of the formula (I-h)

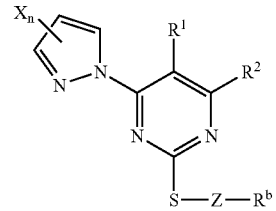
(I-h)

in which
Rᵇ represents one of the groupings below

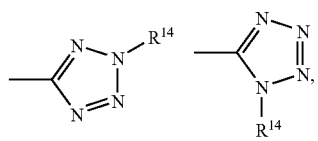

R¹, R², X, n, Z and R¹⁴ have the meanings given above,
are obtained by reacting
nitrites of the formula (X)

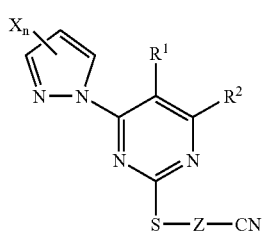
(X)

in which
R¹, R², X, n and Z have the meanings given above, with trialkyltin azides, if appropriate in the presence of a diluent, or J) pyrazolylpyrimidines of the formula (I-j)

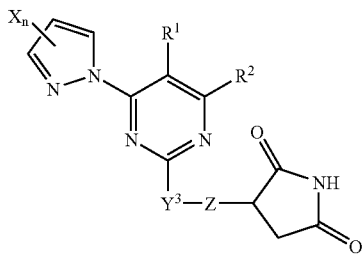

(I-j)

in which
$R^1$, $R^2$, X, n, $Y^3$ and Z have the meanings given above,
are obtained by hydrogenating
pyrazolylpyrimidines of the formula (I-k)

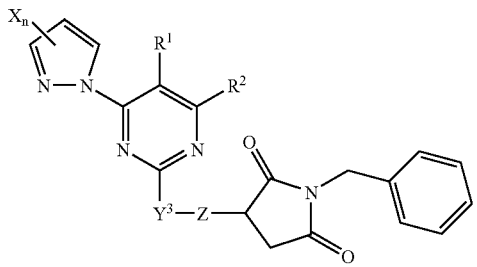

(I-k)

in which
$R^1$, $R^2$, X, n, $Y^3$ and Z have the meanings given above,
if appropriate in the presence of a diluent and in the presence of a catalyst, or K) pyrazolylpyrimidines of the formula (I-l)

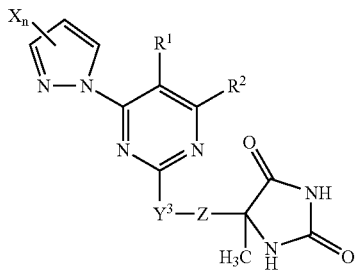

(I-l)

in which
$R^1$, $R^2$, X, n, $Y^3$ and Z have the meanings given above,
are obtained by reacting keto compounds of the formula (XI)

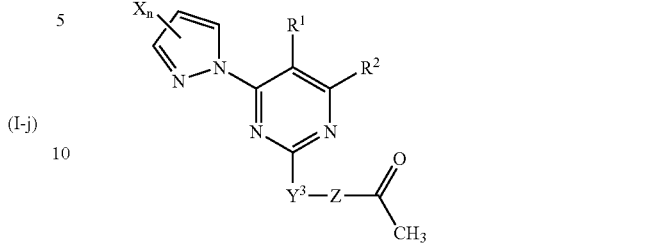

(XI)

in which
$R^1$, $R^2$, X, n, $Y^3$ and Z have the meanings given above,
with ammonium carbonate and potassium cyanide, if appropriate in the presence of a diluent.

Finally, it has been found that the compounds of the formula (I) according to the invention have very good insecticidal properties and can be used both in crop protection and in the protection of materials for controlling undesirable pests such as insects. Hitherto, nothing has been disclosed in the prior art about any insecticidal activity of pyrazolylpyrimidines.

The formula (I) provides a general definition of the pyrazolylpyrimidines according to the invention.

$R^1$ and $R^2$ independently of one another preferably represent hydrogen, halogen, nitro, cyano, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkinyl, $C_2$–$C_6$-alkenyloxy, $C_2$–$C_6$-halogenoalkenyloxy, $C_2$–$C_6$-alkinyloxy, $C_2$–$C_6$-halogenoalkinyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, $C_3$–$C_7$-cycloalkyl;

or represent aryl, aryl-$C_1$–$C_6$-alkyl or 5- or 6-membered saturated or unsaturated heterocyclyl having 1 to 4 heteroatoms, which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$–$C_6$-alkyl, $C_1$–$C_6$-halogenoalkyl, $C_1$–$C_6$-alkoxy and $C_1$–$C_6$-halogenoalkoxy;

$R^1$ and $R^2$ furthermore together preferably represent $C_3$–$C_5$-alkylene or $C_3$–$C_4$-alkenylene, where the carbon chain may be interrupted by 1 or 2 heteroatoms, which may be 0 to 2 nitrogen atoms and/or 0 or 1 oxygen atom, and where the ring formed in this manner for its part may optionally be mono- or polysubstituted by identical or different substituents from the group consisting of halogen and $C_1$–$C_6$-alkyl;

X preferably represents halogen, nitro, cyano, hydroxyl, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkinyl, $C_2$–$C_6$-alkenyloxy, $C_2$–$C_6$-halogenoalkenyloxy, $C_2$–$C_6$-alkinyloxy, $C_2$–$C_6$-halogenoalkinyloxy, —S(O)$_p$R$^3$, —SO$_2$NR$^4$R$^5$, —NR$^4$R$^5$, —COR$^6$, —CO$_2$R$^7$, —CSR$^6$, —CONR$^4$R$^5$, —NHCO$_2$R$^8$, $C_3$–$C_7$-cycloalkyl;

or represents aryl, aryl-$C_1$–$C_6$-alkyl, 5- or 6-membered saturated or unsaturated heterocyclyl having 1 to 4 heteroatoms, which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$–$C_6$-alkyl, $C_1$–$C_6$-halogenoalkyl, $C_1$–$C_6$-alkoxy and $C_1$–$C_6$-halogenoalkoxy;

or, if n represents 2 or 3, two adjacent radicals X furthermore together preferably represent $C_3$–$C_5$-alkylene or $C_3$–$C_4$-alkenylene, where the carbon chain may be interrupted by 1 or 2 heteroatoms, which may be 0 to 2 nitrogen atoms and/or 0 or 1 oxygen atom;

n preferably represents 0, 1, 2 or 3, where X represents identical or different radicals if n represents 2 or 3;

Y preferably represents a direct bond, oxygen, —S(O)$_p$— or —NR$^9$—;

p preferably represents 0, 1 or 2;

Z preferably represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$— or —(CH$_2$)$_t$—C(R$^{12}$)=C(R$^{13}$)—(CH$_2$)$_w$—, r preferably represents 1, 2, 3, 4, 5 or 6;

t and w independently of one another preferably represent 0, 1, 2, 3 or 4;

R preferably represents the grouping

or represents a carboxylic acid bioisostere (acid mimic), in particular from the group consisting of

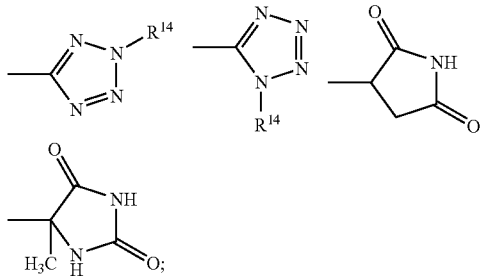

A preferably represents oxygen, sulphur or NR$^{15}$;

E preferably represents —OR$^{16}$, —SR$^{16}$, —O$^-$M, —S$^-$M or —NR$^{17}$R$^{18}$;

M preferably represents ammonium which is optionally mono- to tetrasubstituted by identical or different substituents from the group consisting of $C_1$–$C_6$-alkyl, aryl and aryl-$C_1$–$C_6$-alkyl, or represents a lithium cation (Li$^+$), a sodium cation (Na$^+$) or a potassium cation (K$^+$);

M furthermore preferably represents a magnesium cation (Mg$^{2+}$) or a calcium cation (Ca$^{2+}$), where in each case two molecules of a compound form a salt with such an ion;

R$^3$ preferably represents hydrogen, $C_1$–$C_6$-alkyl, $C_1$–$C_6$-halogenoalkyl, $C_3$–$C_7$-cycloalkyl, $C_3$–$C_7$-cycloalkyl-$C_1$–$C_6$-alkyl;

or represents aryl, aryl-$C_1$–$C_6$-alkyl, 5- or 6-membered saturated or unsaturated heterocyclyl or heterocyclyl-$C_1$–$C_6$-alkyl having 1 to 4 heteroatoms, which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio;

R$^4$ preferably represents hydrogen, $C_1$–$C_6$-alkyl, $C_1$–$C_6$-halogenoalkyl, $C_3$–$C_7$-cycloalkyl, $C_1$–$C_6$-alkylcarbonyl;

R$^5$ preferably represents hydrogen, amino, formyl, $C_1$–$C_6$-alkyl, $C_2$–$C_6$-alkenyl, $C_2$–$C_6$-alkinyl, $C_1$–$C_6$-halogenoalkyl, $C_3$–$C_7$-cycloalkyl, $C_1$–$C_6$-alkoxy, $C_1$–$C_6$-alkoxy-$C_1$–$C_6$-alkyl, $C_1$–$C_6$-alkylcarbonyl, $C_1$–$C_6$-alkoxycarbonyl, oxamoyl;

R$^4$ and R$^5$ furthermore together preferably represent $C_1$–$C_6$-alkyldene; or represent benzylidene which is optionally mono- or polysubstituted by identical or different substituents from the group consisting of halogen, nitro, $C_1$–$C_6$-alkyl and $C_1$–$C_6$-halogenoalkyl;

R$^4$ and R$^5$ furthermore together with the nitrogen atom to which they are attached preferably represent a 5- or 6-membered saturated or unsaturated heterocycle which may optionally contain a further nitrogen, oxygen or sulphur atom and which may optionally be mono- or polysubstituted by identical or different $C_1$–$C_6$-alkyl;

R$^6$ preferably represents hydrogen, $C_1$–$C_6$-alkyl, $C_1$–$C_6$-halogenoalkyl or aryl-$C_1$–$C_6$-alkyl;

R$^7$ preferably represents hydrogen, $C_1$–$C_6$-alkyl, $C_1$–$C_6$-halogenoalkyl, $C_3$–$C_7$-cycloalkyl, $C_3$–$C_7$-cycloalkyl-$C_1$–$C_6$-alkyl, aryl or aryl-$C_1$–$C_6$-alkyl;

R$^8$ preferably represents $C_1$–$C_6$-alkyl or $C_1$–$C_6$-halogenoalkyl;

R$^9$ preferably represents hydrogen, $C_1$–$C_6$-alkyl, $C_1$–$C_6$-halogenoalkyl, $C_3$–$C_7$-cycloalkyl, $C_3$–$C_7$-cycloalkyl-$C_1$–$C_6$-alkyl;

or represents aryl, aryl-$C_1$–$C_6$-alkyl, 5- or 6-membered saturated or unsaturated heterocyclyl or heterocyclyl-$C_1$–$C_6$-alkyl having in each case 1 to 4 heteroatoms, which contain 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio;

R$^{10}$ preferably represents halogen, $C_1$–$C_6$-alkyl, $C_1$–$C_6$-alkylcarbony, $C_1$–$C_6$-alkoxycarbonyl, $C_3$–$C_7$-cycloalkyl, $C_3$–$C_7$-cycloalkyl-$C_1$–$C_6$-alkyl;

or represents aryl or aryl-$C_1$–$C_6$-alkyl, which for their part may be mono- or polysubstituted in the aryl moiety by identical or different substituents from the group consisting of halogen and $C_1$–$C_6$-alkyl;

R$^{11}$ preferably represents hydrogen or $C_1$–$C_6$-alkyl;

R$^{12}$ and R$^{13}$ independently of one another preferably represent hydrogen, hydroxyl, $C_1$–$C_6$-alkyl or $C_1$–$C_6$-alkoxy;

R$^{14}$ preferably represents hydrogen, $C_1$–$C_6$-alkyl or $C_1$–$C_6$-halogenoalkyl, R$^{15}$ preferably represents hydrogen, $C_1$–$C_6$-alkyl, $C_1$–$C_6$-alkoxy, cyano or di($C_1$–$C_6$-alkyl)amino;

R$^{16}$ preferably represents hydrogen or preferably represents —NR$^4$R$^5$; represents $C_1$–$C_{16}$-halogenoalkyl, $C_2$–$C_{16}$-halogenoalkenyl, $C_2$–$C_{10}$-halogenoalkinyl;

represents $C_1$–$C_{16}$-alkyl, $C_2$–$C_{10}$-alkenyl, $C_2$–$C_6$-alkinyl, each of which is optionally mono- or polysubstituted by identical or different substituents from the group consisting of amino, hydroxyl, cyano, nitro, $C_1$–$C_6$-alkoxy, $C_1$–$C_6$-halogenoalkoxy, $C_1$–$C_6$-alkylthio, $C_1$–$C_6$-halogenoalkylthio, $C_1$–$C_6$-alkoxycarbonyl, $C_2$–$C_6$-alkenyloxycarbonyl, $C_1$–$C_6$-alkylcarbonyloxy, oxy($C_1$–$C_6$-alkylene)oxy, aryloxy, halogenoaryloxy, —CONR$^4$R$^5$, —NR$^4$R$^5$, —ONR$^4$R$^5$ and —C(R$^{14}$)=N—OR$^{14}$;

or represents aryl, aryl-$C_1$–$C_6$-alkyl, $C_3$–$C_7$-cycloalkyl, $C_3$–$C_7$-cycloalkyl-$C_1$–$C_6$-alkyl, 4- to 6-membered saturated or unsaturated heterocyclyl or heterocyclyl-$C_1$–$C_6$-alkyl having in each case 1 to 4 heteroatoms, which contain 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, $C_1$–$C_6$-halogenoalkylthio, $C_1$–$C_6$-alkoxycarbonyl and $C_1$–$C_6$-alkylcarbonyloxy;

$R^{17}$ preferably represents hydrogen or $C_1$–$C_6$-alkyl;

$R^{18}$ preferably represents hydrogen, hydroxyl, amino, —$SO_2R^8$, $C_1$–$C_6$-alkyl, $C_2$–$C_6$-alkenyl;

or represents $C_3$–$C_7$-cycloalkyl, $C_3$–$C_7$-cycloalkyl-$C_1$–$C_6$-alkyl, aryl, aryl-$C_1$–$C_6$-alkyl, heteroaryl or heteroaryl-$C_1$–$C_6$-alkyl having in each case 1 to 4 heteroatoms, which contain 0 to 4 nitrogen atoms, 0 to 2 nonadjacent oxygen atoms and/or 0 to 2 nonadjacent sulphur atoms, each of which radicals is optionally mono- or polysubstituted by identical or different radicals from the group consisting of halogen, hydroxyl, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio, $C_1$–$C_6$-halogenoalkylthio and oxy($C_1$–$C_6$-alkylene)oxy;

$R^{17}$ and $R^{18}$ furthermore together with the nitrogen atom to which they are attached preferably represent a 5- or 6-membered saturated or unsaturated heterocycle which may contain 1 or 2 further heteroatoms, which may be 0 to 2 nitrogen atoms, 0 or 1 oxygen atom and/or 0 or 1 sulphur atom and which may optionally be mono- or polysubstituted by identical or different $C_1$–$C_6$-alkyl;

except for the compound 2-{[4-(3,5-dimethyl-1H-pyrazol-1-yl)-2-pyrimidinyl]thio}acetamide.

$R^1$ and $R^2$ independently of one another particularly preferably represent hydrogen, fluorine, chlorine, bromine, nitro, cyano, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms, $C_2$–$C_4$-alkenyly, $C_2$–$C_4$-alkynyl, —$S(O)_pR^3$, —$NR^4R^5$, —$COR^6$, —$CO_2R^7$, —$CSR^6$, —$CONR^4R^5$, —$NHCO_2R^8$, $C_3$–$C_6$-cycloalkyl;

or represent aryl (in particular phenyl), aryl-$C_1$–$C_4$-alkyl, 5- or 6-membered saturated or unsaturated heterocyclyl having 1 to 3 heteroatoms, which contains 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy and $C_1$–$C_4$-halogenoalkoxy having 1 to 9 fluorine, chlorine and/or bromine atoms;

$R^1$ and $R^2$ furthermore together particularly preferably represent -$C_3$–$C_5$-alkylene or $C_3$–$C_4$-alkenylene, where the carbon chain may be interrupted by 1 or 2 heteroatoms, which may be 0 to 2 nitrogen atoms and/or 0 or 1 oxygen atom, and where the ring formed in this manner for its part may optionally be mono- to tetrasubstituted by identical or different substituents from the group consisting of fluorine, chlorine, bromine and $C_1$–$C_4$-alkyl;

X particularly preferably represents fluorine, chlorine, bromine, nitro, cyano, hydroxyl, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms, $C_2$–$C_4$-alkenyl, $C_2$–$C_4$-alkinyl, —$S(O)_pR^3$, —$SO_2NR^4R^5$, —$NR^4R^5$, —$COR^6$, —$CO_2R^7$, —$CSR^6$, —$CONR^4R^5$, —$NHCO_2R^8$, $C_3$–$C_6$-cycloalkyl;

or represents aryl (in particular phenyl), aryl-$C_1$–$C_4$-alkyl, 5- or 6-membered saturated or unsaturated heterocyclyl having 1 to 3 heteroatoms, which contains 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy and $C_1$–$C_4$-halogenoalkoxy having 1 to 9 fluorine, chlorine and/or bromine atoms;

or, if n represents 2 or 3, two adjacent radicals X furthermore together particularly preferably represent $C_3$–$C_4$-alkylene or $C_3$–$C_4$-alkenylene, where the carbon chain may be interrupted by 1 or 2 heteroatoms, which may be 0 to 2 nitrogen atoms, and/or 0 or 1 oxygen atom;

X furthermore particularly preferably represents iodine;

n particularly preferably represents 0, 1, 2 or 3, where X represents identical or different radicals if n represents 2 or 3;

Y particularly preferably represents a direct bond, oxygen, —$S(O)_p$— or —$NR^9$—;

p particularly preferably represents 0, 1 or 2;

Z particularly preferably represents —$(CH_2)_r$—, —$(CH_2)_t$—$(CHR^{10})$—$(CH_2)_w$—, —$(CH_2)_r$—$C(O)$—$(CH_2)_t$—, —$(CH_2)_r$—$O$—$(CH_2)_t$—, —$(CH_2)_r$—$S(O)_p$—$(CH_2)_t$—, —$(CH_2)_r$—$N(R^{11})$—$(CH_2)_t$— or —$(CH_2)_t$—$C(R^{12})$=$C(R^{13})$—$(CH_2)_w$—, r particularly preferably represents 1, 2, 3 or 4;

t and w independently of one another particularly preferably represent 0, 1, 2, 3 or 4;

R particularly preferably represents the grouping

or particularly preferably represents a carboxylic acid bioisostere (acid mimic), in particular from the group consisting of

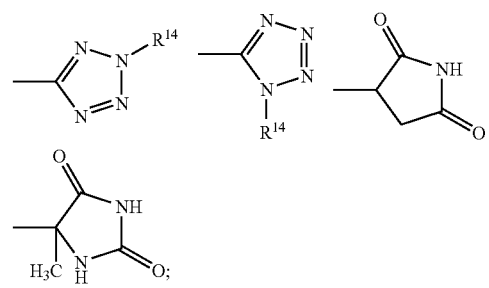

A particularly preferably represents oxygen or sulphur;

E particularly preferably represents —$OR^{16}$, —$SR^{16}$, —$O^-M$, —$S^-M$ or —$NR^{17}R^{18}$;

M particularly preferably represents ammonium which is optionally mono- to tetrasubstituted by identical or different substituents from the group consisting of $C_1$–$C_4$-alkyl, phenyl, benzyl and phenylethyl, or represents a sodium cation ($Na^+$) or a potassium cation ($K^+$);

M furthermore particularly preferably represents a magnesium cation ($Mg^{2+}$) or a calcium cation ($Ca^{2+}$), where in each case two molecules of a compound form a salt with such an ion;

$R^3$ particularly preferably represents hydrogen, $C_1$–$C_4$-alkyl, $C_1$–$C_4$-halogenoalkyl having 1 to 9 fluorine, chlorine and/or bromine atoms, $C_3$–$C_6$-cycloalkyl, $C_3$–$C_6$-cycloalkyl-$C_1$–$C_4$-alkyl;

or represents aryl (in particular phenyl), aryl-$C_1$–$C_4$-alkyl, 5- or 6-membered saturated or unsaturated heterocyclyl or heterocyclyl-$C_1$–$C_4$-alkyl having 1 to 3 heteroatoms, which contains 0 to 3 nitrogen atoms, 0 to 2 nonadjacent oxygen atoms and/or 0 to 2 nonadjacent sulphur atoms, each of which radicals is optionally mono- to tetrasubstituted by identical or different radicals from the group consisting of fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms, $C_1$–$C_4$-alkylthio and $C_1$–$C_4$-halogenoalkylthio having 1 to 9 fluorine, chlorine and/or bromine atoms;

$R^4$ particularly preferably represents hydrogen, $C_1$–$C_4$-alkyl, $C_1$–$C_4$-halogenoalkyl having 1 to 9 fluorine, chlorine and/or bromine atoms, $C_3$–$C_6$-cycloalkyl, $C_1$–$C_4$-alkylcarbonyl;

$R^5$ particularly preferably represents hydrogen, amino, formyl, $C_1$–$C_4$-alkyl, $C_2$–$C_4$-alkenyl, $C_2$–$C_4$-alkinyl, $C_1$–$C_4$-halogenoalkyl having 1 to 9 fluorine, chlorine and/or bromine atoms, $C_3$–$C_6$-cycloalkyl, $C_1$–$C_4$-alkoxy, $C_1$–$C_4$-alkoxy-$C_1$–$C_4$-alkyl, $C_1$–$C_4$-alkylcarbonyl, $C_1$–$C_4$-alkoxycarbonyl, oxamoyl;

$R^4$ and $R^5$ furthermore together particularly preferable represent $C_1$–$C_4$-alkylidene; or represent benzylidene which is optionally mono- to tetrasubstituted by identical or different substituents from the group consisting of fluorine, chlorine, bromine, nitro, $C_1$–$C_4$-alkyl and $C_1$–$C_4$-halogenoalkyl having 1 to 9 fluorine, chlorine and/or bromine atoms;

$R^4$ and $R^5$ furthermore together with the nitrogen atom to which they are attached particularly preferably represent a 5- or 6-membered saturated or unsaturated heterocycle which may optionally contain a further nitrogen, oxygen or sulphur atom and which may optionally be mono- to tetrasubstituted by identical or different $C_1$–$C_4$-alkyl;

$R^6$ particularly preferably represents hydrogen, $C_1$–$C_4$-alkyl, $C_1$–$C_4$-halogenoalkyl having 1 to 9 fluorine, chlorine and/or bromine atoms or aryl-$C_1$–$C_4$-alkyl;

$R^7$ particularly preferably represents hydrogen, $C_1$–$C_4$-alkyl, $C_1$–$C_4$-halogenoalkyl having 1 to 9 fluorine, chlorine and/or bromine atoms, $C_3$–$C_6$-cycloalkyl, $C_3$–$C_6$-cycloalkyl-$C_1$–$C_4$-alkyl, aryl (in particular phenyl) or aryl-$C_1$–$C_4$-alkyl;

$R^8$ particularly preferably represents $C_1$–$C_4$-alkyl or $C_1$–$C_4$-halogenoalkyl having 1 to 9 fluorine, chlorine and/or bromine atoms;

$R^9$ particularly preferably represents hydrogen, $C_1$–$C_4$-alkyl, $C_1$–$C_4$-halogenoalkyl having 1 to 9 fluorine, chlorine and/or bromine atoms, $C_3$–$C_6$-cycloalkyl, $C_3$–$C_6$-cycloalkyl-$C_1$–$C_4$-alkyl;

or represents aryl (in particular phenyl), aryl-$C_1$–$C_4$-alkyl, 5- or 6-membered saturated or unsaturated heterocyclyl or heterocyclyl-$C_1$–$C_4$-alkyl having in each case 1 to 3 heteroatoms, which contain 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms, $C_1$–$C_4$-alkylthio, $C_1$–$C_4$-halogenoalkylthio having 1 to 9 fluorine, chlorine and/or bromine atoms;

$R^{10}$ particularly preferably represents fluorine, chlorine, bromine, iodine, $C_1$–$C_4$-alkyl, $C_1$–$C_4$-alkylcarbonyl, $C_1$–$C_4$-alkoxycarbonyl, $C_3$–$C_6$-cycloalkyl, $C_3$–$C_6$-cycloalkyl-$C_1$–$C_4$-alkyl;

or represents aryl (in particular phenyl) or aryl-$C_1$–$C_4$-alkyl, which for their part may be mono- to tetrasubstituted in the aryl moiety by identical or different substituents from the group consisting of fluorine, chlorine, bromine and $C_1$–$C_4$-alkyl;

$R^{11}$ particularly preferably represents hydrogen or $C_1$–$C_4$-alkyl;

$R^{12}$ and $R^{13}$ independently of one another particularly preferably represent hydrogen, hydroxyl, $C_1$–$C_4$-alkyl or $C_1$–$C_4$-alkoxy;

$R^{14}$ particularly preferably represents hydrogen, $C_1$–$C_4$-alkyl or $C_1$–$C_4$-halogenoalkyl having 1 to 9 fluorine, chorine and/or bromine atoms;

$R^{16}$ particularly preferably represents hydrogen;

represents $C_1$–$C_{16}$-halogenoalkyl having 1 to 31 fluorine, chlorine and/or bromine atoms, $C_2$–$C_{12}$-halogenoalkenyl having 1 to 21 fluorine, chlorine and/or bromine atoms, $C_2$–$C_6$-halogenoalkinyl having 1 to 11 fluorine, chlorine and/or bromine atoms;

represents $C_1$–$C_6$-alkyl, decyl, dodecyl, tetradecyl, hexadecyl, $C_2$–$C_6$-alkenyl, decenyl, $C_2$–$C_4$-alkinyl, each of which is optionally mono- to tetrasubstituted by identical or different substituents from the group consisting of amino, hydroxyl, cyano, nitro, $C_1$–$C_4$-alkoxy, $C_1$–$C_4$-halogenoalkoxy having 1 to 9 fluorine, chlorine and/or bromine atoms, $C_1$–$C_4$-alkylthio, $C_1$–$C_4$-halogenoalkylthio having 1 to 9 fluorine, chlorine and/or bromine atoms, $C_1$–$C_4$-alkoxycarbonyl, $C_2$–$C_4$-alkenyloxycarbonyl, $C_1$–$C_4$-alkylcarbonyloxy, oxy($C_1$–$C_4$-alkylene)oxy, aryloxy, halogenoaryloxy, —$CONR^4R^5$, —$NR^4R^5$, —$ONR^4R^5$ and —$C(R^{14})$=N—$OR^{14}$;

or represents aryl (in particular phenyl), aryl-$C_1$–$C_4$-alkyl, $C_3$–$C_6$-cycloalkyl, $C_3$–$C_6$-cycloalkyl-$C_1$–$C_4$-alkyl, 4- to 6-membered saturated or unsaturated heterocyclyl or heterocyclyl-$C_1$–$C_4$-alkyl having in each case 1 to 3 heteroatoms, which contain 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms, $C_1$–$C_4$-alkylthio, $C_1$–$C_4$-halogenoalkylthio having 1 to 9 fluorine, chlorine and/or bromine atoms, $C_1$–$C_4$-alkoxycarbonyl and $C_1$–$C_4$-alkylcarbonyloxy;

$R^{17}$ particularly preferably represents hydrogen or $C_1$–$C_4$-alkyl;

$R^{18}$ particularly preferably represents hydrogen, hydroxyl, amino, —$SO_2R^8$, $C_1$–$C_4$-alkyl, $C_2$–$C_4$-alkenyl;

or represents $C_3$–$C_6$-cycloalkyl, $C_3$–$C_6$-cycloalkyl-$C_1$–$C_4$-alkyl, aryl (in particular phenyl), aryl-$C_1$–$C_4$- alkyl, heteroaryl or heteroaryl-$C_1$–$C_4$-alkyl having in each case 1 to 3 heteroatoms, which contain 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, hydroxyl, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms, $C_1$–$C_4$-alkylthio, $C_1$–$C_4$-halogenoalkylthio having 1 to 9 fluorine, chlorine and/or bromine atoms and oxy($C_1$–$C_4$-alkylene)oxy;

$R^{17}$ and $R^{18}$ furthermore together with the nitrogen atom to which they are attached particularly preferably represent a 5- or 6-membered saturated or unsaturated heterocycle which may contain 1 or 2 further heteroatoms, which may be 0 to 2 nitrogen atoms, 0 or 1 oxygen atom and/or 0 or 1 sulphur atom, and which may optionally be mono- to trisubstituted by identical or different $C_1$–$C_4$-alkyl;

except for the compound 2-{[4-(3,5-dimethyl-1H-pyrazol-1-yl)-2-pyrimidinyl]thio}acetamide.

$R^1$ and $R^2$ independently of one another very particularly preferably represent hydrogen, fluorine, chlorine, bromine, nitro, cyano, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, methoxy, ethoxy, n-propoxy, isopropoxy, n-butoxy, isobutoxy, sec-butoxy, tert-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCF_2$, —$SOCF_3$, —COMe, —$CO_2Me$, —$CO_2Et$, amino, cyclopentyl, cyclohexyl;

or represent phenyl, benzyl, pyridinyl or furyl, each of which is optionally mono- to trisubstituted by identical or different substituents from the group consisting of fluorine, chlorine, bromine, methyl, ethyl, methoxy, ethoxy, trifluoromethyl and trifluoromethoxy;

$R^1$ and $R^2$ furthermore together very particularly preferably represent propylene, butylene, propenylene, butadienylene, —$(CH_2)_2$—O—$CH_2$—, —$(CH_2)_2$—NH—$CH_2$—, —CH=CH—N=CH— or —CH=CCl—CH=CH—;

X very particularly preferably represents fluorine, chlorine, bromine, nitro, cyano, hydroxyl, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, methoxy, ethoxy, n-propoxy, isopropoxy, n-butoxy, isobutoxy, sec-butoxy, tert-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, vinyl, ethenyl, —$SO^2NH_2$, —$SO_2NHMe$, —$SO_2NMe_2$, amino, —NHMe, —$NMe_2$, —CHO, —COMe, —$CO_2Me$, —$CO_2Et$, —$CONH_2$, —CONHMe, —$CONMe_2$, —NHCOMe, cyclopentyl, cyclohexyl;

or represents phenyl, benzyl, furyl, thienyl, pyrrolyl, oxazolyl, isoxazyl, imidazyl, pyrazyl, thiazolyl, pyridyl, pyrimidinyl, pyridazyl, triazinyl, triazyl, each of which is optionally mono- to trisubstituted by identical or different substituents from the group consisting of fluorine, chlorine, bromine, methyl, ethyl, methoxy, ethoxy, trifluoromethyl and trifluoromethoxy;

or, if n represents 2 or 3, two adjacent radicals X furthermore together very particularly preferably represent propylene, butylene, propenylene, butadienylene, —$(CH_2)_2$—O—$CH_2$—, —$(CH_2)_2$—NH—$CH_2$— or —CH=CH—N=CH—;

X furthermore very particularly preferably represents iodine;

n very particularly preferably represents 0, 1, 2 or 3, where X represents identical or different radicals if n represents 2 or 3;

Y very particularly preferably represents a direct bond, oxygen, —S(O)$_p$— or —$NR^9$—;

p very particularly preferably represents 0, 1 or 2;

Z very particularly preferably represents —$CH_2$—, —$(CH_2)_2$—, —$(CH_2)_3$—, —$(CH_2)_4$—, —$(CHR^{10})$—, —$CH_2$—C(O)—$CH_2$—, —$CH_2$—NH—, —CH=CH—, —$CH_2$—CH=CH—, —CH=C(OH)—, —CH=C(OMe)—, —$CH_2$—C(OMe)=CH—;

R very particularly preferably represents the grouping

or represents a carboxylic acid bioisostere (acid mimic), in particular from the group consisting of

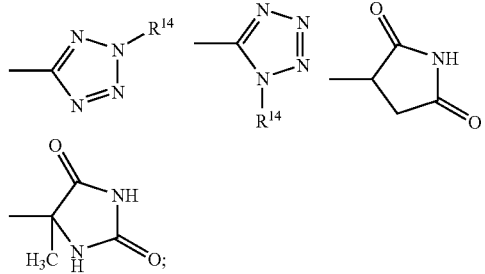

A very particularly preferably represents oxygen or sulphur;

E very particularly preferably represents —$OR^{16}$, —$SR^{16}$, —$O^-M$ or —$NR^{17}R^{18}$;

M very particularly preferably represents tetrabutylammonium trimethylbenzylammonium or represents a sodium cation ($Na^+$) or a potassium cation ($K^+$);

M furthermore very particularly preferably represents a magnesium cation ($Mg^{2+}$) or a calcium cation ($Ca^{2+}$), where in each case two molecules of a compound form a salt with such an ion;

$R^4$ very particularly preferably represents hydrogen, methyl, ethyl, n-propyl, isopropyl, n-butyl, sec-butyl, isobutyl, tert-butyl, —COMe;

$R^5$ very particularly preferably represents hydrogen, amino, formyl, methyl, ethyl, n-propyl, isopropyl, n-butyl, sec-butyl, isobutyl, tert-butyl, vinyl, allyl, propargyl, methoxy, methoxymethyl, —COMe, —COEt, tert-butoxycarbonyl, oxamoyl;

$R^4$ and $R^5$ furthermore together very particularly preferably represent ethylidene, isopropylidene, sec-butyldene, benzylidene, nitrobenzylidene;

$R^4$ and $R^5$ furthermore together with the nitrogen atom to which they are attached very particularly preferably represent a 5- or 6-membered saturated heterocycle from the group consisting of morpholine, piperidine, thiomorpholine and pyrrolidine, which may optionally be mono- or disubstituted by identical or different substituents from the group consisting of methyl, ethyl, n-propyl, isopropyl, n-butyl, sec-butyl, isobutyl and tert-butyl;

$R^9$ very particularly preferably represents hydrogen, methyl, ethyl, n-propyl, isopropyl, n-butyl, sec-butyl, isobutyl, tert-butyl, —$CH_2CF_3$, —$CH_2CF_2H$, —$CH_2CF_2CF_3$, cyclopropyl, cyclopentyl or cyclohexyl;

$R^{10}$ very particularly preferably represents fluorine, chlorine, bromine, methyl, ethyl, n-propyl, isopropyl, n-butyl, sec-butyl, isobutyl, tert-butyl, —COMe, —COEt, —$CO_2Me$, —$CO_2Et$, cyclohexyl;

or represents phenyl or benzyl, which for their part may be mono- to tetrasubstituted in the aryl moiety by identical or different substituents from the group consisting of fluorine, chlorine, bromine and methyl;

$R^{14}$ very particularly preferably represents hydrogen, methyl, ethyl, n-propyl, isopropyl, n-butyl, sec-butyl, isobutyl, tert-butyl, —$CH_2CF_3$, —$CH_2CF_2H$, —$CH_2CF_2CF_3$;

$R^{16}$ very particularly preferably represents hydrogen;

represents $C_1$–$C_{12}$-halogenoalkyl having 1 to 23 fluorine, chlorine and/or bromine atoms, $C_2$–$C_{10}$-halogenoalkenyl having 1 to 17 fluorine, chlorine and/or bromine atoms, $C_2$–$C_6$-halogenoalkinyl having 1 to 7 fluorine, chlorine and/or bromine atoms;

represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethinyl, propargyl, butinyl, each of which is optionally mono- to trisubstituted by identical or different radicals from the group consisting of fluorine, chlorine, bromine, amino, hydroxyl, cyano, nitro, methoxy, ethoxy, isopropoxy, trifluoromethoxy, —$OCH_2CF_3$, trichloromethoxy, difluoromethoxy, methylthio, trifluoromethylthio, methoxycarbonyl, ethoxycarbonyl, isopropoxycarbonyl, tert-butoxycarbonyl, methylcarbonyloxy, —O—$(CH_2)_2$—O—, phenoxy, fluorophenoxy, —$CONR^4R^5$, —$NR^4R^5$, —$ONR^4R^5$ and —CH=N—$OCH_3$;

or represents phenyl, benzyl, cyclopropyl, cyclopropylmethyl, cyclobutyl, cyclobutylmethyl, cyclopentyl, cyclopentylmethyl, cyclohexyl, cyclohexylmethyl, furyl, thienyl, oxazolyl, imidazyl, pyrazyl, thiazolyl, pyridinyl, pyrimidinyl, pyridazyl, tetrahydropyranyl, each of which is optionally mono- to trisubstituted by identical or different substituents from the group consisting of fluorine, chlorine, bromine, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_2H$, —$CF_2CHFCF_3$, —$CF_2CF_2H$, —$CH_2CF_2CF_3$, —$CF_2CHFCF_3$, —$CH_2CF_3$, methoxy, ethoxy, n-propoxy, n-butoxy, trifluoromethoxy, trichloromethoxy, methylthio, trifluoromethylthio, —$CO_2Me$, —$CO_2Et$, methylcarbonyloxy and ethylcarbonyloxy;

$R^{17}$ very particularly preferably represents hydrogen, methyl or ethyl;

$R^{18}$ very particularly preferably represents hydrogen, hydroxyl, amino, —$SO_2Me$, —$SO_2Et$, methyl, ethyl, n-propyl, isopropyl, n-butyl, sec-butyl, isobutyl, tert-butyl, allyl;

or represents phenyl, benzyl, phenylethyl, cyclopropyl, cyclopropylmethyl, cyclohexyl, pyridinyl, pyridinylmethyl, pyridinylethyl, faryl, furfuryl, each of which is optionally mono- to trisubstituted by identical or different radicals from the group consisting of fluorine, chlorine, hydroxyl, methyl, ethyl, n-propyl, isopropyl, n-butyl, sec-butyl, isobutyl, tert-butyl, trifluoromethyl, trichloromethyl, methoxy, ethoxy, trifluoromethoxy, methylthio, trifluoromethylthio and —O—$CH_2$—O—;

$R^{17}$ and $R^{18}$ furthermore together with the nitrogen atom to which they are attached very particularly preferably represent a 5- or 6-membered saturated heterocycle from the group consisting of piperazine, morpholine, piperidine and pyrrolidine, which may optionally be mono- to trisubstituted by identical or different substituents from the group consisting of methyl, ethyl, n-propyl and isopropyl;

except for the compound 2-{[4-(3,5-dimethyl-1H-pyrazol-1-yl)-2-pyrimidinyl]thio}acetamide.

Especially preferred are pyrazolylpyrimidines of the formula (I-m)

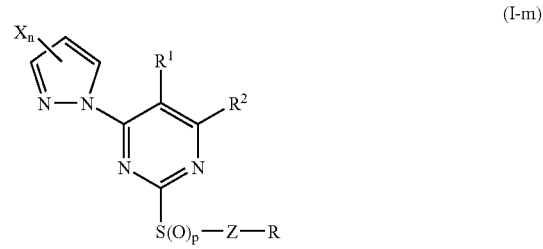

(I-m)

in which
$R^1$, $R^2$, X, n, p, Z and R have the meanings given above.

Especially preferred are pyrazolylpyrimidines of the formula (I-n)

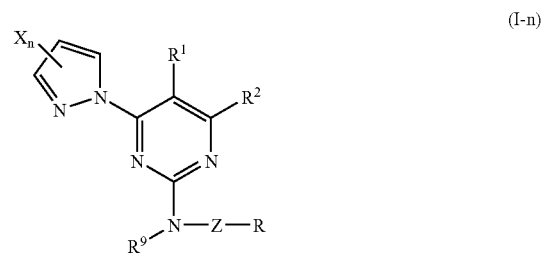

(I-n)

in which
$R^1$, $R^2$, X, n, Z, R and $R^9$ have the meanings given above.

Especially preferred are pyrazolylpyrimidines of the formula (I-o)

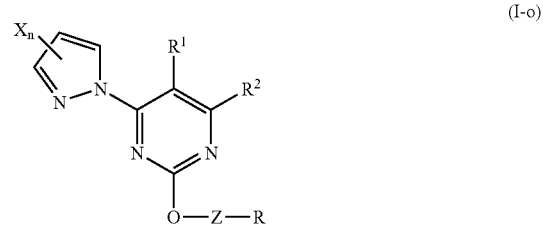

(I-o)

in which
$R^1$, $R^2$, X, n, Z and R have the meanings given above.

Especially preferred are pyrazolylpyrimidines of the formula (I-p)

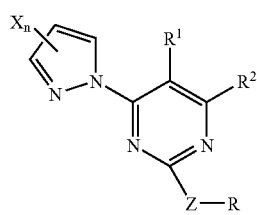

(I-p)

in which
R¹, R², X, n, Z and R have the meanings given above.

In the compounds of the formulae (I-m) to (I-q), the radicals R¹, R², X, n, Z, R and R⁹ preferably, particularly preferably and very particularly preferably have those meanings which have already been mentioned in the description of the compounds of the general formula (I) according to the invention as being preferred, particularly preferred, etc., for these radicals.

Especially preferred are pyrazolylpyrimidines of the formula (I-q)

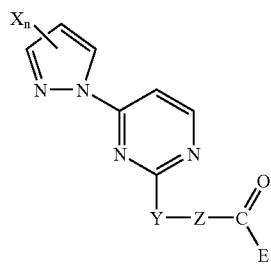

(I-q)

in which
X represents fluorine, chlorine, bromine, nitro, cyano, hydroxyl, methyl, ethyl, trifluoromethyl, methoxy, ethoxy, isopropoxy, trifluoromethoxy, trifluoromethylthio, vinyl, ethinyl, —SO₂Me, —NH², —NHMe, —NMe₂, —COMe;
or represents furyl, phenyl, chlorophenyl;
or, if n represents 2 or 3, two adjacent radicals X furthermore together represent butylene or butadienylene,
n, represents 0, 1, 2 or 3, where X represents identical or different radicals if n represents 2 or 3,
Y represents —S— or —NR⁹—,
Z represents —CH₂— or —(CH₂)₂—,
E represents hydroxyl, methoxy, ethoxy, n-propoxy, isopropoxy, n-butoxy, isobutoxy, sec-butoxy, tert-butoxy, —NH—SO₂Me, —NH—SO₂Et, —OCH₂CHF₂, —OCH₂CF₃, —OCH₂CF₂CHF₂, —OCH₂(CF₂)₂CHF₂, —OCH(CF₃)₂, —OCH(CH₃)CF₃, —O(CH₂)₂CF₃, —OCH₂CH₂Cl, —OCH₂CHCl₂, —OCH₂CCl₃,
R⁹ represents hydrogen, methyl, ethyl, n-propyl, —CH₂CF₃, —CH₂CF₂CF₃ or cyclopropyl.

Saturated hydrocarbon radicals such as alkyl can in each case be straight-chain or branched as far as this is possible, including in combination with heteroatoms, such as, for example, in alkoxy.

However, it is also possible to combine the abovementioned general or preferred radical definitions or illustrations with one another as desired, i.e. between the respective ranges and preferred ranges. The definitions apply both to the end products and, correspondingly, to the precursors and intermediates.

Using ethyl [(4-bromo-2-pyrimidinyl)thio]acetate and 4-bromopyrazole as starting materials, the course of the alternative processes (A), (B) and (C) according to the invention can be illustrated by the equation below.

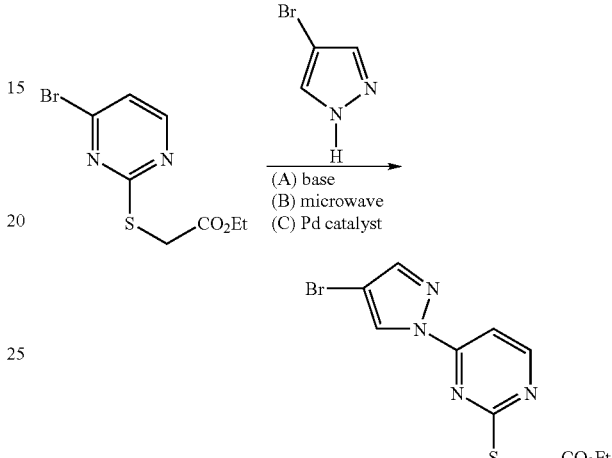

(A) base
(B) microwave
(C) Pd catalyst

Using methyl {[4-(1H-pyrazol-1-yl)-2-pyrimidinyl]thio}acetate as starting material and meta-chloroperbenzoic acid (m-CPBA) as oxidizing agent, the course of the process (D) according to the invention can be illustrated by the equation below.

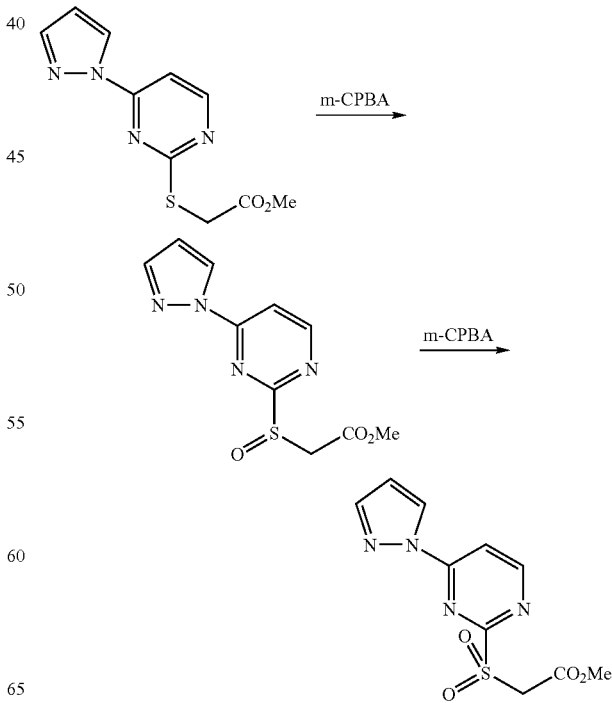

Using ethyl N-(4-chloro-2-pyrimidinyl)-N-methylglycinate and pyrazole as starting materials, the course of the process (E) according to the invention can be illustrated by the equation below.

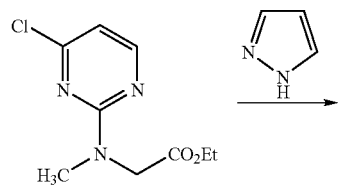

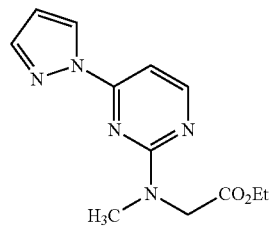

Using 2-chloro-4-(1H-pyrazol-1-yl)-pyrimidine and (3-ethoxy-3-oxopropyl)zinc bromide as starting materials, the course of the process (F) according to the invention can be illustrated by the equation below.

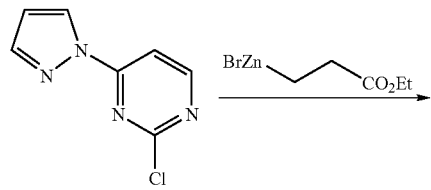

Using {[4(1H-pyrazol-1-yl)-2-pyrimidinyl]thio}acetic acid and tetrabutylammonium hydroxide as starting materials, the course of the process (G) according to the invention can be illustrated by the equation below.

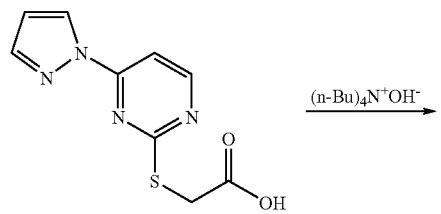

-continued

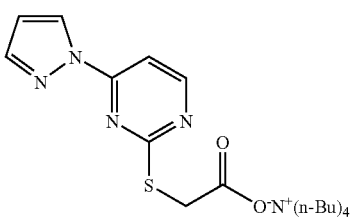

Using {[4-(1H-pyrazol-1-yl)-2-pyrimidinyl]thio}acetonitrile and trimethyltin azide as starting materials, the course of the process (H) according to the invention can be illustrated by the equation below.

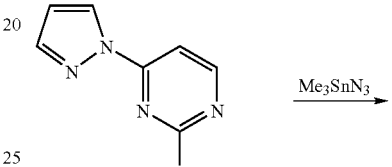

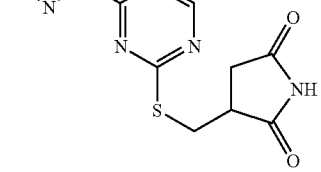

Using 1-benzyl-3-({[4-(1H-pyrazol-1-yl)-2-pyrimidinyl]thio}methyl)-2,5-pyrrolidinedione and hydrogen as starting materials and palladium/activated carbon as catalyst, the course of the process (J) according to the invention can be illustrated by the equation below.

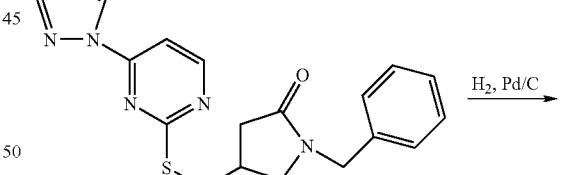

Using 1-{[4-(1-pyrazol-1-yl)-2-pyrimidinyl]thio}acetone, potassium cyanide and ammonium carbonate as starting materials, the course of the process (K) according to the invention can be illustrated by the equation below.

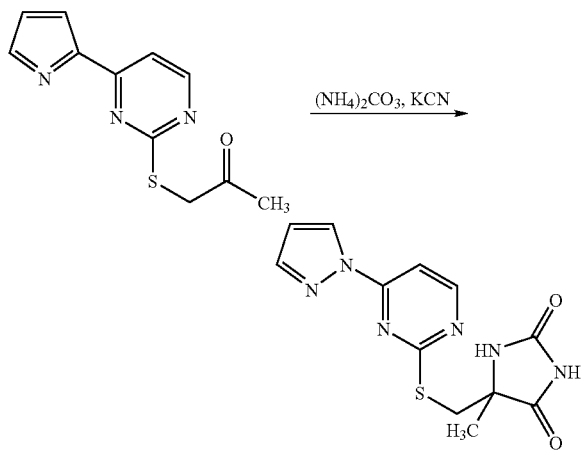

EXPLANATION OF THE PROCESSES AND INTERMEDIATES

Processes (A), (B) and (C)

The formula (II) provides a general definition of the halogenopyrimidines required as starting materials for carrying out the processes (A), (B) and (C) according to the invention. In this formula, $R^1$, $R^2$, Z and A preferably, particularly preferably and very particularly preferably have those meanings which have already been mentioned in connection with the description of the compounds of the formula (I) according to the invention as being preferred, particularly preferred, etc., for these radicals. $E^1$ preferably represents —$OR^{16}$, —$SR^{16}$ or —$NR^{17}R^{18}$. $Hal^1$ preferably represents fluorine, chlorine, bromine or iodine, particularly preferably chlorine, bromine or iodine, very particularly preferably chlorine or bromine.

Some of the halogenopyrimidines of the formula (II) are known and/or can be prepared by known processes (cf. U.S. Pat. No. 3,910,910).

The formula (III) provides a general definition of the pyrazole compounds required as starting materials for carrying out the processes (A), (B) and (C) according to the invention. In this formula, X and n preferably, particularly preferably and very particularly preferably have those meanings which have already been mentioned in connection with the description of the compounds of the formula (I) according to the invention as being preferred, particularly preferred, etc., for these radicals.

Pyrazole compounds of the formula (III) are known and/or can be prepared by known processes.

Suitable diluents for carrying out the processes (A), (B) and (C) according to the invention are in each case all customary inert organic solvents. Preference is given to using optionally halogenated aliphatic, alicyclic or aromatic hydrocarbons, such as petroleum ether, hexane, heptane, cyclohexane; methylcyclohexane; benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformamide, N-methylpyrrolidone or hexamethylphosphoric triamide.

When carrying out the process (A) according to the invention, particular preference is given to using acetonitrile, N-methylpyrrolidone or xylene.

When carrying out the process (B) according to the invention, particular preference is given to using dimethylformamide.

When carrying out the process (C) according to the invention, particular preference is given to using xylene.

Suitable bases for carrying out the process (A) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide; alkali metal hydrides, such as sodium hydride; alkali metal carbonates, such as sodium carbonate, potassium carbonate, potassium bicarbonate, sodium bicarbonate, caesium carbonate; alkali metal alkoxides, such as sodium methoxide, sodium-ethoxide, sodium isopropoxide, sodium tert-butoxide, potassium tert-butoxide; alkali metal or alkaline earth metal acetates, such as sodium acetate, potassium acetate, calcium acetate; alkali metal or alkaline earth metal phosphates, such as potassium phosphate; and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the process (A) according to the invention, particular preference is given to using potassium carbonate or caesium carbonate.

When carrying out the process (B) according to the invention, particular preference is given to using DBU.

When carrying out the process (C) according to the invention, particular preference is given to using potassium carbonate, caesium carbonate, sodium tert-butoxide or potassium phosphate.

When carrying out the process (B) according to the invention, it is possible to use any commercial microwave apparatus suitable for this reaction (for example ETHOS 1600 from MLS GmbH, Leutkirch, Germany).

When carrying out the process (C) according to the invention, in general a palladium catalyst is employed which for its part can be used with or without addition of further ligands. The catalyst used is preferably $PdCl_2(dppf)$ [dppf=1,1'-bis(diphenylphosphino)ferrocene], $Pd(PPh_3)_4$, $PdCl_2(PPh_3)_2$, $PdCl_2(CH_3CN)_2$, $Pd_2(dba)_3$ [dba=dibenzylideneacetone] or $Pd(OAc)_2$, particularly preferably $PdCl_2(dppf)$, $Pd(PPh_3)_4$, $PdCl_2(PPh_3)_2$ or $Pd(OAc)_2$, very particularly preferably $Pd(OAc)_2$.

Suitable ligands are triarylphosphines, trialkylphosphines or arsines. Preference is given to using dppf, $PPh_3$, $P(t-Bu)_3$, $biphP(t-Bu)_2$ (biph=biphenyl), $Pcy_3$ or $AsPh_3$, particularly preferably $P(t-Bu)_3$ or $biphP(t-Bu)_2$.

When carrying out the processes (A), (B) and (C) according to the invention, the reaction temperatures can in each case be varied within a relatively wide range. In general, the processes are carried out at temperatures between −20° C. and 200° C., preferably between 0° C. and 150° C.

When carrying out the process (A) according to the invention, in general 1 mol or a slight excess of the compound of the formula (III) and a base are employed per mole of the compound of the formula (II). However, it is also possible to employ the reaction components in other ratios. Work-up is carried out by customary methods. In general, the reaction mixture is concentrated and the crude product is freed from any impurities that may still be present using customary methods, such as chromatography or recrystallization.

When carrying out the process (B) according to the invention, in general 1 mol or a slight excess of the compound of the formula (III) is used per mole of the compound of the formula (II), and the reaction is carried out in a microwave apparatus. However, it is also possible to employ the reaction components in other ratios. Work-up is carried out by customary methods. In general, the reaction mixture is concentrated and the crude product is freed from any impurities that may still be present using customary methods, such as chromatography or recrystallization.

When carrying out the process (C) according to the invention, in general 1 mol or a slight excess of the compound of the formula (III) and 1–5 mol % of catalyst and 2–4 mol % of ligand are employed per mole of the compound of the formula (H).

However, it is also possible to employ the reaction components in other ratios. Work-up is carried out by customary methods. In general, the reaction mixture is concentrated and the crude product is freed from any impurities that may still be present using customary-methods, such as chromatography or recrystallization.

Process (D)

The formula (I-c) provides a general definition of the pyrazolylpyrimidines required as starting materials for carrying out the process (D) according to the invention. In this formula, $R^1$, $R^2$, X, n, Z and R preferably, particularly preferably and very particularly preferably have those meanings which have already been mentioned in connection with the description of the compounds of the formula (I) according to the invention as being preferred, particularly preferred, etc., for these radicals.

The pyrazolylpyrimidines of the formula (I-c) fall under the definition of the compounds of the formula (I) according to the invention. They can be prepared, for example, by one of the processes (A), (B), (C), (G), (H), (J) or (K) according to the invention.

Suitable oxidizing agents for carrying out the process (D) according to the invention are all oxidizing agents which are customarily used for the oxidation of sulphur. Particularly suitable are hydrogen peroxide, organic peracids, such as, for example, peracetic acid, m-chloroperbenzoic acid, p-nitroperbenzoic acid or atmospheric oxygen.

Suitable diluents for carrying out the process (D) according to the invention are likewise inert organic solvents. Preference is given to using hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide.

If appropriate, the process (D) according to the invention can be carried out in the presence of an acid binder. Suitable acid binders are all organic and inorganic acid binders customarily used. Preference is given to using alkaline earth metal or alkali metal hydroxides, acetates or carbonates, such as, for example, calcium hydroxide, sodium hydroxide, sodium acetate or sodium carbonate.

If appropriate, the process (D) according to the invention can be carried out in the presence of a suitable catalyst. Suitable catalysts are all metal salt catalysts which are customarily used for such oxidations of sulphur. In this context, ammonium molybdate and sodium tungstate may be mentioned by way of example.

When carrying out the process (D) according to the invention, the reaction temperatures can be varied within a relatively wide range. In general, the process is carried out at temperatures between −20° C. and +70° C., preferably at temperatures between 0° C. and +50° C.

For carrying out the process (D) according to the invention, in general from 0.8 to 1.2 mol, preferably equimolar amounts, of oxidizing agent are used per mole of the compound of the formula (I-c) if the oxidation of the sulphur is to be stopped at the sulphoxide stage. For the oxidation to the sulphone, in general from 1.8 to 3.0 mol, preferably twice the molar amount, of oxidizing agent is used per mole of the compound of the formula (I-c). However, it is also possible to employ the reaction components in other ratios. Work-up is carried out by customary methods. In general, the reaction mixture is concentrated and extracted and the organic phase is washed, dried, filtered and concentrated. The residue is, if appropriate, freed from any impurities that may still be present using customary methods, such as chromatography or recrystallization.

Process (E)

The formula (IV) provides a general definition of the halogenopyrimidines required as starting materials for carrying out the process (E) according to the invention. In this formula, $R^1$, $R^2$ and Z preferably, particularly preferably and very particularly preferably have those meanings which have already been mentioned in connection with the description of the compounds of the formula (I) according to the invention as being preferred, particularly preferred, etc., for these radicals. $Hal^2$ preferably represents fluorine, chlorine, bromine or iodine, particularly preferably chlorine, bromine or iodine, very particularly preferably chlorine or bromine. $R^a$ has the meanings given above.

The halogenopyrimidines of the formula (IV) are novel. They can be prepared by a) reacting pyrimidine compounds of the formula (XII)

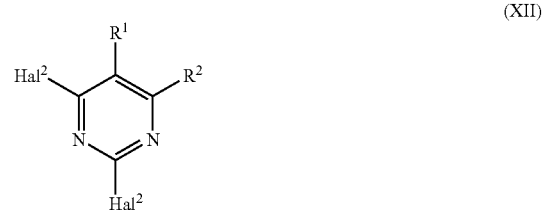

(XII)

in which
$R^1$, $R^2$ and $Hal^2$ have the meanings given above,
with compounds of the formula (XII)

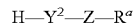  (XIII)

in which
$Y^2$ and $R^a$ have the meanings given above,
if appropriate in the presence of a base (for example triethylamine) and if appropriate in the presence of a diluent (for example dioxane).

The formula (XII) provides a general definition of the pyrimidine compounds required as starting materials for carrying out the process (a). In this formula, $Hal^2$ preferably represents fluorine, chlorine, bromine or iodine, particularly preferably chlorine, bromine or iodine. $Y^2$ preferably represents oxygen or —$NR^9$—. $R^1$, $R^2$ and $R^9$ preferably, particularly preferably and very particularly preferably have those meanings which have already been mentioned in connection with the description of the compounds of the formula (I) according to the invention as being preferred, particularly preferred, etc., for these radicals.

Pyrimidine compounds of the formula (XII) are known and/or can be prepared by known methods.

The formula (XIII) provides a general definition of the compounds furthermore required as starting materials for carrying out the process (a). In this formula, $Y^2$ preferably represents oxygen or —$NR^9$—. Z and $R^9$ preferably, particularly preferably and very particularly preferably have those meanings which have already been mentioned in connection with the description of the compounds of the formula (I) according to the invention as being preferred, particularly preferred, etc., for these radicals. $R^a$ has the meanings given above.

Compounds of the formula (XIII) are known and/or can be prepared by known methods.

The pyrazole compounds of the formula (III) required as starting materials for carrying out the process (E) according to the invention have already been described in connection with the explanation of the process (A) according to the invention.

Suitable diluents for carrying out the process (E) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide. Particular preference is given to using N-methylpyrrolidone or xylene.

Suitable bases for carrying out the process (E) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal hydrides, such as sodium hydride, alkali metal carbonates, such as sodium carbonate, potassium carbonate, potassium bicarbonate, sodium bicarbonate, caesium carbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). Particular preference is given to using alkaline earth metal or alkali metal carbonates or alkali metal hydrides or DBU, very particularly preferably potassium carbonate, caesium carbonate and DBU.

It is also possible to carry out the process (E) according to the invention in the presence of a catalyst. In general, a palladium catalyst is employed, which for its part can be used with or without addition of further ligands. The catalyst used is preferably $PdCl_2(dppf)$ [dppf=1,1'-bis(diphenylphosphino)ferrocene], $Pd(PPh_3)_4$, $PdCl_2(PPh_3)_2$, $PdCl_2(CH_3CN)_2$, $Pd_2(dba)_3$ [dba=dibenzylideneacetone] or $Pd(OAc)_2$, particularly preferably $PdCl_2(dppf)$, $Pd(PPh_3)_4$, $PdCl_2(PPh_3)_2$, or $Pd(OAc)_2$, very particularly preferably $Pd(OAc)_2$.

Suitable ligands are triarylphosphines, trialkylphosphines or arsines. Preference is given to using dppf, $PPh_3$, $P(t-Bu)_3$, biphP(t-Bu)$_2$ (biph=biphenyl), $Pcy_3$ or $AsPh_3$, particularly preferably $P(t-Bu)_3$ or biphP(t-Bu)$_2$.

When carrying out the process (E) according to the invention, the reaction temperatures can in each case be varied within a relatively wide range. In general, the process is carried out at temperatures between −20° C. and 200° C., preferably between 0° C. and 150° C.

When carrying out the process (E) according to the invention, in general 1 mol or a slight excess of the compound of the formula (III) is employed per mole of, the compound of the formula (IV). However, it is also possible to employ the reaction components in other ratios. Work-up is carried out by customary methods. In general, the reaction mixture is concentrated and the crude product is freed from any impurities that may still be present using customary methods, such as chromatography or recrystallization.

Process (F)

The formula (V) provides a general definition of the pyrazolylpyrimidine halides required as starting materials for carrying out the process (F) according to the invention. In this formula, $R^1$, $R^2$, X and n preferably, particularly preferably and very particularly preferably have those meanings which have already been mentioned in connection with the description of the compounds of the formula (I) according to the invention as being preferred, particularly preferred, etc., for these radicals. $Hal^3$ preferably represents fluorine, chlorine, bromine or iodine, particularly preferably chlorine, bromine or iodine.

Pyrazolylpyrimidine halides of the formula (V) are novel. They can be prepared by b) reacting pyrimidine compounds of the formula (XIV)

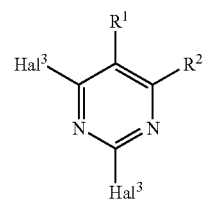

(XIV)

in which
$R^1$, $R^2$ and $Hal^3$ have the meanings given above,
with pyrazole compounds of the formula (III)

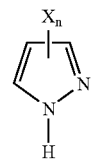

(III)

in which
X and n have the meanings given above,
if appropriate in the presence of a base (for example caesium carbonate) and if appropriate in the presence of a diluent (for example dioxane).

The formula (XIV) provides a general definition of the pyrimidine compounds required as starting materials for carrying out the process (b). In this formula, $R^1$ and $R^2$ preferably, particularly preferably and very particularly preferably have those meanings which have already been mentioned in connection with the description of the compounds of the formula (I) according to the invention as being preferred, particularly preferred, etc., for these radicals. $Hal^3$ preferably represents fluorine, chlorine, bromine or iodine, particularly preferably chlorine, bromine or iodine.

Pyrimidine compounds of the formula (XIV) are known and/or can be prepared by known methods.

The pyrazole compounds of the formula (III) required as starting materials for carrying out the process (b) have already been described in connection with the explanation of the process (A) according to the invention.

The formula (VI) provides a general definition of the organometallic compounds required as starting materials for carrying out the process (F1) according to the invention. In this formula, Z, A and E preferably, particularly preferably and very particularly preferably have those meanings which have already been mentioned in connection with the description of the compounds of the formula (I) according to the invention as being preferred, particularly preferred, etc., for these radicals.

Organometallic compounds of the formula (VI) are known and/or can be prepared by known processes.

The formula (VII) provides a general definition of the organometallic compounds required as starting materials for carrying out the process (F2) according to the invention. In this formula, Z preferably, particularly preferably and very particularly preferably has those meanings which have already been mentioned in connection with the description of the compounds of the formula (I) according to the invention as being preferred, particularly preferred, etc., for these radicals.

Organometallic compounds of the formula (VII) are known and/or can be prepared by known processes.

The trialkyltin azides required for carrying out the process (F2) according to the invention are known. Preference is given to using trimethyltin azide or tri(n-butyl)tin azide.

Suitable diluents for carrying out the process (F) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane.

Suitable bases for carrying out the process (F) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal hydrides, such as sodium hydride, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the process (F) according to the invention, in general a palladium catalyst is employed, which for its part can be used with or without addition of further ligands. The catalyst used is preferably $PdCl_2(dppf)$ [dppf=1,1'-bis(diphenylphosphino)ferrocene], $Pd(PPh_3)_4$, $PdCl_2(PPh_3)_2$, $PdCl_2(CH_3CN)_2$, $Pd_2(dba)_3$ [dba=dibenzylideneacetone] or $Pd(OAc)_2$.

Suitable ligands are triarylphosphines, trialkylphosphines or arsines. Preference is given to using dppf, $PPh_3$, $P(t-Bu)_3$, $biphP(t-Bu)_2$ (biph=biphenyl), $Pcy_3$ or $AsPh_3$.

When carrying out the process (F) according to the invention, the reaction temperatures can in each case be varied within a relatively wide range. In general, the process is carried out at temperatures between −20° C. and 200° C., preferably between 0° C. and 150° C.

When carrying out the process (F) according to the invention, in general either 1 mol or a slight excess of the compound of the formula (VI) or, alternatively, in a first step 1 mol or a slight excess of the compound of the formula (VII) and then, in a second step, 1 mol or a slight excess of a trialkyltin azide are employed per mole of the compound of the formula (V). However, it is also possible to employ the reaction components in other ratios. Work-up is carried out by customary methods. In general, the reaction mixture is concentrated and extracted and the organic phase is washed, dried, filtered and concentrated. The residue is, if appropriate, freed from any impurities that may still be present using customary methods, such as chromatography or recrystallization.

Process (G)

The formula (I-g) provides a general definition of the pyrazolylpyrimidines required as starting materials for carrying out the process (G) according to the invention. In this formula, $Y^3$ preferably represents a direct bond, oxygen, sulphur or —$NR^9$—. $R^1$, $R^2$, X, n, Z, A and $R^9$ preferably, particularly preferably and very particularly preferably have those meanings which have already been mentioned in connection with the description of the compounds of the formula (I) according to the invention as being preferred, particularly preferred, etc., for these radicals.

Pyrazolylpyrimidines of the formula (I-g) are likewise compounds according to the invention; they can be prepared, for example, by c) treating esters of the formula (I-r)

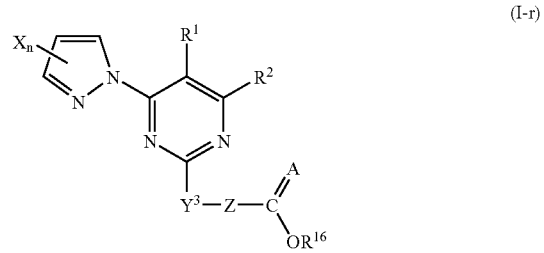

(I-r)

in which

R¹, R², X, n, Y³, A and R¹⁶ have the meanings given above, with a base (for example sodium hydroxide), if appropriate in the presence of a diluent (for example methanol).

Pyrazolylpyrimidines of the formula (I-r) also form part of the subject-matter of this invention. They can be prepared, for example, by one of the processes (A), (B), (C) or (G) according to the invention.

The formula (IX) provides a general definition of the hydroxides required as starting materials for carrying out the process (G) according to the invention. In this formula, M preferably, particularly preferably and very particularly preferably has those meanings which have already been mentioned in connection with the description of the compounds of the formula (I) according to the invention as being preferred, particularly preferred, etc., for these radicals.

Hydroxides of the formula (IX) are known and/or can be prepared by known processes.

Suitable diluents for carrying out the process (G) according to the invention are in each case all customary protic solvents. Preference is given to using water or alcohols, such as methanol or ethanol; nitriles, such as acetonitrile, propionitrile, n- or isobutyronitrile or benzonitrile. Particular preference is given to using water or alcohols.

When carrying out the process (G) according to the invention, the reaction temperatures can in each case be varied within a relatively wide range. In general, the process is carried out at temperatures between 0° C. and 200° C., preferably between 0° C. and 150° C., very particularly preferably between 20° C. and 100° C.

When carrying out the process (G) according to the invention, in general 1 mol or a slight excess of the compound of the formula (IX) is employed per mole of the compound of the formula (I-g). However, it is also possible to employ the reaction components in other ratios. Work-up is carried out by customary methods. In general, the reaction mixture is concentrated and extracted and the organic phase is washed, dried, filtered and concentrated. The residue is, if appropriate, freed from any impurities that may still be present using customary methods, such as chromatography or recrystallization.

Process (H)

The formula (X) provides a general definition of the nitriles required as starting materials for carrying out the process (H) according to the invention. In this formula, R¹, R², X, n and Z preferably, particularly preferably and very particularly preferably have those meanings which have already been mentioned in connection with the description of the compounds of the formula (I) according to the invention as being preferred, particularly preferred, etc., for these radicals.

Nitriles of the formula (X) are novel. They can be prepared by d) reacting thiols of the formula (XV)

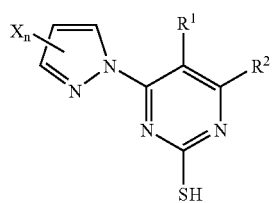

(XV)

in which

R¹, R², X and n have the meanings given above, with chlorinated nitriles of the formula (XVI)

$$Cl-Z-CN \qquad (XVI)$$

in which

Z has the meanings given above, if appropriate in the presence of a diluent (for example toluene) and if appropriate in the presence of an acid binder (for example sodium hydroxide).

The formula (XV) provides a general definition of the thiols required as starting materials for carrying out the process (d). In this formula, R¹, R², X and n preferably, particularly preferably and very particularly preferably have those meanings which have already been mentioned in connection with the description of the compounds of the formula (I) according to the invention as being preferred, particularly preferred, etc., for these radicals.

Thiols of the formula (XV) are novel. They can be prepared, for example, by e) reacting 4-chloro-2-pyrimidinethiol with pyrazole compounds of the formula (III)

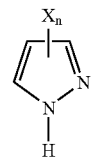

(III)

in which

X and n have the meanings given above, if appropriate in the presence of a base (for example caesium carbonate) and if appropriate in the presence of a diluent (for example n-methylpyrrolidone).

The pyrazole compounds of the formula (III) required as starting materials for carrying out the process (e) have already been described in connection with the explanation of the process (A) according to the invention.

The formula (XVI) provides a general description of the chlorinated nitriles required as starting materials for carrying out the process (d). In this formula, Z preferably, particularly preferably and very particularly preferably has those meanings which have already been mentioned in connection with the description of the compounds of the formula (I) according to the invention as being preferred, particularly preferred, etc., for these radicals.

Chlorinated nitriles of the formula (XVI) are known.

The trialkyltin azides required for carrying out the process (H) according to the invention are known. Preference is given to using trimethyltin azide or tri(n-butyl)tin azide.

Suitable diluents for carrying out the process (H) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane. Particular preference is given to using toluene.

When carrying out the process (H) according to the invention, in general 1 mol or a slight excess of a trialkyltin azide is employed per mole of the compound of the formula (X). However, it is also possible to employ the reaction components in other ratios. Work-up is carried out by customary methods. In general, the reaction mixture is concentrated and extracted and the organic phase is washed, dried, filtered and concentrated. The residue is, if appropriate, freed from any impurities that may still be present using customary methods, such as chromatography or recrystallization.

Process (J)

The formula (I-k) provides a general definition of the pyrazolylpyrimidines required as starting materials for carrying out the process (J) according to the invention. In this formula, $Y^3$>preferably represents a direct bond, oxygen, sulphur or —$NR^9$—, $R^1$, $R^2$, X, n, Z and $R^9$ preferably, particularly preferably and very particularly preferably have those meanings which have already been mentioned in connection with the description of the compounds of the formula (I) according to the invention as being preferred, particularly preferred, etc., for these radicals.

Pyrazolylpyrimidines of the formula (I-k) are novel. They can be prepared by f) reacting succinimides of the formula (XVII)

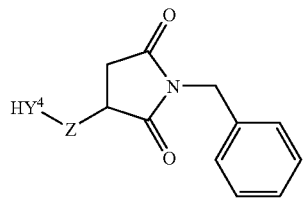

(XVII)

in which
$Y^4$ represents oxygen, sulphur or —$NR^9$—,
Z and $R^9$ have the meanings given above
or
Grignard reagents of the formula (XVIII)

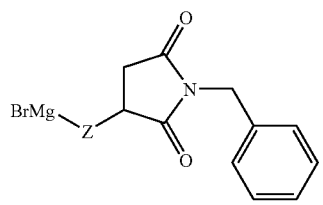

(XVIII)

in which
Z has the meanings given above,
with methylsulphonylpyrimidines of the formula (XIX)

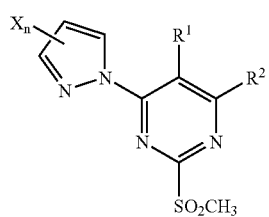

(XIX)

in which
$R^1$, $R^2$, X and n have the meanings given above,
if appropriate in the presence of a diluent (for example tetrahydrofuran) and if appropriate in the presence of an acid binder (for example triethylamine).

The formula (XVII) provides a general definition of the succinimides required as starting materials for the process (f). In this formula, $Y^4$ preferably represents oxygen, sulphur or —$NR^9$—. Z and $R^9$ preferably, particularly preferably and very particularly preferably have those meanings which have already been mentioned in connection with the description of the compounds of the formula (I) according to the invention as being preferred, particularly preferred, etc., for these radicals.

The formula (XVIII) provides a general definition of the Grignard reagents required as starting materials for the process (f). In this formula, Z preferably, particularly preferably and very particularly preferably has those meanings which have already been mentioned in connection with the description of the compounds of the formula (I) according to the invention as being preferred, particularly preferred, etc., for these radicals.

Succinimides of the formula (XVII) and Grignard reagents of the formula (XVIII) are known and/or can be prepared by known processes.

The formula (XIX) provides a general definition of the methylsulphonylpyrimidines required as starting materials for carrying out the process (f). In this formula, $R^1$, $R^2$ X and n preferably, particularly preferably and very particularly preferably have those meanings which have already been mentioned in connection with the description of the compounds of the formula (I) according to the invention as being preferred, particularly preferred, etc., for these radicals.

Methylsulphonylpyrimidines of the formula (XIX) are novel. They can be prepared by g) treating methylthiopyrimidines of the formula (XX)

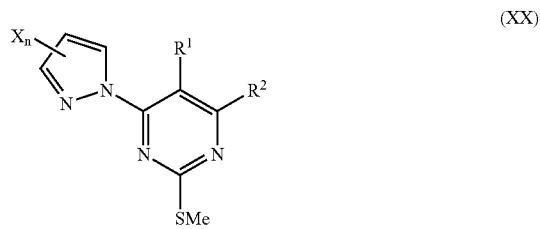

(XX)

in which
$R^1$, $R^2$, X and n have the meanings given above,
with an oxidizing agent (for example m-chloroperbenzoic acid), if appropriate in the presence of a diluent (for example chloroform).

The formula (XX) provides a general definition of the methylthiopyrimidines required as starting materials for carrying out the process (g). In this formula, $R^1$, $R^2$, X and n preferably, particularly preferably and very particularly preferably have those meanings which have already been mentioned in connection with the description of the compounds of the formula (I) according to the invention as being preferred, particularly preferred, etc., for these radicals.

Methylthiopyrimidines of the formula (XX) are novel. They can be prepared by h) reacting pyrimidine derivatives of the formula (XXI)

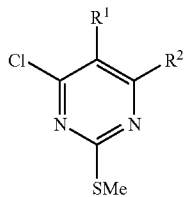

(XXI)

in which
R$^1$ and R$^2$ have the meanings given above,
with pyrazole compounds of the formula (III)

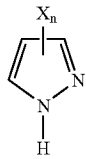

(III)

in which
X and n have the meanings given above,
if appropriate in the presence of a base (for example caesium carbonate) and if appropriate in the presence of a diluent (for example N-methylpyrrolidone).

The formula (XXI) provides a general definition of the pyrimidine derivatives required as starting materials for carrying out the process (h). In this formula, R$^1$ and R$^2$ preferably, particularly preferably and very particularly preferably have those meanings which have already been mentioned in connection with the description of the compounds of the formula (I) according to the invention as being preferred, particularly preferred, etc., for these radicals.

The pyrazole compounds of the formula (III) required as starting materials for carrying out the process (h) have already been described in connection with the explanation of the process (A) according to the invention.

Some of the compounds of the formula (XXI) are known. They can be prepared, for example, by j) reacting methylthiopyrimidines of the formula (XXII)

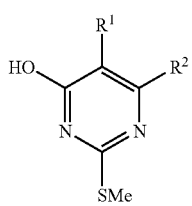

(XXII)

in which
R$^1$ and R$^2$ have the meanings given above,
with a chlorinating agent (for example POCl$_3$).

The formula (XXII) provides a general definition of the methylthiopyrimidines required as starting materials for carrying out the process (j). In this formula, R$^1$ and R$^2$ preferably, particularly preferably and very particularly preferably have those meanings which have already been mentioned in connection with the description of the compounds of the formula (I) according to the invention as being preferred, particularly preferred, etc., for these radicals.

Compounds of the formula (XXII) are known and/or can be prepared by known processes.

Suitable diluents for carrying out the process (J) according to the invention are in each case all customary inert organic solvents. Preference is given to using nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; esters, such as methyl acetate or ethyl acetate; sulphoxides, such as dimethyl sulphoxide; or sulphones, such as sulpholane. Particular preference is given to using nitriles, amides or sulphoxides, very particularly preferably acetonitrile, dimethylformamide, tetrahydrofuran or dimethyl sulphoxide.

Suitable catalysts for carrying out the process (J) according to the invention are all catalysts customary for hydrogenation reactions. Preference is given to using palladium or platinum catalysts, particularly preferably palladium/activated carbon.

When carrying out the process (J) according to the invention, the reaction temperatures can in each case be varied within a relatively wide range. In general, the process is carried out at temperatures between –20° C. and 200° C., preferably between 0° C. and 150° C.

When carrying out the process (J) according to the invention, in general 1–10 mol % of a catalyst are employed per mole of the compound of the formula (I-k), and the reaction is carried out under a hydrogen pressure of from 1 to 50 bar. However, it is also possible to employ the reaction components in other ratios. Work-up is carried out by customary methods. In general, the reaction mixture is concentrated and extracted and the organic phase is washed, dried, filtered and concentrated. The residue is, if appropriate, freed from any impurities that may still be present using customary methods, such as chromatography or recrystallization.

Process (K)

The formula (XI) provides a general definition of the keto compounds required as starting materials for carrying out the process (K) according to the invention. In this formula, Y$^3$ preferably represents a direct bond, oxygen, sulphur or —NR$^9$—. R$^1$, R$^2$, X, n, Z and R$^9$ preferably, particularly preferably and very particularly preferably have those meanings which have already been mentioned in connection with the description of the compounds of the formula (I) according to the invention as being preferred, particularly preferred, etc., for these radicals.

Keto compounds of the formula (XI) are novel. They can be prepared by k) reacting compounds of the formula (XXIII)

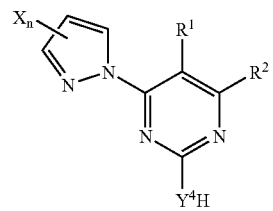

(XXIII)

in which
R¹, R², X, n and Y⁴ have the meanings given above,
with methyl ketones of the formula (XXIV)

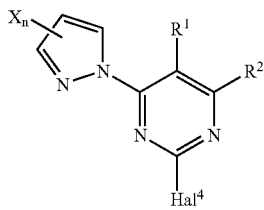
(XXIV)

in which
Z has the meanings given above,
if appropriate in the presence of a diluent (for example tetrahydrofuran) and if appropriate in the presence of an acid binder (for example triethylamine), or l) reacting pyrazolylpyrimidine halides of the formula (XXV)

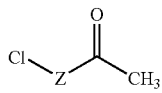
(XXV)

in which
R¹, R², X and n have the meanings given above,
Hal⁴ represents halogen
with Grignard reagents of the formula (XXVI)

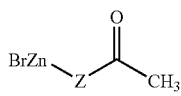
(XXVI)

in which
Z has the meaning given above,
if appropriate in the presence of a diluent (for example tetrahydrofuran) and if appropriate in the presence of an acid binder (for example triethylamine) and if appropriate in the presence of a catalyst [for example Pd(PPh₃)₄].

The formula (XXIII) provides a general definition of the compounds required as starting materials for carrying out the process (k). In this formula, Y⁴ preferably represents oxygen, sulphur or —NR⁹—. R¹, R², X, n and R⁹ preferably, particularly preferably and very particularly preferably have those meanings which have already been mentioned in connection with the description of the compounds of the formula (I) according to the invention as being preferred, particularly preferred, etc., for these radicals.

Compounds of the formula (XXIII) are known and/or can be prepared by known processes [for example according to process (e)].

The formula (XXIV) provides a general definition of the methyl ketones required as starting materials for carrying out the process (k). In this formula, Z preferably, particularly preferably and very particularly preferably has those meanings which have already been mentioned in connection with the description of the compounds of the formula (I) according to the invention as being preferred, particularly preferred, etc., for these radicals.

Methyl ketones of the formula (XXIV) are known and/or can be prepared by known processes.

The formula (XXV) provides a general definition of the pyrazolylpyrimidine halides required as starting materials for carrying out the process (l). In this formula, R¹, R², X and n preferably, particularly preferably and very particularly preferably have those meanings which have already been mentioned in connection with the description of the compounds of the formula (I) according to the invention as being preferred, particularly preferred, etc., for these radicals. Hal⁴ preferably represents chlorine, bromine or iodine, particularly preferably bromine or iodine, very particularly preferably iodine.

Pyrazolylpyrimidine halides of the formula (XXV) can be prepared, for example, according to process (b).

The formula (XXVI) provides a general definition of the Grignard reagents required as starting materials for carrying out the process (l). In this formula, Z preferably, particularly preferably and very particularly preferably has those meanings which have already been mentioned in connection with the description of the compounds of the formula (I) according to the invention as being preferred, particularly preferred, etc., for these radicals.

Grignard reagents of the formula (XXVI) are known and/or can be prepared by known processes.

Suitable diluents for carrying out the process (K) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane. Particular preference is given to using toluene.

When carrying out the process (K) according to the invention, in general 1 mol or a slight excess of ammonium carbonate and 1 mol or a slight excess of potassium cyanide are employed per mole of the compound of the formula (XI). However, it is also possible to employ the reaction components in other ratios. Work-up is carried out by customary methods. In general, the reaction mixture is concentrated and extracted and the organic phase is washed, dried, filtered and concentrated. The residue is, if appropriate, freed from any impurities that may still be present using customary methods, such as chromatography or recrystallization.

All processes according to the invention are generally carried out under atmospheric pressure. However, in each case it is also possible to operate under elevated or reduced pressure.

The active compounds according to the invention are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals.

They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus, Gryllotalpa* spp., *Locusta migratoria migratorioides, Melanoplus* spp. and *Schistocerca gregaria*.

From the order of the Blattaria, for example, *Blatta orientalis, Periplaneta americana, Leucophaea maderae* and *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis*.

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phyloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Chematobia brumata, Lithocoiletis biancardeila, Hyponomeuta padelia, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticuilana, Choristoneura fumiferana, Clysia ambiguella, Homona magnanima, Tortrix viridana, Cnaphalocerus* spp. and *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphoriaptera, for example, *Xenopsylla cheopis* and *Ceratophyllus* spp.

From the class of the Arachnida, for example, *Scorpio maurus, Latrodectus mactans, Acarus siro, Argas* spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

In particular, the compounds of the formula (I) according to the invention have excellent activity against caterpillars, beetle larvae, spider mites, aphids and leaf-mining flies.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds according to the invention can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds according to the invention with extenders, that is to say liquid solvents and/or solid carriers, optionally with the use of surfactants, that is to say emulsifiers and/or dispersants and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, anapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks;

suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates;

suitable dispersants are: for example lignosulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be present in commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly suitable co-components are, for example, the following compounds:

Fungicides:
aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenrarimol, fenbuconazole, fenfuram, fenitropan, fenpiclonil, fenpropidin, fenpropmorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, of urace, oxadixyl, oxamocarb, oxolinic acid, oxycarboxim, oxyfenthin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecioftalam, techazene, tetcyclasis, tetraconazole, tniabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G, OK-8705, OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methyl ethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxofuranyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxymethanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one.

Bactericides:
bronopol, dichlorophen, nitrapyrin, nickel dimethyldithiocarbamate, kasugamycin, octhilinone, furancarboxylic acid, oxytetracyclin, probenazole, streptomycin, teclothialam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpytidaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloetbocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, *Entomopfthora* spp., eprinomectin, esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb,
   granulosis viruses,
   halofenozide, HCH, heptenophos, hexaflumuron, hexythiazox, hydroprene,
   imidacloprid, isazofos, isofenphos, isoxathion, ivermectin,
   nuclear polyhedrosis viruses,
   lambda-cyhalothrin, lufenuron,
   malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos,
   naled, nitenpyram, nithiazine, novaluron,
   omethoate, oxamyl, oxydemyethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos,
   ribavirin,
   salithion, sebufos, selamectin, silafluofen, spinosad, sulfotep, sulprofos,
   tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
   vamidothion, vaniliprole, *Verticillium lecanii*,
   YI 5302,
   zeta-cypermethrin, zolaprofos,
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethyl cyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)-4-methylphyenyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N''-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds according to the invention, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having specific properties ("traits") which have been obtained by conventional breeding, by mutagenesis or by recombinant DNA techniques. This can be varieties, bio- and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which extend beyond the effects which were actually to be expected.

The preferred transgenic plants or plant cultivars (i.e. those obtained by genetic engineering) which are to be treated according to the invention include all plants which, in the genetic modification, received genetic material which imparted particularly advantageous useful properties ("trits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed in the plants by the genetic, material from *Bacillus thermogensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of plants to fungi, bacteria and viruses by systemic acquired resistance (SAR), systemin, phytoalexius, elicitous and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but, also in the veterinary medicine sector against animal parasites (ectoparasites), such as hard ticks, soft ticks, mange mites, leaf mites, ilies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Omithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against the development stages of ticks, against flies and against fleas.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.)

should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also within the aid of moulded articles containing the active compound, such as collars, ear marks, tail marks, limb bands, halters, marking devices and the like.

When used for cattle, poultry, pets and the like, the active compounds of the formula (I) according to the invention can be used as formulations (for example powders, emulsions, free-flowing compositions), which comprise the active compounds according to the invention in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec and *Dinoderus minutus.*

Hymenopterons, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptoterrnes formosanus.*

Bristletails, such as *Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed, wood products which can be protected by the agent according to the invention or mixtures comprising it are to be understood as meaning, for example:

building timber, wooden beams, railway sleepers, bridge components, boat jetties, wooden vehicles, boxes, pallets, containers, telegraph poles, wood panelling, wooden window frames and doors, plywood, chipboard, joinery or wooden products which are used quite generally in house-building or in building joinery.

The active compounds according to the invention can be used as such, in the form of concentrates or in generally customary formulations, such as powders, granules, solutions, suspensions, emulsions or pastes.

The formulations mentioned can be prepared in a manner known per se, for example by mixing the active compounds according to the invention with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flash-point above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate- or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyflutlrin, cypermethrin, deltamethrin, perrnethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octylisothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trinalkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
  algicides such as
  2-tert-butylamino-4-cyclopropylamino-6-methylthio-1,3, 5-triazine, dichlorophen, diuron, endothal, fentin acetate, isoproturon, methabenzthiazuron, oxyfluorfen, quinoclamine and terbutryn;
  fungicides such as
  benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
  molluscicides such as
  fentin acetate, metaldehyde, methiocarb, niclosamid, thiodicarb and trimethacarb;
  or conventional antifouling active compounds such as
  4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all development stages.

These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae,*
*Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctelal, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive evaporation systems, moth papers, moth bags and moth gels, as granules or dusts, in baits for spreading or in bait stations.

The preparation and use of the substances according to the invention is shown in the examples below.

PREPARATION EXAMPLES

Example 1

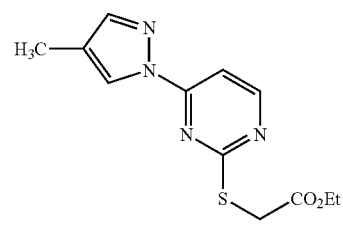

2.0 g (7.22 mmol) of ethyl [(4-bromo-2-pyrimidinyl)thio] acetate, 66 mg (1 mol %) of Pd(OAc)$_2$, 44 mg (3 mol %) of P(t-Bu)$_3$, 3.0 g (21.6 mmol, 3 eq) of potassium carbonate (ground) and 0.54 g (6.56 mmol) of 4-methyl-1H-pyrazole in 100 ml of xylene are heated at 120° C. for 18 h. The mixture is washed twice with water, the aqueous phase is extracted once with toluene, the organic phases are combined, washed with saturated NaCl solution and dried and the solvent is distilled off. The residue is purified by silica gel chromatography (n-hexane/ethyl acetate 4:1).

This gives 0.58 g (29% of theory) of ethyl {[4-(4-methyl-1H-pyrazol-1-yl)-2-pyrimidinyl]thio}acetate.

| HPLC: | Logp (pH 2.3) = 2.28 |
|---|---|
| M.p.: | 72° C. |

Example 2

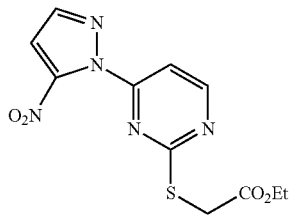

1.0 g (4.3 mmol) of ethyl [(4-chloro-2-pyrimidinyl)thio]acetate, 0.53 g (4.7 mmol) of 5-nitro-1H-pyrazole and 0.65 g (4.3 mmol) of 1,8-diazabicyclo[5.4.0]undec-7-ene (DBU) are dissolved in 10 ml of DMF and, over a period of 3 min, heated in a microwave apparatus to 140° C. After 20 min, the mixture is cooled to about 70° C. and then once more heated at 140° C. for 20 min. The mixture is cooled, concentrated and purified by preparative HPLC.

This gives 0.61 g (46% of theory) of ethyl {[4-(5-nitro-1H-pyrazol-1-yl)-2-pyrimidinyl]thio}acetate.

| HPLC: | Logp (pH 2.3) = 2.55. |
|---|---|

Example 3

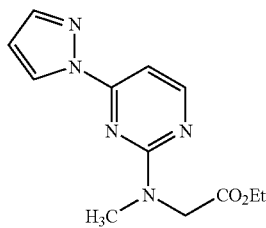

0.5 g (2.18 mmol) of ethyl N-(4-chloro-2-pyrimidinyl)-N-methylglycinate and 1.78 g (3.27 mmol) of cesium carbonate are initially charged in 30 ml of N-methylpyrrolidone, and 0.16 g (2.35 mmol) of pyrazole is added a little at a time. The mixture is heated at 120° C. for 3 h and then admixed with 25 ml of water and extracted twice with ethyl acetate. The combined organic phases are dried and concentrated and the residue is purified by silica gel chromatography (gradient cyclohexane/ethyl acetate 3:1 to 1:3).

This gives 0.23 g (40% of theory) of ethyl N-methyl-N-[4-(1H-pyrazol-1-yl)-2-pyrimidinyl]glycinate.

| HPLC: | Logp (pH 2.3) = 2.10 |
|---|---|

Preparation of Starting Materials:
Ethyl N-(4-chloro-2-pyrimidinyl)-N-methylglycinate

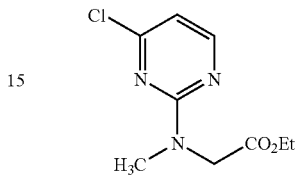

30.0 g (0.20 mol) of 2,4-dichloropyrimidine, 30.9 g (0.20 mol) of ethyl N-methylglycinate and 61.0 g (0.60 mol) of triethylamine in 200 ml of dioxane are stirred at 50° C. for 10 min. The mixture is filtered off with suction and the mother liquor is concentrated to half the original volume. A solid crystallizes out, which is filtered off with suction. The mother liquor is concentrated, the residue is stirred with petroleum ether and the product is filtered off.

| Yield: | 11.1 g (24% of theory) |
|---|---|
| M.p.: | 48° C. |

Ethyl [(4-bromo-2-pyrimidinyl)thio]acetate

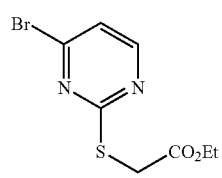

Under argon, 52.5 g (0.20 mol) of triphenylphosphine are initially charged in 600 ml of dioxane, and 35.6 g (0.20 mol) of N-bromosuccinimide are added a little at a time, with cooling. The mixture is stirred at RT for 30 min. 8.6 g (0.04 mol) of ethyl [(4-hydroxy-2-pyrimidinyl)thio]acetate are then added and the mixture is heated at reflux for 45 min. A total of 2 l of water are added to the mixture, which is then extracted 3× with in each case 300 ml of methyl tert-butyl ketone. The organic phase is washed 2× with water and 1× with concentrated NaCl solution, dried over magnesium sulphate and concentrated. The residue is stirred in 60 ml of methyl tert-butyl ketone and filtered off. The mother liquor is concentrated and the residue is purified by silica gel chromatography (dichloromethane).

| Yield: | 7.9 g (70% of theory) as an oil. |
|---|---|
| HPLC: | Logp (pH 2.3) = 2.27 |

The compounds listed in the Table below can be prepared according to one of the above-described processes according to the invention.

| No. | Compound | log P(pH 2.3) | m.p./° C. | R$_t$ (LC-MS)/min |
|---|---|---|---|---|
| 4 | H$_3$C—[pyrazole]—[pyrimidine]—S—CH$_2$CO$_2$Me | | 99 | |
| 5 | [pyrazole]—[pyrimidine]—S—CH$_2$CO$_2$Et | 2.19 | | |
| 6 | [furan]—[pyrazole]—[pyrimidine]—S—CH$_2$CO$_2$Me | | 120 | |
| 7 | Br—[pyrazole]—[pyrimidine]—S—CH$_2$CO$_2$Me | 2.69 | | |
| 8 | Cl—[phenyl]—[pyrazole]—[pyrimidine]—S—CH$_2$CO$_2$Et | 4.50 | | |
| 9 | F$_3$CS—[pyrazole(CH$_3$)]—[pyrimidine]—S—CH$_2$CO$_2$Et | 4.08 | | |

-continued
| No. | Compound | log P(pH 2.3) | m.p./° C. | R_t (LC-MS)/min |
|---|---|---|---|---|
| 10 | 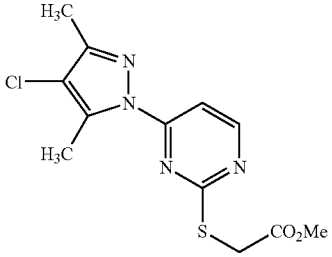 | | 113 | |
| 11 | 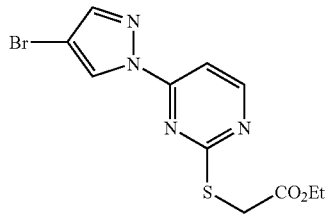 | | 70 | |
| 12 | 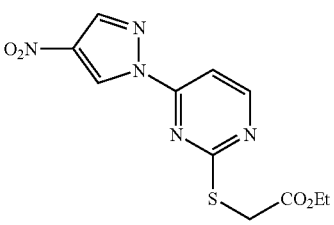 | 2.56 | | |
| 13 | 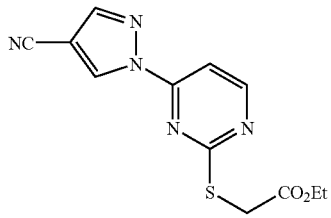 | 2.32 | | |
| 14 | 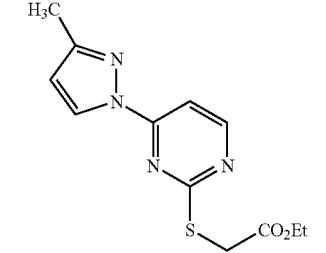 | 2.51 | | |
| 15 | 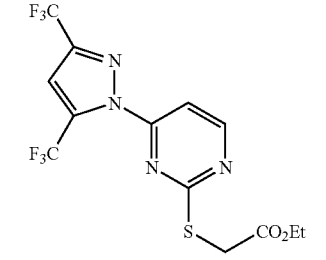 | 4.03 | | |

-continued

| No. | Compound | log P(pH 2.3) | m.p./° C. | R_t (LC-MS)/min |
|---|---|---|---|---|
| 16 | | 3.83 | | |
| 17 | | 3.64 | | |
| 18 | | 3.34 | | |
| 19 | | 3.01 | | |
| 20 | | 3.15 | oil | |
| 21 | | | 79 | |

-continued

| No. | Compound | log P(pH 2.3) | m.p./° C. | R$_t$ (LC-MS)/min |
|---|---|---|---|---|
| 22 | | 3.34 | | |
| 23 | | 3.11 | | |
| 24 | | | 63 | |
| 25 | | | 41 | |
| 26 | | | 48 | |
| 27 | | | 72 | |

-continued

| No. | Compound | log P(pH 2.3) | m.p./° C. | R_t (LC-MS)/min |
|---|---|---|---|---|
| 28 | pyrazolyl-pyrimidinyl-S-CH2-C(O)O-CH2CF2CHF2 | | 73 | |
| 29 | pyrazolyl-pyrimidinyl-S-CH2-C(O)O-CH2(CF2)2CF3 | | 51 | |
| 30 | pyrazolyl-pyrimidinyl-S-CH2-C(O)O-CH(CF3)2 | | 109 | |
| 31 | pyrazolyl-pyrimidinyl-S-CH2-C(O)O-CH(CH3)CF3 | | 41 | |
| 32 | pyrazolyl-pyrimidinyl-S-CH2-C(O)O-CH2CH2CF3 | | 86 | |
| 33 | pyrazolyl-pyrimidinyl-S-CH2-C(O)O-CH2CH2Cl | 2.30 | | |

-continued

| No. | Compound | log P(pH 2.3) | m.p./° C. | R_t (LC-MS)/min |
|---|---|---|---|---|
| 34 | pyrazolyl-pyrimidine-S-CH2-C(O)O-CH2CHCl2 | | 48 | |
| 35 | pyrazolyl-pyrimidine-S-CH2-C(O)O-CH2CCl3 | | 86 | |
| 36 | 4-methylpyrazolyl-pyrimidine-N(CH3)-CH2-CO2Et | | 61 | |
| 37 | 3-CF3-pyrazolyl-pyrimidine-S-CH2-CO2Et | | oil | |
| 38 | 3-acetylpyrazolyl-pyrimidine-S-CH2-CO2Et | | 91 | |
| 39 | 4-(4-trifluoromethoxyphenyl)-pyrazolyl-pyrimidine-S-CH2-C(O)O-CH2CH3 | | 94 | |

-continued

| No. | Compound | log P(pH 2.3) | m.p./° C. | R$_t$ (LC-MS)/min |
|---|---|---|---|---|
| 40 | (structure) | | 57 | |
| 41 | (structure) | 2.18 | 130 | |
| 42 | (structure) | | 124 | |
| 43 | (structure) | | 132 | |
| 44 | (structure) | | 69.5 | |
| 45 | (structure) | | 102–107 | |

-continued

| No. | Compound | log P(pH 2.3) | m.p./° C. | R_t (LC-MS)/min |
|---|---|---|---|---|
| 46 | | 2.53 | 66 | |
| 47 | | 2.79 | 67 | |
| 48 | | | 63 | |
| 49 | | | 65 | |
| 50 | | | 103 | |
| 51 | | 2.89 | 69 | |

-continued

| No. | Compound | log P(pH 2.3) | m.p./° C. | R$_t$ (LC-MS)/min |
|---|---|---|---|---|
| 52 | | | 112 | |
| 53 | | | 62 | |
| 54 | | | 79 | |
| 55 | | 2.99 | oil | |
| 56 | | | 132 (decomp) | |
| 57 | | | | 4,7 |

-continued

| No. | Compound | log P(pH 2.3) | m.p./° C. | R_t (LC-MS)/min |
|---|---|---|---|---|
| 58 | (pyrazol-1-yl)pyrimidin-2-yl-S-CH₂-C(O)-O-CH₂-C(F₂)-C(F₂)-CHF₂ | 3.42 | oil | |
| 59 | (pyrazol-1-yl)pyrimidin-2-yl-S-CH₂-C(O)-O-CH₂-(CF₂)₄-CF₃ | | 61 | |
| 60 | (pyrazol-1-yl)pyrimidin-2-yl-N(CH₃)-CH₂-C(O)-O-CH₂-C(F₂)-CF₃ | 3.2 | 47 | |
| 61 | (4-methoxy-pyrazol-1-yl)pyrimidin-2-yl-N(CH₃)-CH₂-COOH | 1.14 | 186 (decomp) | |
| 62 | (4-bromo-pyrazol-1-yl)pyrimidin-2-yl-N(CH₃)-CH₂-COOH | 1.91 | 211 (decomp) | |
| 63 | (4-chloro-pyrazol-1-yl)pyrimidin-2-yl-N(CH₃)-CH₂-COOH | 1.82 | | |

-continued

| No. | Compound | log P(pH 2.3) | m.p./° C. | R$_t$ (LC-MS)/min |
|---|---|---|---|---|
| 64 | | 3.27 | 90 | |
| 65 | | | 141 | |
| 66 | | | 189 | |
| 67 | | | 173 | |
| 68 | | | 140 | |
| 69 | | 3.57 | oil | |

-continued

| No. | Compound | log P(pH 2.3) | m.p./° C. | R_t (LC-MS)/min |
|---|---|---|---|---|
| 70 | | | 80 | |
| 71 | | | oil | |
| 72 | | | oil | |
| 73 | | 3.46 | oil | |
| 74 | | 2.71 | 104 | |
| 75 | | | 76 | |

-continued

| No. | Compound | log P(pH 2.3) | m.p./° C. | R$_t$ (LC-MS)/min |
|---|---|---|---|---|
| 76 | | 1.91 | | |
| 77 | | | 123 | |
| 78 | | | 72 | |
| 79 | | | 111 | |
| 80 | | | 75 | |

-continued

| No. | Compound | log P(pH 2.3) | m.p./° C. | R_t (LC-MS)/min |
|---|---|---|---|---|
| 81 | | | 105 (decomp) | |
| 82 | | 1.81 | 195 | |
| 83 | | 4.46 | 54 | |
| 84 | | 1.45 | 191 | |
| 85 | | | 81 | |
| 86 | | | | 4,2 |

-continued

| No. | Compound | log P(pH 2.3) | m.p./° C. | R$_t$ (LC-MS)/min |
|---|---|---|---|---|
| 87 | | | | 2,5 |
| 88 | | | 158 | |
| 89 | | | 75 | |
| 90 | | 4.34 | 68 | |
| 91 | | 3.78 | 89 | |

-continued

| No. | Compound | log P(pH 2.3) | m.p./° C. | R$_t$ (LC-MS)/min |
|---|---|---|---|---|
| 92 | | 4.3 | 85 | |
| 93 | | 4.14 | 67 | |
| 94 | | 4.73 | 85 | |
| 95 | | 2.07 | 130 | |
| 96 | | 2.87 | 60 | |
| 97 | | | 168 | |

-continued

| No. | Compound | log P(pH 2.3) | m.p./° C. | R$_t$ (LC-MS)/min |
|---|---|---|---|---|
| 98 | | | 205 | |
| 99 | | 0.94 | 90 | |
| 100 | | | 180 | |
| 101 | | 2.87 | 96 | |
| 102 | | 3.45 | 86 | |

The stated logp values were determined in accordance with EEC Directive 79/831 Annex V.A8 by HPLC (High Performance Liquid Chromatography) using a reversed-phase column (C 18). Temperature: 43° C.

Mobile phases for the determination in the acidic range: 0.1% aqueous phosphoric acid, acetonitrile; linear gradient from 10% acetonitrile to 90% acetonitrile.

Calibration was carried out using unbranched alkane-2-ones (having 3 to 16 carbon atoms) with known logp values (determination of the logp values by the retention times using linear interpolation between two successive alkanones).

The lambda max values were determined in the maxima of the chromatographic signals using the UV spectra from 200 nm to 400 nm.

HPLC-MS analysis is carried out under the following conditions:

| Method: | HPLC Chromatography using UV/DAD detectors and mass-sensitive detector with API interface (API = atmospheric pressure ionization). |
|---|---|
| Column: | Kromasil RP 18, 3.5 μm, length 23 mm, ID 3.1 mm. |
| Temperature: | 40° C. |
| Mobile phases: | A: Water with 0.08% formic acid |
| | B: Acetonitrile with 0.1% formic acid |
| Flow rate: | 2 ml/min; for mass spectrometry post-column split to 0.2 ml/min |
| Gradient: | 0 to 2.8 min: from 10% B to 95% B |
| | 2.8 to 4.0 min: 95% B |
| | 4.0 to 4.1 min: to 10% B |
| | 4.1 to 5.5 min: re-equilibration |

-continued

| Injection volume: | 3 μl |
|---|---|
| Detection: | UV/DAD: 210–270 nm |
| | MS: 100–1000 Da |

USE EXAMPLES

Example A

Meloidogyne Test

To produce a suitable preparation of active compound, 1 part by weight of active compound is mixed with the stated amounts of solvent and emulsifier, and the concentrate is diluted with water to the desired concentration.

Containers are filled with sand, solution of active compound, Meloidogyne incognita egg/larvae suspension and lettuce seeds. The lettuce seeds germinate and the plants develop. On the roots, galls are formed.

After the desired period of time, the nematicidal action is determined in % by the gall formation. 100% means that no galls were found; 0% means that the number of galls on the treated plants corresponds to that of the untreated control.

The amount of solvent, amount of emulsifier, active compounds, active compound concentrations and test results are shown in the Tables below.

TABLE A 1 plant-damaging insects
Meloidogyne Test
Solvent: 7 parts by weight of dimethylformamide
Emulsifier: 1 part by weight of alkylaryl polyglycol ether

| Active compounds | Concentration of active compound in ppm | Kill rate in % after 14[d] |
|---|---|---|
| 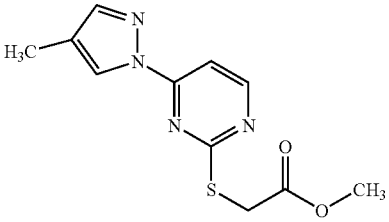 | 20 | 90 |

TABLE A 2 plant-damaging nematodes
Meloidogyne Test
Solvent: 7 parts by weight of dimethylformamide
Emulsifier: 2 parts by weight of alkylaryl polyglycol ether

| Active compounds | Concentration of active compound in ppm | Kill rate in % after 14[d] |
|---|---|---|
| 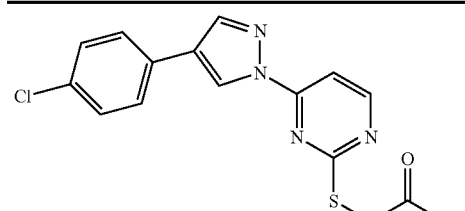 | 20 | 80 |

TABLE A 2-continued
plant-damaging nematodes
Meloidogyne Test
Solvent: 7 parts by weight of dimethylformamide
Emulsifier: 2 parts by weight of alkylaryl polyglycol ether
| Active compounds | Concentration of active compound in ppm | Kill rate in % after 14$^d$ |
|---|---|---|
| 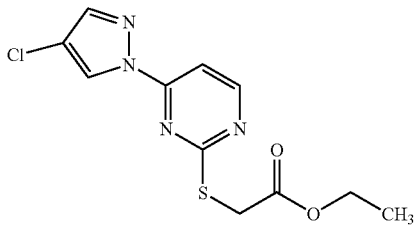 | 20 | 100 |
| 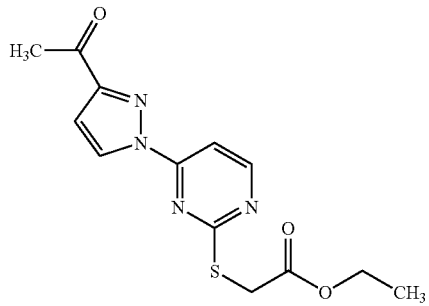 | 20 | 80 |
| 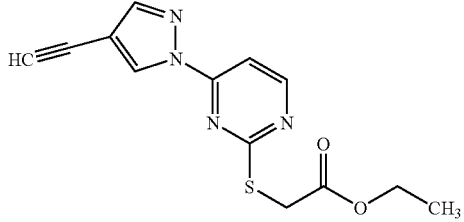 | 20 | 90 |
| 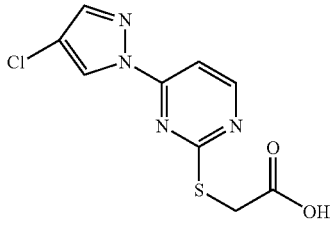 | 20 | 85 |
| 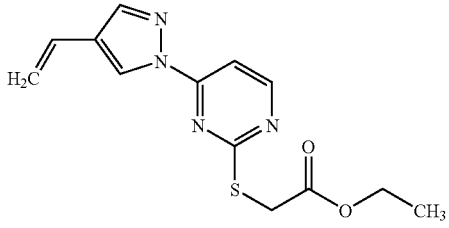 | 20 | 80 |

Example B

Myzus Test/Cabbage

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by peach aphids (*Myzus persicae*) are treated by being dipped into the preparation of active compound of the desired concentration.

After the desired period of time, the kill in % is determined. 100% means that all aphids have been killed; 0% means that none of the aphids have been killed.

Amounts of solvent, amounts of emulsifier, active compounds, active compound concentrations and test results are shown in the Tables below.

TABLE B 1 plant-damaging insects
Myzus Test/Cabbage
Solvent: 7 parts by weight of dimethylformamide
Emulsifier: 1 part by weight of alkylaryl polyglycol ether

| Active compounds | Concentration of active compound in ppm | Kill rate in % after $6^d$ |
|---|---|---|
| [structure: pyrazole-pyrimidine-S-CH2-C(O)-O-CH2CH3] | 500 | 95 |
| [structure: Br-pyrazole-pyrimidine-S-CH2-C(O)-O-CH2CH3] | 500 | 100 |

TABLE B 2 plant-damaging insects
Myzus Test/Cabbage
Solvent: 7 parts by weight of dimethylformamide
Emulsifier: 1 part by weight of alkylaryl polyglycol ether

| Active compounds | Concentration of active compound in ppm | Kill rate in % after $6^d$ |
|---|---|---|
| [structure: Cl-phenyl-pyrazole-pyrimidine-S-CH2-C(O)-O-CH2CH3] | 500 | 100 |

TABLE B 2-continued
plant-damaging insects
Myzus Test/Cabbage
Solvent: 7 parts by weight of dimethylformamide
Emulsifier: 1 part by weight of alkylaryl polyglycol ether
| Active compounds | Concentration of active compound in ppm | Kill rate in % after 6$^d$ |
|---|---|---|
| 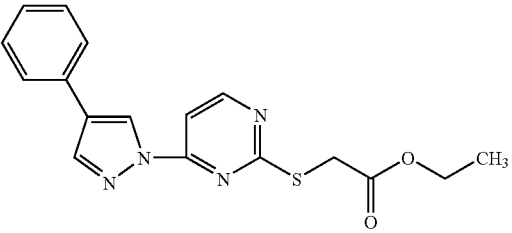 | 500 | 100 |
| 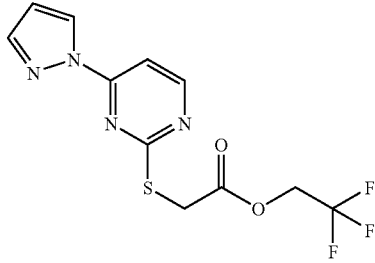 | 500 | 100 |
| 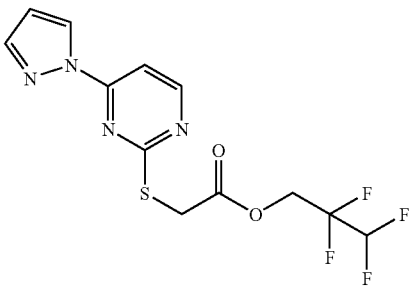 | 500 | 100 |
| 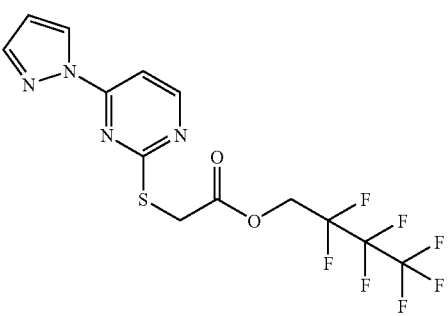 | 500 | 100 |
| 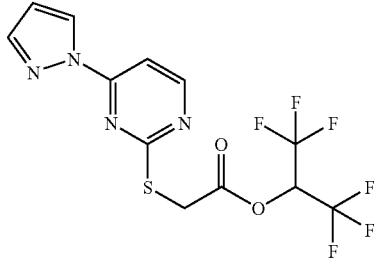 | 500 | 100 |

TABLE B 2-continued
plant-damaging insects
Myzus Test/Cabbage
Solvent: 7 parts by weight of dimethylformamide
Emulsifier: 1 part by weight of alkylaryl polyglycol ether
| Active compounds | Concentration of active compound in ppm | Kill rate in % after 6$^d$ |
|---|---|---|
| 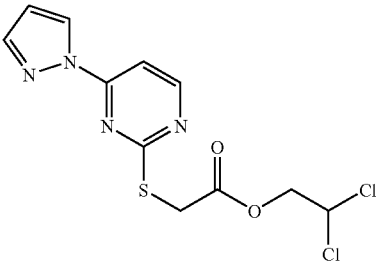 | 500 | 100 |
| 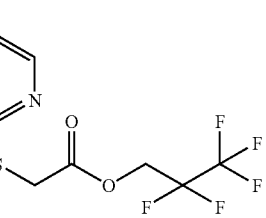 | 500 | 100 |
| 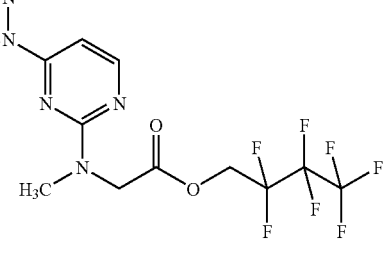 | 500 | 100 |
| 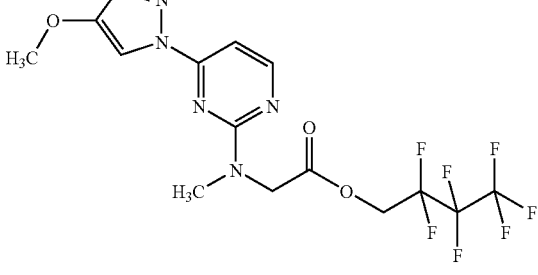 | 500 | 100 |
| 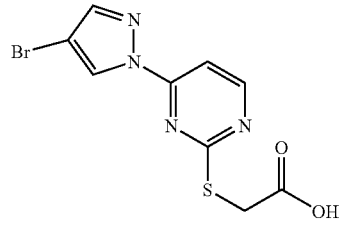 | 500 | 100 |

TABLE B 2-continued plant-damaging insects
Myzus Test/Cabbage
Solvent: 7 parts by weight of dimethylformamide
Emulsifier: 1 part by weight of alkylaryl polyglycol ether

| Active compounds | Concentration of active compound in ppm | Kill rate in % after 6$^d$ |
|---|---|---|
| (structure) | 500 | 100 |
| (structure) | 500 | 100 |
| (structure) | 500 | 100 |
| (structure) | 500 | 100 |
| (structure) | 500 | 100 |

TABLE B 2-continued plant-damaging insects
Myzus Test/Cabbage
Solvent: 7 parts by weight of dimethylformamide
Emulsifier: 1 part by weight of alkylaryl polyglycol ether

| Active compounds | Concentration of active compound in ppm | Kill rate in % after $6^d$ |
|---|---|---|
| [structure: methoxy-pyrazole-pyrimidine-S-CH2-C(O)O-CH(CH3)-perfluorobutyl] | 500 | 100 |
| [structure: bromo-pyrazole-pyrimidine-S-CH2-C(O)O-CH(CH3)-perfluorobutyl] | 500 | 100 |

Example C

Myzus Test/Broad Beans

| Solvent: | 31 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with emulsifier-containing water to the desired concentrations.

Broad bean (*Vicia faba* minor) seedlings which are infested by green peach aphids (*Myzus persicae*) are dipped into a preparation of active compound of the desired concentration and placed into a plastic box.

After the desired period of time, the kill in % is determined. 100% means that all animals have been killed; 0% means that none of the animals have been killed.

Active compounds, active compound concentrations and test results are shown in the Table below.

TABLE C plant-damaging insects
Myzus Test/Broad beans
Solvent: 31 parts by weight of acetone
Emulsifier: 1 part by weight of alkylaryl polyglycol ether

| Active compounds | Concentration of active compound in ppm | Kill rate in % after $6^d$ |
|---|---|---|
| [structure: methyl-pyrazole-pyrimidine-S-CH2-C(O)O-CH3] | 500 | 100 |

TABLE C-continued plant-damaging insects
Myzus Test/Broad beans
Solvent: 31 parts by weight of acetone
Emulsifier: 1 part by weight of alkylaryl polyglycol ether

| Active compounds | Concentration of active compound in ppm | Kill rate in % after $6^d$ |
|---|---|---|
| 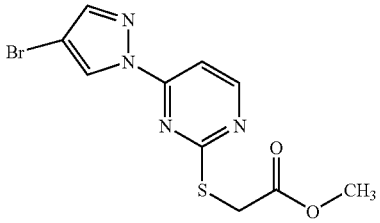 | 100 | 100 |
| 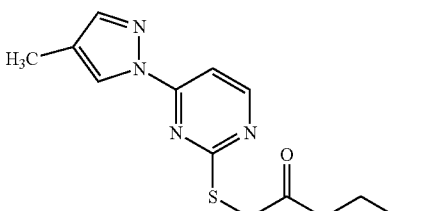 | 500 | 99 |

Example D

Critical Concentration/Root-systemic Action

| | |
|---|---|
| Test insect: | Aphis gossypii |
| Solvent: | 4 parts by weight of acetone |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is transferred into pots and these are planted with cucumber plants at the cotyledon stage. In this way, the active compound can be taken up from the plant and be transported into the leaves.

To demonstrate the root-systemic effect, the leaves are populated with the abovementioned test animals after 7 days. After a further 7 days, evaluation is carried out by counting or estimating the dead animals. The root-systemic action of the active compound is deduced from the mortality figures. It is 100% if all test animals have been killed and 0% if just as many test insects are still alive as in the case of the untreated controls.

Active compounds, active compound concentration and test results are shown in the Table below.

TABLE D plant-damaging insects
Aphis gossypii/root-systemic action
Test insect: Aphis gossypii
Solvent: 4 parts by weight of acetone
Emulsifier: 1 part by weight of alkylaryl polyglycol ether

| Active compounds | Concentration of active compound in ppm | Kill rate in % $7^d$ after infection |
|---|---|---|
| 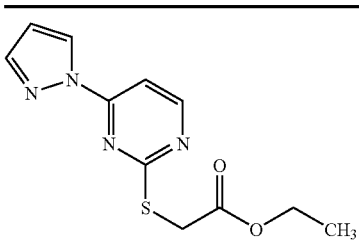 | 20 | 90 |

Example E

*Aphis gossypii* Test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

Active compounds, active compound concentration and test results are shown in the Table below.

TABLE E plant-damaging insects
Aphis gossypii Test
Solvent: 7 parts by weight of dimethylformamide
Emulsifier: 2 parts by weight of alkylaryl polyglycol ether

| Active compounds | Concentration of active compound in ppm | Kill rate in % after $6^d$ |
|---|---|---|
| 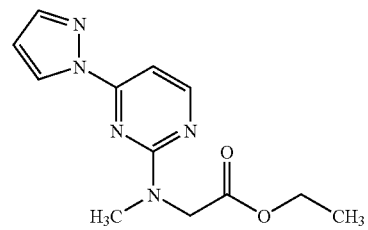 | 500 | 99 |
| 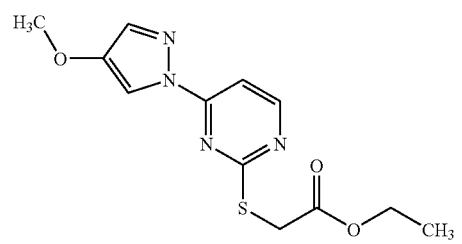 | 500 | 95 |
| 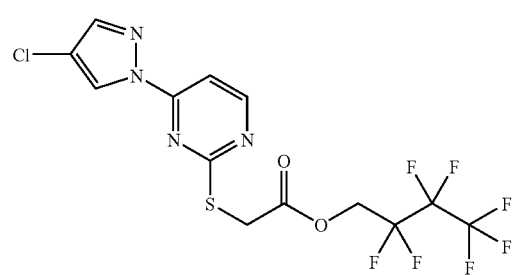 | 500 | 99 |
| 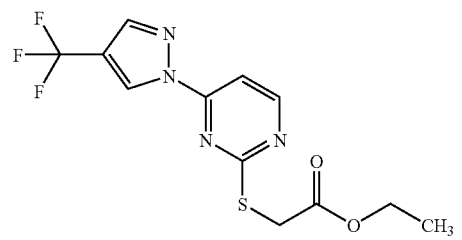 | 500 | 95 |
| 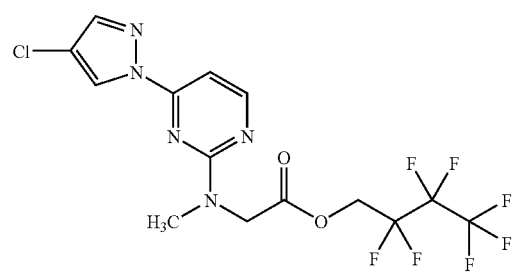 | 500 | 95 |

TABLE E-continued plant-damaging insects
Aphis gossypii Test
Solvent: 7 parts by weight of dimethylformamide
Emulsifier: 2 parts by weight of alkylaryl polyglycol ether

| Active compounds | Concentration of active compound in ppm | Kill rate in % after 6$^d$ |
|---|---|---|
| [structure: H$_3$C-O-pyrazole-pyrimidine-S-CH$_2$-C(O)-OH] | 500 | 90 |
| [structure: Cl-pyrazole-pyrimidine-S-CH$_2$-C(O)-O-CH(CH$_3$)-C$_4$F$_7$] | 500 | 90 |
| [structure: H$_3$C-O-pyrazole-pyrimidine-S-CH$_2$-C(O)-O-CH$_2$-CF$_3$] | 500 | 100 |
| [structure: CHF$_2$-CF$_2$-S-pyrazole-pyrimidine-S-CH$_2$-C(O)-O-CH$_3$] | 500 | 90 |

Example F

Phaedon Larvae Test

| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochlearae*) while the leaves are still moist.

After the desired period of time, the kill in % is determined. 100% means that all beetle larvae have been killed; 0% means that none of the beetle larvae have been killed.

Active compounds, active compound concentration and test results are shown in the Table below.

TABLE F plant-damaging insects
Phaedon Larvae Test
Solvent: 7 parts by weight of dimethylformamide
Emulsifier: 2 parts by weight of alkylaryl polyglycol ether

| Active compounds | Concentration of active compound in ppm | Kill rate in % after 7$^d$ |
|---|---|---|
| 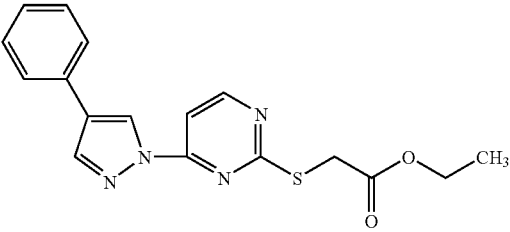 | 500 | 100 |
| 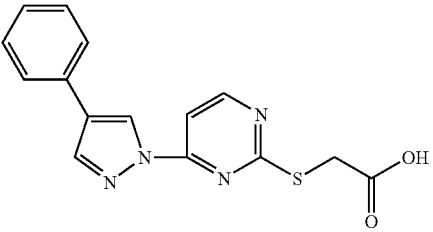 | 500 | 100 |

Example G

*Diabrotica balteata* Test (Larvae in Soil)

Critical Concentration Test/Soil Insects—Treatment of Transgenic Plants

| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually irrelevant, only the amount by weight of active compound per volume unit of soil, which is stated in ppm (mg/l), being decisive. The soil is filled into 0.25 l pots and these are allowed to stand at 20° C.

Immediately after preparation, 5 pre-germinated maize corns of the cultivar YIELD GUARD (trademark of Monsanto Comp., USA) are placed into each pot. After 2 days, the test insects in question are placed into the treated soil. After a further 7 days, the efficacy of the active compound is determined by counting the maize plants that have emerged (1 plant=20% efficacy).

Example H

*Heliothis virescens* Test (Treatment of Transgenic Plants)

| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soja bean shoots (*Glycine max*) of the cultivar Roundup Ready (trademark of Monsanto Comp. USA) are treated by being dipped into the preparation of active compound of the desired concentration and are populated with the tobacco bud worm *Heliothis virescens* while the leaves are still moist.

After the desired period of time, the kill in % is determined. 100% means that all caterpillars have been killed; 0% means that none of the caterpillars have been killed.

What is claimed is:

1. A pyrazolylpyrimidine of formula (I)

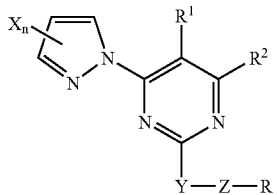

in which

R¹ and R² independently of one another represent hydrogen, halogen, nitro, cyano, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R³, —NR⁴R⁵, —COR⁶, —CO₂R⁷, —CSR⁶, —CONR⁴R⁵, —NHCO₂R⁸, or cycloalkyl; or represent aryl, arylalkyl, or saturated or unsaturated heterocyclyl having 1 to 4 heteroatoms selected from the group consisting of nitrogen, oxygen, and sulphur, each of which radicals is optionally substituted by substituents from the group consisting of halogen, alkyl, halogenoalkyl, alkoxy, and halogenoalkoxy, or R¹ and R² together represent alkylene or alkenylene, where the carbon chain is optionally interrupted by 1 to 3 heteroatoms selected from the group consisting of nitrogen and oxygen and where the resulting ring is optionally substituted by halogen or alkyl, X represents halogen, nitro, cyano, hydroxyl, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R³, —SO₂NR⁴R⁵, —NR⁴R⁵, —COR⁶, —CO₂R⁷, —CSR⁶, —CONR⁴R⁵, —NHCO₂R⁸, or cycloalkyl; or represents aryl, arylalkyl, or saturated or unsaturated heterocyclyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, and halogenoalkoxy; or, when n represents 2 or 3, two adjacent X together optionally represent alkylene or alkenylene, where the carbon chain is optionally interrupted by 1 or 2 heteroatoms selected from the group consisting of nitrogen and oxygen, n represents 0, 1, 2, or 3, where X represents identical or different radicals when n represents 2 or 3, Y represents a direct bond, oxygen, —S(O)$_p$—, or —NR⁹—, p represents 0, 1, or 2, Z represents —(CH₂)$_r$—, —(CH₂)$_t$—(CHR¹⁰)—(CH₂)$_w$—, —(CH₂)$_r$—C(O)—(CH₂)$_t$—, —(CH₂)$_r$—O—(CH₂)$_t$—, —(CH₂)$_r$—S(O)$_p$—(CH₂)$_t$—, —(CH₂)$_t$—N(R¹¹)—(CH₂)$_t$—, or —(CH₂)$_t$—C(R¹²)=C(R¹³)—(CH₂)$_w$—, r represents 1, 2, 3, 4, 5, or 6, t and w independently of one another represent 0, 1, 2, 3, or 4, R represents a carboxylic acid bioisostere (acid mimic) selected from the group consisting of

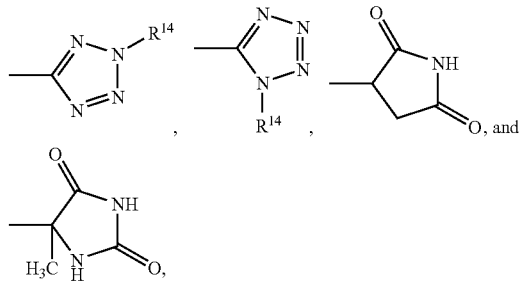

R³ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, R⁴ represents hydrogen, alkyl, halogenoalkyl, cycloalkyl, or alkylcarbonyl, R⁵ represents hydrogen, amino, formyl, alkyl, alkenyl, alkynyl, halogenoalkyl, cycloalkyl, alkoxy, alkoxyalkyl, alkylcarbonyl, alkoxycarbonyl, and oxamoyl, or R⁴ and R⁵ together represent alkylidene; or represent optionally halogen-, nitro-, alkyl-, or halogenoalkyl-substituted benzylidene; or R⁴ and R⁵ together with the nitrogen atom to which they are attached form a saturated or unsaturated heterocycle that optionally contains a further nitrogen, oxygen, or sulphur atom and that is optionally substituted by alkyl, R⁶ represents hydrogen, alkyl, halogenoalkyl, or arylalkyl, R⁷ represents hydrogen, alkyl, halogenoalkyl, cycloalkyl, cycloalkylalkyl, aryl, or arylalkyl, R⁸ represents alkyl or halogenoalkyl, R⁹ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, R¹⁰ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R¹¹ represents hydrogen or alkyl, R¹² and R¹³ independently of one another represent hydrogen, hydroxyl, alkyl, or alkoxy, and R¹⁴ represents hydrogen, alkyl, or halogenoalkyl.

2. A pyrazolylpyrimidine of formula (I) according to claim 1 in which

R¹ and R² independently of one another represent hydrogen, halogen, nitro, cyano, C₁–C₆-alkyl, C₁–C₆-halogenoalkyl, C₁–C₆-alkoxy, C₁–C₆-halogenoalkoxy, C₂–C₆-alkenyl, C₂–C₆-alkynyl, C₂–C₆-alkenyloxy, C₂–C₆-halogenoalkenyloxy, C₂–C₆-alkynyloxy, C₂–C₆-halogenoalkynyloxy, —S(O)$_p$R³, —NR⁴R⁵, —COR⁶, —CO₂R⁷, —CSR⁶, —CONR⁴R⁵, —NHCO$_2$R$^8$, or C$_3$–C$_7$-cycloalkyl; or represent aryl, aryl-C$_1$–C$_6$-alkyl, or 5- or 6-membered saturated or unsaturated heterocyclyl having 1 to 4 heteroatoms that contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, C$_1$–C$_6$-alkyl, C$_1$–C$_6$-halogenoalkyl, C$_1$–C$_6$-alkoxy, and C$_1$–C$_6$-halogenoalkoxy; or R$^1$ and R$^2$ together represent C$_3$–C$_5$-alkylene or C$_3$–C$_4$-alkenylene, where the carbon chain is optionally interrupted by 1 or 2 heteroatoms that are 0 to 2 nitrogen atoms and/or 0 or 1 oxygen atom, and where the resultant ring is optionally mono- or polysubstituted by identical or different substituents selected from the group consisting of halogen and C$_1$–C$_6$-alkyl;

X represents halogen, nitro, cyano, hydroxyl, C$_1$–C$_6$-alkyl, C$_1$–C$_6$-halogenoalkyl, C$_1$–C$_6$-alkoxy, C$_1$–C$_6$-halogenoalkoxy, C$_2$–C$_6$-alkenyl, C$_2$–C$_6$-alkynyl, C$_2$–C$_6$-alkenyloxy, C$_2$–C$_6$-halogenoalkenyloxy, C$_2$–C$_6$-alkynyloxy, C$_2$–C$_6$-halogenoalkynyloxy, —S(O)$_p$R$^3$, —SO$_2$NR$^4$R$^5$, —NR$^4$R$^5$, —COR$^6$, —CO$_2$R$^7$, —CSR$^6$, —CONR$^4$R$^5$, —NHCO$_2$R$^8$, or C$_3$–C$_7$-cycloalkyl; or represents aryl, aryl-C$_1$–C$_6$-alkyl, or 5- or 6-membered saturated or unsaturated heterocyclyl having 1 to 4 heteroatoms that contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, C$_1$–C$_6$-alkyl, C$_1$–C$_6$-halogenoalkyl, C$_1$–C$_6$-alkoxy, and C$_1$–C$_6$-halogenoalkoxy; or, when n represents 2 or 3, two adjacent radicals X together optionally represent C$_3$–C$_5$-alkylene or C$_3$–C$_4$-alkenylene, where the carbon chain is optionally interrupted by 1 or 2 heteroatoms that are 0 to 2 nitrogen atoms and/or 0 or 1 oxygen atom;

n represents 0, 1, 2 or 3, where X represents identical or different radicals when n represents 2 or 3;

Y represents a direct bond, oxygen, —S(O)$_p$—, or —NR$^9$—, p represents 0, 1, or 2;

Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)═C(R$^{13}$)—(CH$_2$)$_w$—, r represents 1, 2, 3, 4, 5, or 6;

t and w independently of one another represent 0, 1, 2, 3, or 4;

R represents a carboxylic acid bioisostere (acid mimic) selected from the group consisting of

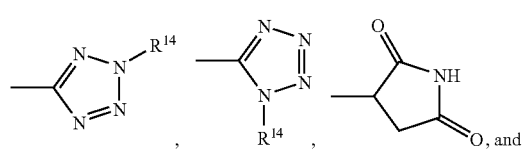

-continued

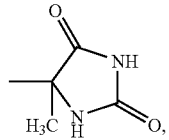

R$^3$ represents hydrogen, C$_1$–C$_6$-alkyl, C$_1$–C$_6$-halogenoalkyl, C$_3$–C$_7$-cycloalkyl, or C$_3$–C$_7$-cycloalkyl-C$_1$–C$_6$-alkyl; or represents aryl, aryl-C$_1$–C$_6$-alkyl, or 5- or 6-membered saturated or unsaturated heterocyclyl or heterocyclyl-C$_1$–C$_6$-alkyl having 1 to 4 heteroatoms that contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, and C$_1$–C$_6$-halogenoalkylthio;

R$^4$ represents hydrogen, C$_1$–C$_6$-alkyl, C$_1$–C$_6$-halogenoalkyl, C$_3$–C$_7$-cycloalkyl, or C$_1$–C$_6$-alkylcarbonyl;

R$^5$ represents hydrogen, amino, formyl, C$_1$–C$_6$-alkyl, C$_2$–C$_6$-alkenyl, C$_2$–C$_6$-alkynyl, C$_1$–C$_6$-halogenoalkyl, C$_3$–C$_7$-cycloalkyl, C$_1$–C$_6$-alkoxy, C$_1$–C$_6$-alkoxy-C$_1$–C$_6$-alkyl, C$_1$–C$_6$-alkylcarbonyl, C$_1$–C$_6$-alkoxycarbonyl, or oxamoyl; or R$^4$ and R$^5$ together represent C$_1$–C$_6$-alkylidene; or represent benzylidene that is optionally mono- or polysubstituted by identical or different substituents selected from the group consisting of halogen, nitro, C$_1$–C$_6$-alkyl, and C$_1$–C$_6$-halogenoalkyl; or R$^4$ and R$^5$ together with the nitrogen atom to which they are attached represent a 5- or 6-membered saturated or unsaturated heterocycle that optionally contains a further nitrogen, oxygen, or sulphur atom and that is optionally mono- or polysubstituted by identical or different C$_1$–C$_6$-alkyl;

R$^6$ represents hydrogen, C$_1$–C$_6$-alkyl, C$_1$–C$_6$-halogenoalkyl, or aryl-C$_1$–C$_6$-alkyl;

R$^7$ represents hydrogen, C$_1$–C$_6$-alkyl, C$_1$–C$_6$-halogenoalkyl, C$_3$–C$_7$-cycloalkyl, C$_3$–C$_7$-cycloalkyl-C$_1$–C$_6$-alkyl, aryl, or aryl-C$_1$–C$_6$-alkyl;

R$^8$ represents C$_1$–C$_6$-alkyl or C$_1$–C$_6$-halogenoalkyl;

R$^9$ represents hydrogen, C$_1$–C$_6$-alkyl, C$_1$–C$_6$-halogenoalkyl, C$_3$–C$_7$-cycloalkyl, or C$_3$–C$_7$-cycloalkyl-C$_1$–C$_6$-alkyl; or represents aryl, aryl-C$_1$–C$_6$-alkyl, or 5- or 6-membered saturated or unsaturated heterocyclyl or heterocyclyl-C$_1$–C$_6$-alkyl having 1 to 4 heteroatoms that are 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, and C$_1$–C$_6$-halogenoalkylthio;

R$^{10}$ represents halogen, C$_1$–C$_6$-alkyl, C$_1$–C$_6$-alkylcarbonyl, C$_1$–C$_6$-alkoxycarbonyl, C$_3$–C$_7$-cycloalkyl, or C$_3$–C$_7$-cycloalkyl-C$_1$–C$_6$-alkyl; or represents aryl or aryl-C$_1$–C$_6$-alkyl that is optionally mono- or polysubstituted in the aryl moiety by identical or different substituents selected from the group consisting of halogen and C$_1$–C$_6$-alkyl;

R$^{11}$ represents hydrogen or C$_1$–C$_6$-alkyl;

R¹² and R¹³ independently of one another represent hydrogen, hydroxyl, $C_1$–$C_6$-alkyl, or $C_1$–$C_6$-alkoxy; and R¹⁴ represents hydrogen, $C_1$–$C_6$-alkyl, or $C_1$–$C_6$-halogenoalkyl.

3. A pyrazolylpyrimidine of formula (I) according to claim 1

R¹ and R² independently of one another represent hydrogen, fluorine, chlorine, bromine, nitro, cyano, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_2$–$C_4$-alkenyl, $C_2$–$C_4$-alkynyl, —S(O)$_p$R³, —NR⁴R⁵, —COR⁶, —CO₂R⁷, —CSR⁶, —CONR⁴R⁵, —NHCO₂R⁸, or $C_3$–$C_6$-cycloalkyl; or represent aryl aryl-$C_1$–$C_4$-alkyl, or 5- or 6-membered saturated or unsaturated heterocyclyl having 1 to 3 heteroatoms that are 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy and $C_1$–$C_4$-halogenoalkoxy having 1 to 9 fluorine, chlorine, and/or bromine atoms; or R¹ and R² together represent $C_3$–$C_5$-alkylene or $C_3$–$C_4$-alkenylene, where the carbon chain is optionally interrupted by 1 or 2 heteroatoms that are 0 to 2 nitrogen atoms and/or 0 or 1 oxygen atom, and where the resultant ring is optionally mono- to tetrasubstituted by identical or different substituents selected from the group consisting of fluorine, chlorine, bromine, and $C_1$–$C_4$-alkyl;

X represents fluorine, chlorine, bromine, iodine, nitro, cyano, hydroxyl, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_2$–$C_4$-alkenyl, $C_2$–$C_4$-alkynyl, —S(O)$_p$R³, —SO₂NR⁴R⁵, —NR⁴R⁵, —COR⁶, —CO₂R⁷, —CSR⁶, —CONR⁴R⁵, —NHCO₂R⁸, or $C_3$–$C_6$-cycloalkyl; or represents aryl, aryl-$C_1$–$C_4$-alkyl, 5- or 6-membered saturated or unsaturated heterocyclyl having 1 to 3 heteroatoms that are 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, and $C_1$–$C_4$-halogenoalkoxy having 1 to 9 fluorine, chlorine, and/or bromine atoms; or, when n represents 2 or 3, two adjacent radicals X together optionally represent $C_3$–$C_4$-alkylene or $C_3$–$C_4$-alkenylene, where the carbon chain may be interrupted by 1 or 2 heteroatoms, which may be 0 to 2 nitrogen atoms, and/or 0 or 1 oxygen atom;

n represents 0, 1, 2, or 3, where X represents identical or different radicals when n represents 2 or 3;

Y represents a direct bond, oxygen, —S(O)$_p$—, or —NR⁹—, p represents 0, 1, or 2;

Z represents —(CH₂)$_r$—, —(CH₂)$_r$—(CHR¹⁰)—(CH₂)$_w$—, —(CH₂)$_r$—C(O)—(CH₂)$_t$—, —(CH₂)$_r$—O—(CH₂)$_t$—, —(CH₂)$_r$—S(O)$_p$—(CH₂)$_t$—, —(CH₂)$_r$—N(R¹¹)—(CH₂)$_t$—, or —(CH₂)$_t$—C(R¹²)=C(R¹³)—(CH₂)$_w$—, r represents 1, 2, 3, or 4;

t and w independently of one another represent 0, 1, 2, 3, or 4;

R represents a carboxylic acid bioisostere (acid mimic) selected from the group consisting of

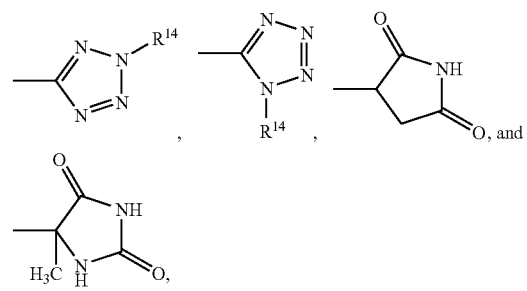

R³ represents hydrogen, $C_1$–$C_4$-alkyl, $C_1$–$C_4$-halogenoalkyl having 1 to 9 fluorine, chlorine, and/or bromine atoms, $C_3$–$C_6$-cycloalkyl, or $C_3$–$C_6$-cycloalkyl-$C_1$–$C_4$-alkyl; or represents aryl (in particular phenyl), aryl-$C_1$–$C_4$-alkyl, 5- or 6-membered saturated or unsaturated heterocyclyl or heterocyclyl-$C_1$–$C_4$-alkyl having 1 to 3 heteroatoms, which contains 0 to 3 nitrogen atoms, 0 to 2 nonadjacent oxygen atoms and/or 0 to 2 nonadjacent sulphur atoms, each of which radicals is optionally mono- to tetrasubstituted by identical or different radicals selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, and $C_1$–$C_4$-halogenoalkylthio having 1 to 9 fluorine, chlorine, and/or bromine atoms;

R⁴ represents hydrogen, $C_1$–$C_4$-alkyl, $C_1$–$C_4$-halogenoalkyl having 1 to 9 fluorine, chlorine, and/or bromine atoms, $C_3$–$C_6$-cycloalkyl, or $C_1$–$C_4$-alkylcarbonyl;

R⁵ represents hydrogen, amino, formyl, $C_1$–$C_4$-alkyl, $C_2$–$C_4$-alkenyl, $C_2$–$C_4$-alkynyl, $C_1$–$C_4$-halogenoalkyl having 1 to 9 fluorine, chlorine, and/or bromine atoms, $C_3$–$C_6$-cycloalkyl, $C_1$–$C_4$-alkoxy, $C_1$–$C_4$-alkoxy-$C_1$–$C_4$-alkyl, $C_1$–$C_4$-alkylcarbonyl, $C_1$–$C_4$-alkoxycarbonyl, or oxamoyl; or R⁴ and R⁵ together represent $C_1$–$C_4$-alkylidene; or represent benzylidene that is optionally mono- to tetrasubstituted by identical or different substituents selected from the group consisting of fluorine, chlorine, bromine, nitro, $C_1$–$C_4$-alkyl, and $C_1$–$C_4$-halogenoalkyl having 1 to 9 fluorine, chlorine, and/or bromine atoms; or R⁴ and R⁵ together with the nitrogen atom to which they are attached represent a 5- or 6-membered saturated or unsaturated heterocycle that optionally contains a further nitrogen, oxygen, or sulphur atom and that is optionally mono- to tetrasubstituted by identical or different $C_1$–$C_4$-alkyl;

R⁶ represents hydrogen, $C_1$–$C_4$-alkyl, $C_1$–$C_4$-halogenoalkyl having 1 to 9 fluorine, chlorine, and/or bromine atoms, or aryl-$C_1$–$C_4$-alkyl;

$R^7$ represents hydrogen, $C_1$–$C_4$-alkyl, $C_1$–$C_4$-halogenoalkyl having 1 to 9 fluorine, chlorine, and/or bromine atoms, $C_3$–$C_6$-cycloalkyl, $C_3$–$C_6$-cycloalkyl-$C_1$–$C_4$-alkyl, aryl, or aryl-$C_1$–$C_4$-alkyl;

$R^8$ represents $C_1$–$C_4$-alkyl or $C_1$–$C_4$-halogenoalkyl having 1 to 9 fluorine, chlorine, and/or bromine atoms;

$R^9$ represents hydrogen, $C_1$–$C_4$-alkyl, $C_1$–$C_4$-halogenoalkyl having 1 to 9 fluorine, chlorine, and/or bromine atoms, $C_3$–$C_6$-cycloalkyl, or $C_3$–$C_6$-cycloalkyl-$C_1$–$C_4$-alkyl; or represents aryl, aryl-$C_1$–$C_4$-alkyl, or 5- or 6-membered saturated or unsaturated heterocyclyl or heterocyclyl-$C_1$–$C_4$-alkyl having in each case 1 to 3 heteroatoms that are 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, or $C_1$–$C_4$-halogenoalkylthio having 1 to 9 fluorine, chlorine, and/or bromine atoms;

$R^{10}$ represents fluorine, chlorine, bromine, iodine, $C_1$–$C_4$-alkyl, $C_1$–$C_4$-alkylcarbonyl, $C_1$–$C_4$-alkoxycarbonyl, $C_3$–$C_6$-cycloalkyl, or $C_3$–$C_6$-cycloalkyl-$C_1$–$C_4$-alkyl; or represents aryl or aryl-$C_1$–$C_4$-alkyl, each of which radicals is optionally mono- to tetrasubstituted in the aryl moiety by identical or different substituents selected from the group consisting of fluorine, chlorine, bromine, and $C_1$–$C_4$-alkyl;

$R^{11}$ represents hydrogen or $C_1$–$C_4$-alkyl;

$R^{12}$ and $R^{13}$ independently of one another represent hydrogen, hydroxyl, $C_1$–$C_4$-alkyl, or $C_1$–$C_4$-alkoxy; and $R^{14}$ represents hydrogen, $C_1$–$C_4$-alkyl, or $C_1$–$C_4$-halogenoalkyl having 1 to 9 fluorine, chlorine, and/or bromine atoms.

4. A pyrazolylpyrimidine of formula (I) according to claim 3 in which one or both of $R^1$ and $R^2$ independently represent phenyl that is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy and $C_1$–$C_4$-halogenoalkoxy having 1 to 9 fluorine, chlorine, and/or bromine atoms.

5. A pyrazolylpyrimidine of formula (I) according to claim 3 in which X represents one or more phenyl that is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, and $C_1$–$C_4$-halogenoalkoxy having 1 to 9 fluorine, chlorine, and/or bromine atoms.

6. A pyrazolylpyrimidine of formula (I) according to claim 3 in which $R^3$ represents phenyl that is optionally mono- to tetrasubstituted by identical or different radicals selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, and $C_1$–$C_4$-halogenoalkylthio having 1 to 9 fluorine, chlorine, and/or bromine atoms.

7. A pyrazolylpyrimidine of formula (I) according to claim 3 in which $R^7$ represents phenyl.

8. A pyrazolylpyrimidine of formula (I) according to claim 3 in which $R^9$ represents phenyl that is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, or $C_1$–$C_4$-halogenoalkylthio having 1 to 9 fluorine, chlorine, and/or bromine atoms.

9. A pyrazolylpyrimidine of formula (I) according to claim 3 in which $R^{10}$ represents phenyl that is optionally mono- to tetrasubstituted by identical or different substituents selected from the group consisting of fluorine, chlorine, bromine, and $C_1$–$C_4$-alkyl.

10. A pyrazolylpyrimidine of formula (I) according to claim 1 in which $R^1$ and $R^2$ independently of one another represent hydrogen, fluorine, chlorine, bromine, nitro, cyano, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, methoxy, ethoxy, n-propoxy, isopropoxy, n-butoxy, isobutoxy, sec-butoxy, tert-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, —$COMe$, —$CO_2Me$, —$CO_2Et$, amino, cyclopentyl, or cyclohexyl; or represent phenyl, benzyl, pyridinyl, or furyl, each of which is optionally mono- to trisubstituted by identical or different substituents selected from the group consisting of fluorine, chlorine, bromine, methyl, ethyl, methoxy, ethoxy, trifluoromethyl, and trifluoromethoxy; or $R^1$ and $R^2$ together represent propylene, butylene, propenylene, butadienylene, —$(CH_2)_2$—O—$CH_2$—, —$(CH_2)_2$—NH—$CH_2$—, —CH=CH—N=CH—, or —CH=CCl—CH=CH—;

X represents fluorine, chlorine, bromine, iodine, nitro, cyano, hydroxyl, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, methoxy, ethoxy, n-propoxy, isopropoxy, n-butoxy, isobutoxy, sec-butoxy, tert-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, vinyl, ethynyl, —$SO_2NH_2$, —$SO_2NHMe$, —$SO_2NMe_2$, amino, —NHMe, —$NMe_2$, —CHO, —COMe, —$CO_2Me$, —$CO_2Et$, —$CONH_2$, —CONHMe, —$CONMe_2$, —NHCOMe, cyclopentyl, or cyclohexyl; or represents phenyl, benzyl, furyl, thienyl, pyrrolyl, oxazolyl, isoxazyl, imidazyl, pyrazyl, thiazolyl, pyridyl, pyrimidinyl, pyridazyl, triazinyl, or triazyl, each of which is optionally mono- to trisubstituted by identical or different substituents selected from the group consisting of fluorine, chlorine, bromine, methyl, ethyl, methoxy, ethoxy, trifluoromethyl, and trifluoromethoxy; or, when n represents 2 or 3, two adjacent radicals X together optionally represent propylene, butylene, propenylene, butadienylene, —$(CH_2)_2$—O—$CH_2$—, —$(CH_2)_2$—NH—$CH_2$—, or —CH=CH—N=CH—;

n represents 0, 1, 2, or 3, where X represents identical or different radicals when n represents 2 or 3;

Y represents a direct bond, oxygen, —$S(O)_p$—, or —$NR^9$—, p represents 0, 1, or 2;

Z represents —$CH_2$—, —$(CH_2)_2$—, —$(CH_2)_3$—, —$(CH_2)_4$—, —$(CHR^{10})$—, —$CH_2$—C(O)—$CH_2$—, —CH$_2$—NH—, —CH=CH—, —CH$_2$—CH=CH—, —CH=C(OH)—, —OH=C(OMe)—, or —CH$_2$—C(OMe)=OH—;

R represents a carboxylic acid bioisostere (acid mimic) selected from the group consisting of

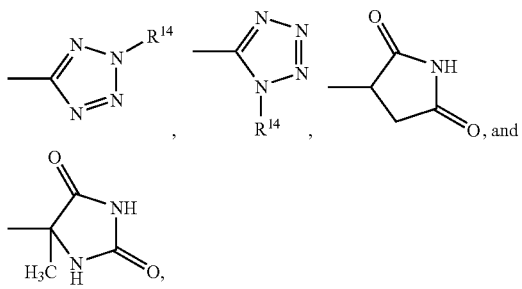

R$^4$ represents hydrogen, methyl, ethyl, n-propyl, isopropyl, n-butyl, sec-butyl, isobutyl, tert-butyl, or —COMe;

R$^5$ represents hydrogen, amino, formyl, methyl, ethyl, n-propyl, isopropyl, n-butyl, sec-butyl, isobutyl, tert-butyl, vinyl, allyl, propargyl, methoxy, methoxymethyl, —COMe, —COEt, tert-butoxycarbonyl, or oxamoyl; or R$^4$ and R$^5$ together represent ethylidene, isopropylidene, sec-butylidene, benzylidene, or nitrobenzylidene; or R$^4$ and R$^5$ together with the nitrogen atom to which they are attached represent a 5- or 6-membered saturated heterocycle selected from the group consisting of morpholine, piperidine, thiomorpholine, and pyrrolidine, each of which is optionally mono- or disubstituted by identical or different substituents selected from the group consisting of methyl, ethyl, n-propyl, isopropyl, n-butyl, sec-butyl, isobutyl, and tert-butyl;

R$^9$ represents hydrogen, methyl, ethyl, n-propyl, isopropyl, n-butyl, sec-butyl, isobutyl, tert-butyl, —CH$_2$CF$_3$, —CH$_2$CF$_2$H, —CH$_2$CF$_2$CF$_3$, cyclopropyl, cyclopentyl, or cyclohexyl;

R$^{10}$ represents fluorine, chlorine, bromine, methyl, ethyl, n-propyl, isopropyl, n-butyl, sec-butyl, isobutyl, tert-butyl, —COMe, —COEt, —CO$_2$Me, —CO$_2$Et, or cyclohexyl; or represents phenyl or benzyl that are optionally mono- to tetrasubstituted in the aryl moiety by identical or different substituents selected from the group consisting of fluorine, chlorine, bromine, and methyl; and R$^{14}$ represents hydrogen, methyl, ethyl, n-propyl, isopropyl, n-butyl, sec-butyl, isobutyl, tert-butyl, —CH$_2$CF$_3$, —CH$_2$CF$_2$H, or —CH$_2$CF$_2$CF$_3$.

11. A pyrazolylpyrimidine according to claim 1 having formula (I-m)

(I-m)

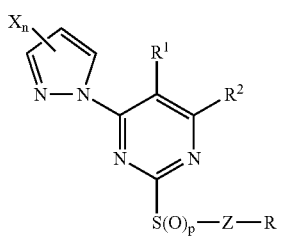

in which R$^1$, R$^2$, X, n, p, Z, and R have the meanings given in claim 1 for formula (I).

12. A pyrazolylpyrimidine according to claim 1 having formula (I-n)

(I-n)

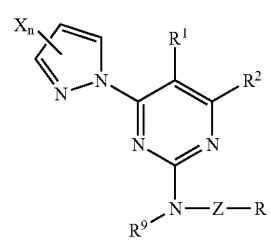

in which R$^1$, R$^2$, X, n, Z, R, and R$^9$ have the meanings given in claim 1 for formula (I).

13. A pyrazolylpyrimidine according to claim 1 having formula (I-o)

(I-o)

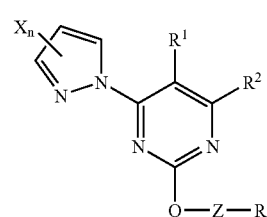

in which R$^1$, R$^2$, X, n, Z, and R have the meanings given in claim 1 for formula (I).

14. A pyrazolylpyrimidine according to claim 1 having formula (I-p)

(I-p)

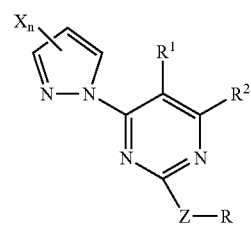

in which R$^1$, R$^2$, X, n, Z and R have the meanings given in claim 1 for formula (I).

15. A pyrazolylpyrimidine having formula (I-m)

(I-m)

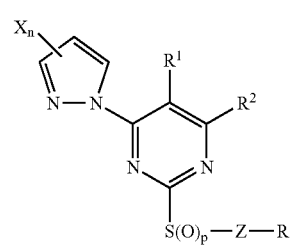

in which

R$^1$ and R$^2$ independently of one another represent hydrogen, halogen, nitro, cyano, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or cycloalkyl; or represent aryl, arylalkyl, or saturated or unsaturated heterocyclyl having 1 to 4 heteroatoms selected from the group consisting of nitrogen, oxygen, and sulphur, each of which radicals is optionally substituted by substituents from the group consisting of halogen, alkyl, halogenoalkyl, alkoxy, and halogenoalkoxy, or R¹ and R² together represent alkylene or alkenylene, where the carbon chain is optionally interrupted by 1 to 3 heteroatoms selected from the group consisting of nitrogen and oxygen and where the resulting ring is optionally substituted by halogen or alkyl, X represents halogen, nitro, cyano, hydroxyl, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R³, —SO$_2$NR⁴R⁵, —NR⁴R⁵, —COR⁶, —CO$_2$R⁷, —CSR⁶, —CONR⁴R⁵, —NHCO$_2$R⁸, or cycloalkyl; or represents aryl, arylalkyl, or saturated or unsaturated heterocyclyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, and halogenoalkoxy; or, when n represents 2 or 3, two adjacent X together optionally represent alkylene or alkenylene, where the carbon chain is optionally interrupted by 1 or 2 heteroatoms selected from the group consisting of nitrogen and oxygen, n represents 0, 1, 2, or 3, where X represents identical or different radicals when n represents 2 or 3, p represents 0, 1, or 2, Z represents —(CH$_2$)$_r$—, —(CH$_2$)$_t$—(CHR¹⁰)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R¹¹)—(CH$_2$)$_t$—, or —(CH$_2$)$_t$—C(R¹²)=C(R¹³)—(CH$_2$)$_w$—, r represents 1, 2, 3, 4, 5, or 6, t and w independently of one another represent 0, 1, 2, 3, or 4, R represents the group

A represents oxygen, sulphur or NR¹⁵,

E represents —OR¹⁶, —SR¹⁶, —O⁻M, or —S⁻M,

M represents ammonium that is optionally mono- to tetrasubstituted by identical or different radicals selected from the group consisting of alkyl, aryl, and arylalkyl; or represents an alkali metal ion, or M represents an alkaline earth metal ion forming a salt with two molecules of a compound of formula (I), R³ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, R⁴ represents hydrogen, alkyl, halogenoalkyl, cycloalkyl, or alkylcarbonyl, R⁵ represents hydrogen, amino, formyl, alkyl, alkenyl, alkynyl, halogenoalkyl, cycloalkyl, alkoxy, alkoxyalkyl, alkylcarbonyl, alkoxycarbonyl, and oxamoyl, or R⁴ and R⁵ together represent alkylidene; or represent optionally halogen-, nitro-, alkyl-, or halogenoalkyl-substituted benzylidene; or R⁴ and R⁵ together with the nitrogen atom to which they are attached form a saturated or unsaturated heterocycle that optionally contains a further nitrogen, oxygen, or sulphur atom and that is optionally substituted by alkyl, R⁶ represents hydrogen, alkyl, halogenoalkyl, or arylalkyl, R⁷ represents hydrogen, alkyl, halogenoalkyl, cycloalkyl, cycloalkylalkyl, aryl, or arylalkyl, R⁸ represents alkyl or halogenoalkyl, R¹⁰ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R¹¹ represents hydrogen or alkyl, R¹² and R¹³ independently of one another represent hydrogen, hydroxyl, alkyl, or alkoxy, R¹⁵ represents hydrogen, alkyl, alkoxy, cyano, or dialkylamino, and R¹⁶ represents hydrogen or represents —NR⁴R⁵; represents alkyl, alkenyl, or alkynyl, each of which radicals is optionally substituted by substituents selected from the group consisting of halogen, amino, hydroxyl, cyano, nitro, alkoxy, halogenoalkoxy, alkylthio, halogenoalkylthio, alkoxycarbonyl, alkenyloxycarbonyl, alkylcarbonyloxy, oxyalkyleneoxy, aryloxy, halogenoaryloxy, —CONR⁴R⁵, —NR⁴R⁵, —ONR⁴R⁵, and —C(R¹⁴)N—OR¹⁴; or represents aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, halogenoalkylthio, alkoxycarbonyl, and alkylcarbonyloxy.

16. A pyrazolylpyrimidine according formula (I-n)

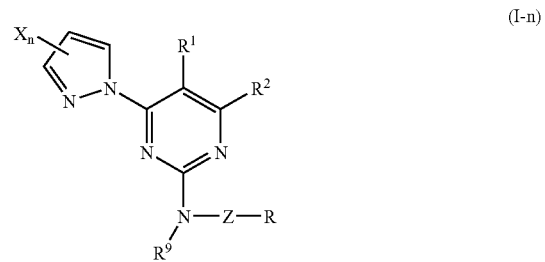

in which

R¹ and R² independently of one another represent hydrogen, halogen, nitro, cyano, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R³, —NR⁴R⁵, —COR⁶, —CO$_2$R⁷, —CSR⁶, —CONR⁴R⁵, —NHCO$_2$R⁸, or cycloalkyl; or represent aryl, arylalkyl, or saturated or unsaturated heterocyclyl having 1 to 4 heteroatoms selected from the group consisting of nitrogen, oxygen, and sulphur, each of which radicals is optionally substituted by substituents from the group consisting of halogen, alkyl, halogenoalkyl, alkoxy, and halogenoalkoxy, or R¹ and R² together represent alkylene or alkenylene, where the carbon chain is optionally interrupted by 1 to 3 heteroatoms selected from the group consisting of nitrogen and oxygen and where the resulting ring is optionally substituted by halogen or alkyl, X represents halogen, nitro, cyano, hydroxyl, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R³, —SO$_2$NR⁴R⁵, —NR⁴R⁵, —COR⁶, —CO$_2$R⁷, —CSR⁶, —CONR⁴R⁵, —NHCO$_2$R⁸, or cycloalkyl; or represents aryl, arylalkyl, or saturated or unsaturated heterocyclyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, and halogenoalkoxy; or, when n represents 2 or 3, two adjacent X together optionally represent alkylene or alkenylene, where the carbon chain is optionally interrupted by 1 or 2 heteroatoms selected from the group consisting of nitrogen and oxygen, n represents 0, 1, 2, or 3, where X represents identical or different radicals when n represents 2 or 3, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5, or 6, t and w independently of one another represent 0, 1, 2, 3, or 4, R represents the group

A represents oxygen, sulphur or NR$^{15}$,

E represents —OR$^{16}$, —SR$^{16}$, —O$^-$M, —S$^-$M, or —NR$^{17}$R$^{18}$,

M represents ammonium that is optionally mono- to tetrasubstituted by identical or different radicals selected from the group consisting of alkyl, aryl, and arylalkyl; or represents an alkali metal ion, or M represents an alkaline earth metal ion forming a salt with two molecules of a compound of formula (I), R$^3$ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, R$^4$ represents hydrogen, alkyl, halogenoalkyl, cycloalkyl, or alkylcarbonyl, R$^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, and oxamoyl, or R$^4$ and R$^5$ together represent alkylidene; or represent optionally halogen-, nitro-, alkyl-, or halogenoalkyl-substituted benzylidene; or R$^4$ and R$^5$ together with the nitrogen atom to which they are attached form a saturated or unsaturated heterocycle that optionally contains a further nitrogen, oxygen, or sulphur atom and that is optionally substituted by alkyl, R$^6$ represents hydrogen, alkyl, halogenoalkyl, or arylalkyl, R$^7$ represents hydrogen, alkyl, halogenoalkyl, cycloalkyl, cycloalkylalkyl, aryl, or arylalkyl, R$^8$ represents alkyl or halogenoalkyl, R$^9$ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, R$^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R$^{11}$ represents hydrogen or alkyl, R$^{12}$ and R$^{13}$ independently of one another represent hydrogen, hydroxyl, alkyl, or alkoxy, R$^{15}$ represents hydrogen, alkyl, alkoxy, cyano, or dialkylamino, R$^{16}$ represents hydrogen or represents —NR$^4$R$^5$; represents alkyl, alkenyl, or alkynyl, each of which radicals is optionally substituted by substituents selected from the group consisting of halogen, amino, hydroxyl, cyano, nitro, alkoxy, halogenoalkoxy, alkylthio, halogenoalkylthio, alkoxycarbonyl, alkenyloxycarbonyl, alkylcarbonyloxy, oxyalkyleneoxy, aryloxy, halogenoaryloxy, —CONR$^4$R$^5$, —NR$^4$R$^5$, —ONR$^4$R$^5$, and —C(R$^{14}$)=N—OR$^{14}$; or represents aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, halogenoalkylthio, alkoxycarbonyl, and alkylcarbonyloxy, R$^{17}$ represents hydrogen or alkyl, and R$^{18}$ represents hydrogen, hydroxyl, amino, —SO$_2$R$^8$, alkyl, or alkenyl; or represents cycloalkyl, cycloalkylalkyl, aryl, arylalkyl, or heteroaryl or heteroarylalkyl having 1 to 4 heteroatoms selected from the group consisting of nitrogen, oxygen, and sulphur, each of which radicals is optionally substituted by substituents selected from the group consisting of halogen, hydroxyl, alkyl, halogenoalkyl, alkoxy, halogenoalkoxy, alkylthio, halogenoalkylthio, and oxyalkyleneoxy, or R$^{17}$ and R$^{18}$ together with the nitrogen atom to which they are attached represent a 5- or 6-membered saturated or unsaturated heterocycle that optionally contains 1 or 2 further heteroatoms selected from the group consisting of nitrogen, oxygen, and sulphur and that is optionally substituted by alkyl, except for the compound 2-{[4-(3,5-dimethyl-1H-pyrazol-1-yl)-2-pyrimidinyl]thio}acetamide.

17. A pyrazolylpyrimidine having formula (I-o)

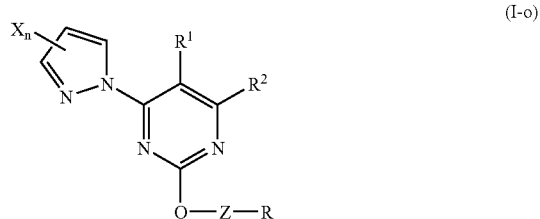

in which

R$^1$ and R$^2$ independently of one another represent hydrogen, halogen, nitro, cyano, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or cycloalkyl; or represent aryl, arylalkyl, or saturated or unsaturated heterocyclyl having 1 to 4 heteroatoms selected from the group consisting of nitrogen, oxygen, and sulphur, each of which radicals is optionally substituted by substituents from the group consisting of halogen, alkyl, halogenoalkyl, alkoxy, and halogenoalkoxy, or $R^1$ and $R^2$ together represent alkylene or alkenylene, where the carbon chain is optionally interrupted by 1 to 3 heteroatoms selected from the group consisting of nitrogen and oxygen and where the resulting ring is optionally substituted by halogen or alkyl, X represents halogen, nitro, cyano, hydroxyl, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R$^3$, —SO$_2$NR$^4$R$^5$, —NR$^4$R$^5$, —COR$^6$, —CO$_2$R$^7$, —CSR$^6$, —CONR$^4$R$^5$, —NHCO$_2$R$^8$, or cycloalkyl; or represents aryl, arylalkyl, or saturated or unsaturated heterocyclyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, and halogenoalkoxy; or, when n represents 2 or 3, two adjacent X together optionally represent alkylene or alkenylene, where the carbon chain is optionally interrupted by 1 or 2 heteroatoms selected from the group consisting of nitrogen and oxygen, n represents 0, 1, 2, or 3, where X represents identical or different radicals when n represents 2 or 3, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5, or 6, t and w independently of one another represent 0, 1, 2, 3, or 4, R represents the group

A represents oxygen, sulphur or NR$^{15}$,

E represents —OR$^{16}$, —SR$^{16}$, —O$^-$M, or —S$^-$M,

M represents ammonium that is optionally mono- to tetrasubstituted by identical or different radicals selected from the group consisting of alkyl, aryl, and arylalkyl; or represents an alkali metal ion, or M represents an alkaline earth metal ion forming a salt with two molecules of a compound of formula (I), R$^3$ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, R$^4$ represents hydrogen, alkyl, halogenoalkyl, cycloalkyl, or alkylcarbonyl, R$^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, and oxamoyl, or R$^4$ and R$^5$ together represent alkylidene; or represent optionally halogen-, nitro-, alkyl-, or halogenoalkyl-substituted benzylidene; or R$^4$ and R$^5$ together with the nitrogen atom to which they are attached form a saturated heterocycle that optionally contains a further nitrogen, oxygen, or sulphur atom and that is optionally substituted by alkyl, R$^6$ represents hydrogen, alkyl, halogenoalkyl, or arylalkyl, R$^7$ represents hydrogen, alkyl, halogenoalkyl, cycloalkyl, cycloalkylalkyl, aryl, or arylalkyl, R$^8$ represents alkyl or halogenoalkyl, R$^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R$^{11}$ represents hydrogen or alkyl, R$^{12}$ and R$^{13}$ independently of one another represent hydrogen, hydroxyl, alkyl, or alkoxy, R$^{15}$ represents hydrogen, alkyl, alkoxy, cyano, or dialkylamino, and R$^{16}$ represents hydrogen or represents —NR$^4$R$^5$; represents alkyl, alkenyl, or alkynyl, each of which radicals is optionally substituted by substituents selected from the group consisting of halogen, amino, hydroxyl, cyano, nitro, alkoxy, halogenoalkoxy, alkylthio, halogenoalkylthio, alkoxycarbonyl, alkenyloxycarbonyl, alkylcarbonyloxy, oxyalkyleneoxy, aryloxy, halogenoaryloxy, —CONR$^4$R$^5$, —NR$^4$R$^5$, —ONR$^4$R$^5$, and —C(R$^{14}$)=N—OR$^{14}$; or represents aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, halogenoalkylthio, alkoxycarbonyl, and alkylcarbonyloxy.

18. A pyrazolylpyrimidine having formula (I-p)

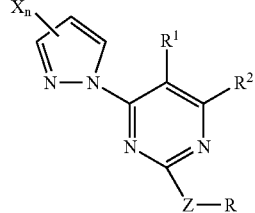

(I-p)

in which

R$^1$ and R$^2$ independently of one another represent hydrogen, halogen, nitro, cyano, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or cycloalkyl; or represent aryl, arylalkyl, or saturated or unsaturated heterocyclyl having 1 to 4 heteroatoms selected from the group consisting of nitrogen, oxygen, and sulphur, each of which radicals is optionally substituted by substituents from the group consisting of halogen, alkyl, halogenoalkyl, alkoxy, and halogenoalkoxy, or R$^1$ and R$^2$ together represent alkylene or alkenylene, where the carbon chain is optionally interrupted by 1 to 3 heteroatoms selected from the group consisting of nitrogen and oxygen and where the resulting ring is optionally substituted by halogen or alkyl, X represents halogen, nitro, cyano, hydroxyl, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R$^3$, —SO$_2$NR$^4$R$^5$, —NR$^4$R$^5$, —COR$^6$, —CO$_2$R$^7$, —CSR$^6$, —CONR$^4$R$^5$, —NHCO$_2$R$^8$, or cycloalkyl; or represents aryl, arylalkyl, or saturated or unsaturated heterocyclyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, and halogenoalkoxy; or, when n represents 2 or 3, two adjacent X together optionally represent alkylene or alkenylene, where the carbon chain is optionally interrupted by 1 or 2 heteroatoms selected from the group consisting of nitrogen and oxygen, n represents 0, 1, 2, or 3, where X represents identical or different radicals when n represents 2 or 3, Z represents —($CH_2$)$_r$—, —($CH_2$)$_t$—($CHR^{10}$)—($CH_2$)$_w$—, —($CH_2$)$_r$—C(O)—($CH_2$)$_t$—, —($CH_2$)$_r$—O—($CH_2$)$_t$—, —($CH_2$)$_r$—S(O)$_p$—($CH_2$)$_t$—, —($CH_2$)$_r$—N($R^{11}$)—($CH_2$)$_t$—, or —($CH_2$)$_t$—C($R^{12}$)=C($R^{13}$)—($CH_2$)$_w$—, r represents 1, 2, 3, 4, 5, or 6, t and w independently of one another represent 0, 1, 2, 3, or 4, R represents the group

A represents oxygen, sulphur or $NR^{15}$,

E represents —$OR^{16}$, —$SR^{16}$, —O$^-$M, or —S$^-$M,

M represents ammonium that is optionally mono- to tetrasubstituted by identical or different radicals selected from the group consisting of alkyl, aryl, and arylalkyl; or represents an alkali metal ion, or M represents an alkaline earth metal ion forming a salt with two molecules of a compound of formula (I), $R^3$ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, $R^4$ represents hydrogen, alkyl, halogenoalkyl, cycloalkyl, or alkylcarbonyl, $R^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, and oxamoyl, or $R^4$ and $R^5$ together represent alkylidene; or represent optionally halogen-, nitro-, alkyl-, or halogenoalkyl-substituted benzylidene; or $R^4$ and $R^5$ together with the nitrogen atom to which they are attached form a saturated or unsaturated heterocycle that optionally contains a further nitrogen, oxygen, or sulphur atom and that is optionally substituted by alkyl, $R^6$ represents hydrogen, alkyl, halogenoalkyl, or arylalkyl, $R^7$ represents hydrogen, alkyl, halogenoalkyl, cycloalkyl, cycloalkylalkyl, aryl, or arylalkyl, $R^8$ represents alkyl or halogenoalkyl, $R^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, $R^{11}$ represents hydrogen or alkyl, $R^{12}$ and $R^{13}$ independently of one another represent hydrogen, hydroxyl, alkyl, or alkoxy, $R^{15}$ represents hydrogen, alkyl, alkoxy, cyano, or dialkylamino, and $R^{16}$ represents hydrogen or represents —$NR^4R^5$; represents alkyl, alkenyl, or alkynyl, each of which radicals is optionally substituted by substituents selected from the group consisting of halogen, amino, hydroxyl, cyano, nitro, alkoxy, halogenoalkoxy, alkylthio, halogenoalkylthio, alkoxycarbonyl, alkenyloxycarbonyl, alkylcarbonyloxy, oxyalkyleneoxy, aryloxy, halogenoaryloxy, —$CONR^4R^5$, —$NR^4R^5$, —$ONR^4R^5$, and —C($R^{14}$)=N—$OR^{14}$; or represents aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, halogenoalkylthio, alkoxycarbonyl, and alkylcarbonyloxy.

19. A pyrazolylpyrimidine having formula (I-q)

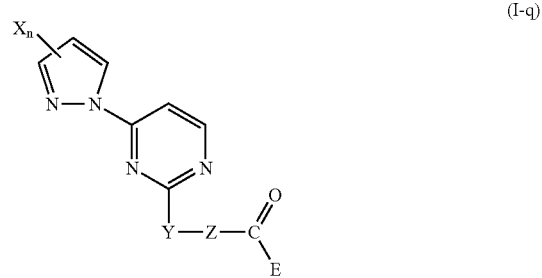

in which

X represents fluorine, chlorine, bromine, nitro, cyano, hydroxyl, methyl, ethyl, trifluoromethyl, methoxy, ethoxy, isopropoxy, trifluoromethoxy, trifluoromethylthio, vinyl, ethynyl, —$SO_2Me$, —$NH_2$, —NHMe, —$NMe_2$, or —COMe; or represents furyl, phenyl, or chlorophyll; or, when n represents 2 or 3, two adjacent radicals X together optionally represent butylene or butadienylene, n represents 0, 1, 2, or 3, where X represents identical or different radicals when n represents 2 or 3, Y represents —S— or —$NR^9$—, Z represents —$CH_2$— or —($CH_2$)$_2$—, E represents hydroxyl, methoxy, ethoxy, n-propoxy, isopropoxy, n-butoxy, isobutoxy, sec-butoxy, tert-butoxy, —NH—$SO_2Me$, —NH—$SO_2Et$, —$OCH_2CHF_2$, —$OCH_2CF_3$, —$OCH_2CF_2CHF_2$, —$OCH_2(CF_2)_2$ $CHF_2$, —$OCH(CF_3)_2$, —$OCH(CH_3)CF_3$, —$O(CH_2)_2$ $CF_3$, —$OCH_2CH_2Cl$, —$OCH_2CHCl_2$, or —$OCH_2CCl_3$, $R^9$ represents hydrogen, methyl, ethyl, n-propyl, —$CH_2CF_3$, —$CH_2CF_2CF_3$, or cyclopropyl.

20. A process for preparing a pyrazolylpyrimidine having formula (I-h) according to claim 1

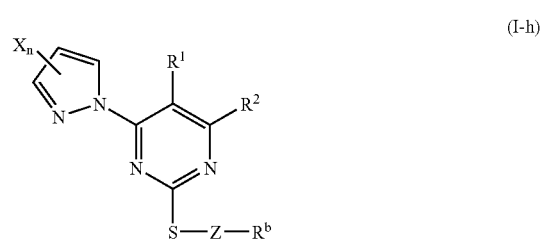

in which $R^b$ represents one of the groups

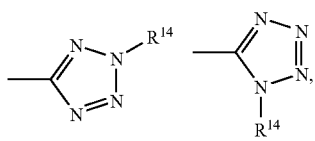

$R^1$, $R^2$, X, n, Z, and $R^{14}$ have the meanings given in claim 1 for formula (I), reacting a nitrile of formula (X)

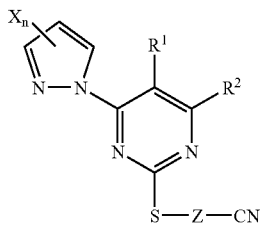

(X)

in which $R^1$, $R^2$, X, n, and Z have the meanings given in claim 1 for formula (I),
with a trialkyltin azide, optionally in the presence of a diluent.

21. A process for preparing pyrazolylpyrimidines of formula (I)

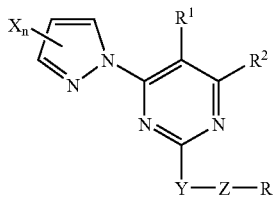

(I)

in which
- $R^1$ and $R^2$ independently of one another represent hydrogen, halogen, nitro, cyano, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_P$R$^3$, —NR$^4$R$^5$, —COR$^6$, —CO$_2$R$^7$, —CSR$^8$, —CONR$^4$R$^5$, NHCO$_2$R$^8$, or cycloalkyl; or represent aryl, arylalkyl, or saturated or unsaturated heterocyclyl having 1 to 4 heteroatoms selected from the group consisting of nitrogen, oxygen, and sulphur, each of which radicals is optionally substituted by substituents from the group consisting of halogen, alkyl, halogenoalkyl, alkoxy, and halogenoalkoxy, or
- $R^1$ and $R^2$ together represent alkylene or alkenylene, where the carbon chain is optionally interrupted by 1 to 3 heteroatoms selected from the group consisting at nitrogen and oxygen and where the resulting ring is optionally substituted by halogen or alkyl,
- X represents halogen, nitro, cyano, hydroxyl, alkyl, halogenoalkyl, alkoxy, halogenoalkoxy, alkenyl, aikynyl, alkanyloxy, haloganoalkenyloxy, alkynyloxy, halogenoalkynyloxy, —S(O)$_P$R, —SO$_2$NR$^4$R$^5$, —NR$^4$R$^5$, —COR$^6$, CO$_2$R$^7$, —CSR$^6$, —CONR$^4$R$^5$, —NHCO$_2$R$^6$, or-cycloalkyl; or represents aryl, arylalkyl, or saturated or unsaturated heterocyclyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, and halogenoalkoxy; or, when n represents 2 or 3, two adjacent X together optionally represent alkylene or alkenylene, where the carbon chain is optionally interrupted by 1 or 2 hetero-atoms selected from the group consisting of nitrogen and oxygen, n represents 0, 1, 2, or 3, where X represents identical or different radicals when n represents 2 or 3,
Y represents a direct bond, oxygen, —S(O)$_P$—, or —NR$^9$—,
p represents 0, 1, or 2,
Z represents —(CH$_2$)$_r$—, —(CH$_2$)$_r$—(CHR$^{10}$)—(CH$_2$)$_w$—, —(CH$_2$)$_r$—C(O)—(CH$_2$)$_r$—, —(CH$_2$)$_r$—C(CH$_2$)$_r$—, —(CH$_2$)$_r$—S(O)$_p$—(CH$_2$)$_r$—(CH$_2$)$_r$—N(R$^{11}$)—(CH$_2$)$_r$—, or —(CH$_2$)$_r$—C(R$^{12}$)=C(R$^{13}$)—(CH$_2$)$_w$—,
r representst 1, 2, 3, 4, 5, or 6,
t and w independently of one another represent 0, 1, 2, 3, or 4,
R represents the group

or represents a carboxyllc acid bloisostere (acid mimic) selected from the group consisting of

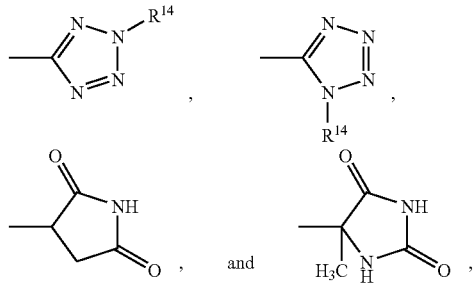

A represents oxygen, sulphur, or NR$^{15}$,
E represents —OR$^{16}$—SR$^{16}$, —O—M, —S—M, or —NR$^{17}$R$^{18}$,
M represents ammonium that is optionally mono- to tetrasubstituted by identical or different radicals selected from the group consisting of alkyl, aryl, and arylalkyl; or represents an alkali metal ion, or
M represents an alkaline earth metal ion forming a salt with two molecules of a compound of formula (I),
$R^3$ represents hydrogen, alkyl, halogenoalkyl, cycloalkyl, or cycloalkylalkyl; or represents aryl, arylalkyl, or saturated or unsaturated heterocyclyl or heterocyclytalkyl having 1 to 4 heteroatoms selected from the group consisting of nitrogen, oxygen, and sulphur, each of which radicals is optionmally substituted by substituents selected from the group consisting of halogen, alkyl, halogenoalkyl, alkoxy, halogenoalkoxy, alkylthio, and halogenoalkylthio;
$R^4$ represents hydrogen, alkyl, halogenoalkyl, cycloalkyl, or alkylcarbonyl,
$R^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, and oxamoyl, or
$R^4$ and $R^5$ together represent alkylidene; or represent optionally halogen-, nitro-, alkyl-, or halogenoalkyl-substituted benzyidene; or $R^4$ and $R^5$ together with the nitrogen atom to which they are attached form a saturated or unsaturated heterocycle that optionally contains a further nitrogen, oxygen, or sulphur atom and that is optionally substituted by alkyl,
R represents hydrogen, alkyl, halogenoalkyl, or arytalkyl,
$R^7$ represents hydrogen, alkyl, halogenoalkyl, cycloalkyl, cycloalkylalkyl, aryl, or arylalkyl,
$R^8$ represents alkyl or halogenoalkyl,
$R^9$ represents hydrogen, alkyl, halogenoalkyl, cycloalkyl, or cycloalkylalkyl; or represents aryl, arylalkyl, or saturated or unsaturated heterocycyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthlo, $R^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, $R^{11}$ represents hydrogen or alkyl, $R^{12}$ and $R^{13}$ independently of one another represent hydrogen, hydroxyl, alkyl, or alkoxy, $R^{14}$ represents hydrogen, alkyl, or halogenoalkyl, $R^{15}$ represents hydrogen, alkyl, alkoxy, cyano, or dialkylamlno, $R^{16}$ reoresents hydrogen or represents —$NR^4R^5$; represents alkyl, alkenyl, or alkynyl, each of which radicals is optionally substituted by substituents selected from the group consisting of halogen, amino, hydroxyl, cyano, nitro, alkoxy, halogenoalkoxy, alkylthio, halogenoalkylthlo, alkoxycarbonyl, alkenyloxycarbonyl, aikylcarbonyloxy, oxyalkyleneoxy, aryloxy, halogenoaryloxy, —$CONR^4R^5$, —$NR^4R^5$, —$ONR^4R^5$, and —$C(R^{14})$=N—$OR^{14}$; or represents aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, halogeno-alkylthio, alkoxycarbonyl, and alkylcarboryloxy, $R^{17}$ represents hydrogen or alkyl, and $R^{18}$ represents hydrogen, hydroxyl, amino, —$SO_2R^8$, alkyl, or alkenyl; or represents cycloalkyl, cycloalkylalkyl, aryl, arylalkyl, or heteroaryl or heteroarylalkyl having 1 to 4 heteroatoms selected from the group consisting of nitrogen, oxygen, and sulphur, each of which radicals is optionally substituted by substituents selected from the group consisting of halogen, hydroxyl, alkyl, halogenoalkyl, alkoxy, halogenoalkoxy, alkylthio, halogenoalkylthio, and oxyalkyleneoxy, or $R^{17}$ and $R^{18}$ together with the nitrogen atom to which they are attached represent a 5- or 6-membered saturated or unsaturated heterocycle that optionally contains 1 or 2 further heteroatoms selected from the group consisting of nitrogen, oxygen, and sulphur and that is optionally substituted by alkyl, except for the compound 2-{[4-(3,5-dimethyl-1H-pyrazol-1-yl)-2-pyrimidinyl]thio}-acetamide, comprising (1) for a pyrazolylpyrimidine having formula (I-a)

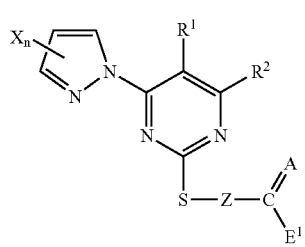

(I-a)

in which
$R^1$, $R^2$, X, n, Z, and A have the meanings given for formula (I), and $E^1$ represents —$OR^{16}$, —$SR^{16}$, or —$NR^{17}R^{18}$, where $R^{16}$, $R^{17}$, and $R^{18}$ have meanings given for formula (I), reacting a halogenopyrimidine of formula (II)

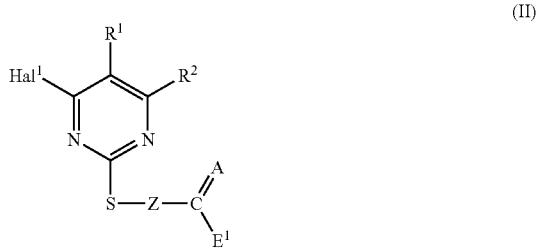

(II)

in which
$R^1$, $R^2$, Z, and A have the meanings given for formula (I-a),
$E^1$ has the meanings given for formula (I-a), and
$Hal^1$ represents halogen, with a pyrazole compound of formula (III)

(III)

in which X and n have the meanings given for formula (I-a), (A) in the presence of a base and optionally in the presence of a diluent, or (B) under the action of microwaves, optionally in the presence of a base and optionally in the presence of a diluent, or (C) in the presence of a catalyst, optionally in the presence of a base and optionally in the presence of a diluent, or (2) for a pyrazolylpylimidine having formula (I-b)

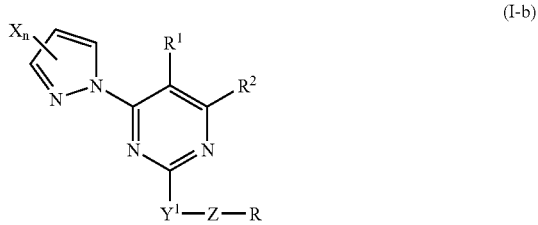

(I-b)

in which
$R^1$, $R^2$, X, n, Z, and R have the meanings given for formula (I), and
$Y^1$ represents —SO— or —SO2—, oxidizing a pyrazolylpyrimidine of formula (I-c)

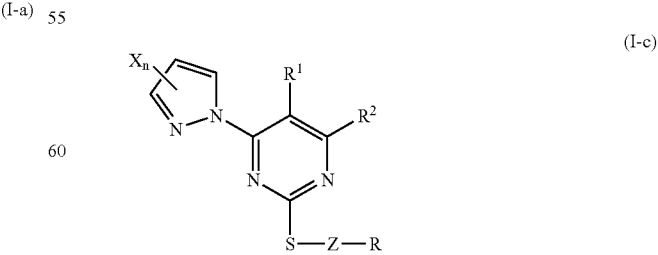

(I-c)

in which $R^1$, $R^2$, X, n, Z, and R have the meanings given for formula (I-b), with an oxidizing agent, optionally in the presence of a diluent, optionally in the presence of an acid binder, and optionally in the presence of a catalyst, or (3) for a pyrazolylpyrimidine having formula (I-d)

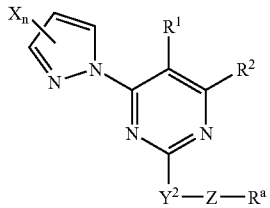
(I-d)

in which
Y² represents oxygen or —NR⁹—,
Rᵃ represents, one of the groups

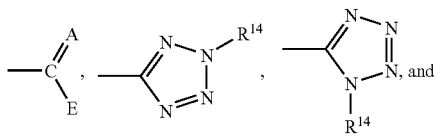

$R^1$, $R^2$, X, n, Z, $R^9$, and $R^{14}$ have the meanings given for formula (I), reacting a halogenopyrimidine of formula (IV)

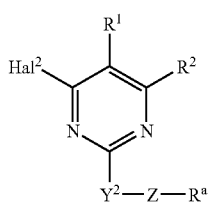
(IV)

in which
$R^1$, $R^2$ and Z have the meanings given for formula (I-d),
$Y^2$ and $R^a$ have the meanings given for formula (I-d), and
$Hal^2$ represents halogen,
with a pyrazole compound of formula (III)

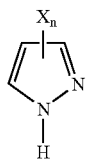
(III)

in which X and n have the meanings given for formula (I-d), optionally in the, presence of a base, optionally in the presence of a diluent, and optionally in the presence of a catalyst;
or (4) for a pyrazolylpyrinmidine having formula (I-e)

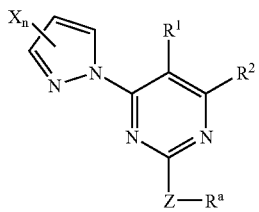
(I-e)

in which
$R^a$ represents one of the groups

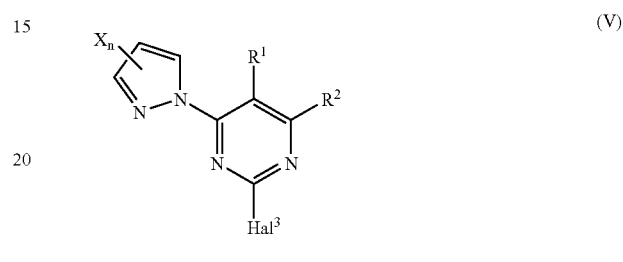

$R^1$, $R^2$, X, n, Z, and $R^{14}$ have the meanings given for formula (I), reacting a pyrazolylpyrimidine halide of formula (V)

(V)

in which
$R^1$, $R^2$, X and n have the meanings given for formula (I-e), and $Hal^3$ represents halogen,
with
(a) an organometallic compound of formula (VI)

(VI)

in which Z, A, and E have the meanings given for formula (I-e), optionally in the presence of a base, optionally in the presence of a diluent, and optionally in the presence of a catalyst, or (b) an organometallic compound of formula (VII)

BrZn—Z—CN    (VII)

in which Z has the meanings given for formula (I-e), optionally in the presence of a base, optionally in the presence of a diluent, and optionally in the presence of a catalyst, to form a nitrile of formula (VIII)

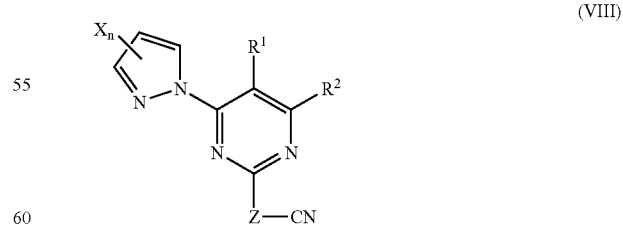
(VIII)

in which $R^1$, $R^2$, X, n and Z have the meanings given for formula (I-e), that is then reacted with a trialkyltin azide, optionally in the presence of a diluent;
or (5) for a pyrazolylpyrimidine having formula (I-f)

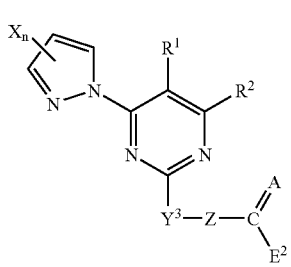
(I-f)

in which
Y³ represents a direct bond, oxygen, sulphur, or —NR⁹—,
E² represents —O—M or —S—M, and
R¹, R², X, n, Z, A, M, and R⁹ have the meanings given for formula (I), reacting a pyrazolylpyrimidine of formula (I-g)

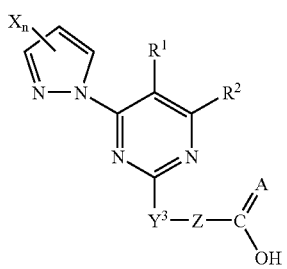
(I-g)

in which
R¹, R², X, n, Z, and A have the meanings given for formula (I-f), and
Y³ has the meanings given for formula (I-f),
with a hydroxide of formula (IX)

 M OH⁻ (IX)

in which M has the meanings given for formula (I-f), optionally in the presence of a diluent,
or
(6) for a pyrazolylpyrimidine having formula (I-j)

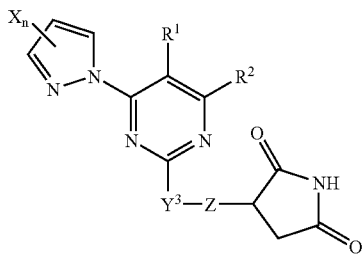
(I-j)

in which
Y³ represents a direct bond, oxygen, sulphur, or —NR⁹—, and
R¹, R², X, n, Z, and R⁹ have the meanings given for formula (I), hydrogenating a pyrazolylpyrimidine of formula (I-k)

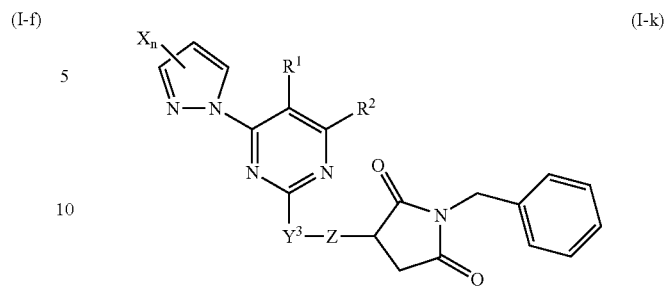
(I-k)

in which
R¹, R², X, n, and Z have the meanings given for formula (I), and
Y³ has the meanings given for formula (I-j),
optionally in the presence of a diluent and in the presence of a catalyst, or
(7) for a pyrazolylpyrimidine having formula (I-l)

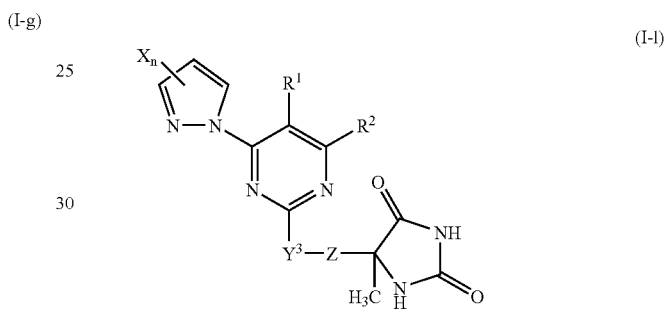
(I-l)

in which
Y³ represents a direct bond, oxygen, sulphur, or —NR⁹—, and
R¹, R², X, n, Z, and R⁹ have the meanings given for formula (I), reacting a keto compound of formula (XI)

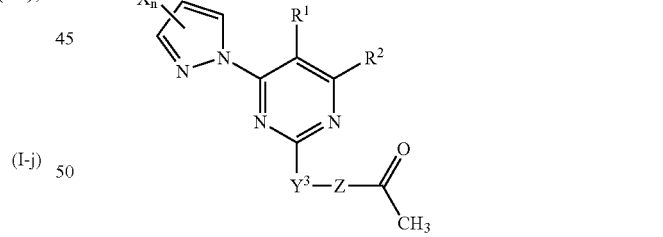
(XI)

in which
R¹, R², X, n, Z, and R⁹ have the meanings given for formula (I), and
Y³ has the meanings given for formula (I-l),
with ammonium carbonate and potassium cyanide, optionally in the presence of a diluent.

22. A pesticide comprising at least one compound of formula (I) according to claim 1 and one or more extenders and/or surfactants.

23. A process for preparing pesticides comprising mixing a compound of formula (I) according to claim 1 with one or more extenders and/or surfactants.

24. A method for controlling pests comprising allowing a pyrazolylpyrimidine of formula (I)

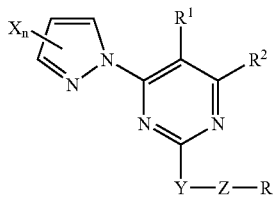

(I)

in which

R¹ and R² independently of one another represent hydrogen, halogen, nitro, cyano, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R³, —NR⁴R⁵, —COR⁶, —CO₂R⁷, —CSR⁶, —CONR⁴R⁵, —NHCO₂R⁸, or cycloalkyl; or represent aryl, arylalkyl, or saturated or unsaturated heterocyclyl having 1 to 4 heteroatoms selected from the group consisting of nitrogen, oxygen, and sulphur, each of which radicals is optionally substituted by substituents from the group consisting of halogen, alkyl, halogenoalkyl, alkoxy, and halogenoalkoxy, or R¹ and R² together represent alkylene or alkenylene, where the carbon chain is optionally interrupted by 1 to 3 heteroatoms selected from the group consisting of nitrogen and oxygen and where the resulting ring is optionally substituted by halogen or alkyl, X represents halogen, nitro, cyano, hydroxyl, alkyl, halogenoalkyl, alkoxy, halogenoalkoxy, alkenyl, alkynyl, alkenyloxy, halogenoalkenyloxy, alkynyloxy, halogenoalkynyloxy, —S(O)$_p$R³, —SO₂NR⁴R⁵, —NR⁴R⁵, —COR⁶, —CO₂R⁷, —CSR⁶, —CONR⁴R⁵, —NHCO₂R⁸, or cycloalkyl; or represent aryl, arylalkyl, or saturated or unsaturated heterocyclyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, and halogenoalkoxy; or, when n represents 2 or 3, two adjacent X together optionally represent alkylene or alkenylene, where the carbon chain is optionally interrupted by 1 or 2 heteroatoms selected from the group consisting of nitrogen and oxygen, n represents 0, 1, 2, or 3, where X represents identical or different radicals when n represents 2 or 3, Y represents a direct bond, oxygen, —S(O)$_p$—, or —NR⁹—, p represents 0, 1, or 2, Z represents —(CH₂)$_r$—, —(CH₂)$_t$—(CHR¹⁰) —(CH₂)$_w$—, —(CH₂)$_r$—C(O)—(CH₂)$_t$—, —(CH₂)$_r$—O—(CH₂)$_t$—, —(CH₂)$_r$—S(O)$_p$—(CH₂)$_t$—, —(CH₂)$_r$—N(R¹¹)—(CH₂)$_t$—, or —(CH₂)$_t$—C(R¹²) =C(R¹³)—(CH₂)$_w$—, r represents 1, 2, 3, 4, 5, or 6, t and w independently of one another represent 0, 1, 2, 3, or 4, R represents the group

or represents a carboxylic acid bioisostere (acid mimic) selected from the group consisting of

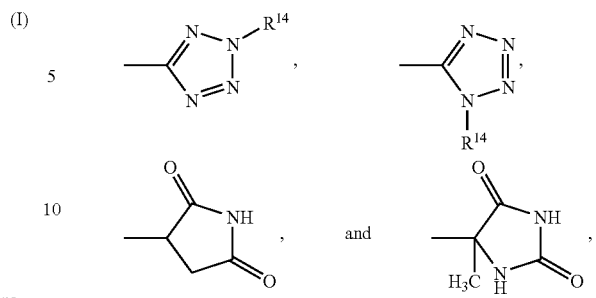

A represents oxygen, sulphur, or NR¹⁵,

E represents —OR¹⁶, —SR¹⁶, —O—M, —S—M, or —NR¹⁷R¹⁸,

M represents ammonium that is optionally mono- to tetrasubstituted by identical or different radicals selected from the group consisting of alkyl, aryl, and arylalkyl; or represents an alkali metal ion, or M represents an alkaline earth metal ion forming a salt with two molecules of a compound of formula (I), R³ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, R⁴ represents hydrogen, alkyl, halogenoalkyl, cycloalkyl, or alkylcarbonyl, R⁵ represents hydrogen, amino, formyl, alkyl, alkenyl, alkynyl, halogenoalkyl, cycloalkyl, alkoxy, alkoxyalkyl, alkylcarbonyl, alkoxycarbonyl, and oxamoyl, or R⁴ and R⁵ together represent alkylidene; or represent optionally halogen-, nitro-, alkyl-, or halogenoalkyl-substituted benzylidene; or R⁴ and R⁵ together with the nitrogen atom to which they are attached form a saturated or unsaturated heterocycle that optionally contains a further nitrogen, oxygen, or sulphur atom and that is optionally substituted by alkyl, R⁶ represents hydrogen, alkyl, halogenoalkyl, or arylalkyl, R⁷ represents hydrogen, alkyl, halogenoalkyl, cycloalkyl, cycloalkylalkyl, aryl, or arylalkyl, R⁸ represents alkyl or halogenoalkyl, R⁹ represents hydrogen, alkyl, halogenoalkyl, cycloalkyl, or cycloalkylalkyl; or represents aryl, arylalkyl, or saturated or unsaturated heterocyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, and halogenoalkylthio, R¹⁰ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R¹¹ represents hydrogen or alkyl, R¹² and R¹³ independently of one another represent hydrogen, hydroxyl, alkyl, or alkoxy, R¹⁴ represents hydrogen, alkyl, or halogenoalkyl, R¹⁵ represents hydrogen, alkyl, alkoxy, cyano, or dialkylamino, $R^{16}$ represents hydrogen or represents —$NR^4R^5$; represents alkyl, alkenyl, or alkynyl, each of which radicals is optionally substituted by substituents selected from the group consisting of halogen, amino, hydroxyl, cyano, nitro, alkoxy, halogenoalkoxy, alkylthio, halogenoalkylthio, alkoxycarbonyl, alkenyloxycarbonyl, alkylcarbonyloxy, oxyalkyleneoxy, aryloxy, halogenoaryloxy, —$CONR^4R^5$, —$NR^4R^5$, —$ONR^4R^5$, and —$C(R^{14})$=N—$OR^{14}$; or represents aryl, arylalkyl, cycloalkyl, cycloalkylalkyl, or saturated or unsaturated hetero-cyclyl or heterocyclylalkyl having 1 to 4 heteroatoms selected from the group consisting of nitrogen, oxygen, and sulphur, each of which radicals is optionally substituted by substituents selected from the group consisting of halogen, alkyl, halogenoalkyl, alkoxy, halogenoalkoxy, alkylthio, halogeno-alkylthio, alkoxycarbonyl, and alkylcarbonyloxy, $R^{17}$ represents hydrogen or alkyl, and $R^{18}$ represents hydrogen, hydroxyl, amino, —$SO_2R^8$, alkyl, or alkenyl; or represents cycloalkyl, cycloalkylalkyl, aryl, arylalkyl, or heteroaryl or heteroarylalkyl having 1 to 4 heteroatoms selected from the group consisting of nitrogen, oxygen, and sulphur, each of which radicals is optionally substituted by substituents selected from the group consisting of halogen, hydroxyl, alkyl, halogenoalkyl, alkoxy, halogenoalkoxy, alkylthio, halogenoalkylthio, and oxyalkyleneoxy, or $R^{17}$ and $R^{18}$ together with the nitrogen atom to which they are attached represent a 5- or 6-membered saturated or unsaturated heterocycle that optionally contains 1 or 2 further heteroatoms selected from the group consisting of nitrogen, oxygen, and sulphur and that is optionally substituted by alkyl, except for the compound 2-{[4-(3,5-dimethyl-1 H-pyrazol-1-yl)-2-pyrimidinyl]thio}-acetamide, to act on pests and/or their habitat.

25. A method according to claim 24 wherein R represents a carboxylic acid bioisostere selected from the group consisting of

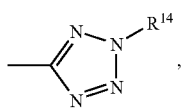 , 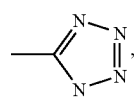 ,

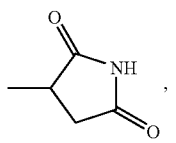 , and 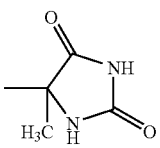 , where $R^{14}$ represents hydrogen, alkyl, or halogenoalkyl.

26. A method according to claim 24 in which $R^1$ and $R^2$ independently of one another represent hydrogen, halogen, nitro, cyano, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$alkenyl, $C_2$–$C_6$-alkynyl, $C_2$–$C_6$-alkenyloxy, $C_2$–$C_6$-halogenoalkenyloxy, $C_2$–$C_6$-alkynyloxy, $C_2$–$C_6$-halogenoalkynyloxy, —$S(O)_pR^3$, —$NR^4R^5$, —$COR^6$, —$CO_2R^7$, —$CSR^6$, —$CONR^4R^5$, —$NHCO_2R^8$, or $C_3$–$C_7$-cycloalkyl; or represent aryl, aryl-$C_1$–$C_6$-alkyl, or 5- or 6-membered saturated or unsaturated heterocyclyl having 1 to 4 heteroatoms that contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$–$C_6$-alkyl, $C_1$–$C_6$-halogenoalkyl, $C_1$–$C_6$-alkoxy, and $C_1$–$C_6$-halogenoalkoxy; or $R^1$ and $R^2$ together represent $C_3$–$C_5$-alkylene or C3-C4-alkenylene, where the carbon chain is optionally interrupted by 1 or 2 heteroatoms that are 0 to 2 nitrogen atoms and/or 0 or 1 oxygen atom, and where the resultant ring is optionally mono- or polysubstituted by identical or different substituents selected from the group consisting of halogen and $C_1$–$C_6$-alkyl;

X represents halogen, nitro, cyano, hydroxyl, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkynyl, $C_2$–$C_6$-alkenyloxy, $C_2$–$C_6$-halogenoalkenyloxy, $C_2$–$C_6$-alkynyloxy, $C_2$–$C_6$-halogenoalkynyloxy, —$S(O)_pR_3$, —$SO_2NR^4R^5$, —$NR^4R^5$, —$COR^6$, —$CO_2R^7$, —$CSR^6$, —$CONR^4R^5$, —$NHCO_2R^8$, or $C_3$–$C_7$-cycloalkyl; or represents aryl, aryl-$C_1$–$C_6$-alkyl, or 5- or 6-membered saturated or unsaturated heterocyclyl having 1 to 4 heteroatoms that contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$–$C_6$-alkyl, $C_1$–$C_6$-halogenoalkyl, $C_1$–$C_6$-alkoxy, and $C_1$–$C_6$-halogenoalkoxy; or, when n represents 2 or 3, two adjacent radicals X together optionally represent $C_3$–$C_5$-alkylene or $C_3$–$C_4$-alkenylene, where the carbon chain is optionally interrupted by 1 or 2 heteroatoms that are 0 to 2 nitrogen atoms and/or 0 or 1 oxygen atom;

n represents 0, 1, 2 or 3, where X represents identical or different radicals when n represents 2 or 3;

Y represents a direct bond, oxygen, —$S(O)_p$—, or $NR^9$—;

p represents 0, 1, or 2;

Z represents —$(CH_2)_r$—, —$(CH_2)_t$—$(CHR^{10})$—$(CH_2)_w$—, —$(CH_2)_r$—$C(O)(CH_2)_t$—, —$(CH_2)_r$—O—$(CH_2)_t$—, —$(CH_2)_r$—$S(O)_p$—$(CH_2)_t$—, —$(CH_2)_r$—$N(R^{11})$—$(CH_2)_t$—, or r represents 1, 2, 3, 4, 5, or 6;

t and w independently of one another represent 0, 1, 2, 3, or 4;

Rrepresents the group

or represents a carboxylic acid bioisostere (acid mimic) selected from the group consisting of

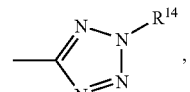 , 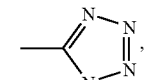 ,

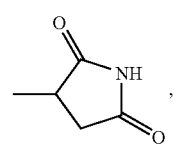 , and 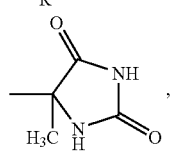 ,

A represents oxygen, sulphur, or $NR^{15}$;

E represents —OR$^{16}$, —SR$^{16}$, —O—M, —S—M, or —NR$^{17}$R$^{18}$,

M represents ammonium that is optionally mono- to tetrasubstituted by identical or different substituents selected from the group consisting of C$_1$–C$_6$-alkyl, aryl, and aryl-C$_1$–C$_6$-alkyl; or represents a lithium cation (Li$^+$), a sodium cation (Na$^+$), or a potassium cation (K$^+$);

M or represents a magnesium cation (Mg$^{2+}$) or a calcium cation (Ca$^{2+}$) forming a salt with two molecules of a compound of formula (I), R$^3$ represents hydrogen, C$_1$–C$_6$-alkyl, C$_1$–C$_6$-halogenoalkyl, C$_3$–C$_7$-cycloalkyl, or C$_3$–C$_7$-cycloalkyl-C$_1$–C$_6$-alkyl; or represents aryl, aryl-C$_1$–C$_6$-alkyl, or 5- or 6-membered saturated or unsaturated heterocyclyl or heterocyclyl-C$_1$–C$_6$-alkyl having 1 to 4 heteroatoms that contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, and C$_1$–C$_6$-halogenoalkylthio;

R$^4$ represents hydrogen, C$_1$–C$_6$-alkyl, C$_1$–C$_6$-halogenoalkyl, C$_3$–C$_7$-cycloalkyl, or C$_1$–C$_6$-alkylcarbonyl;

R$^5$ represents hydrogen, amino, formyl, C$_1$–C$_6$-alkyl, C2-C6-alkenyl, C$_2$–C$_6$-alkynyl, C$_1$–C$_6$-halogenoalkyl, C$_3$–C$_7$-cycloalkyl, C$_1$–C$_6$-alkoxy, C$_1$–C$_6$-alkoxy-C$_1$–C$_6$-alkyl, C$_{1-C6}$-alkylcarbonyl, C$_1$–C$_6$-alkoxycarbonyl, or oxamoyl; or R$^4$ and R$^5$ together represent C$_1$–C$_6$-alkylidene; or represent benzylidene that is optionally mono- or polysubstituted by identical or different substituents selected from the group consisting of halogen, nitro, C$_1$–C$_6$-alkyl, and C$_1$–C$_6$-halogenoalkyl; or R$^4$ and R$^5$ together with the nitrogen atom to which they are attached represent a 5- or 6-membered saturated or unsaturated heterocycle that optionally contains a further nitrogen, oxygen, or sulphur atom and that is optionally mono- or polysubstituted by identical or different C$_1$–C$_6$-alkyl;

R$^6$ represents hydrogen, C$_1$–C$_6$-alkyl, C$_1$–C$_6$-halogenoalkyl, or aryl-C$_1$–C$_6$-alkyl;

R$^7$ represents hydrogen, C$_1$–C$_6$-alkyl, C$_1$–C$_6$-halogenoalkyl, C$_3$–C$_7$-cycloalkyl, C$_3$–C$_7$-cycloalkyl-C$_1$–C$_6$-alkyl, aryl, or aryl-C$_1$–C$_6$-alkyl;

R$^8$ represents C$_1$–C$_6$-alkyl or C$_1$–C$_6$-halogenoalkyl;

R$^9$ represents hydrogen, C$_1$–C$_6$-alkyl, C$_1$–C$_6$-halogenoalkyl, C$_3$–C$_7$-cycloalkyl, or C$_3$–C$_7$-cycloalkyl-C$_1$–C$_6$-alkyl; or represents aryl, aryl-C$_{1l}$–C$_6$-alkyl, or 5- or 6-membered saturated or unsaturated heterocyclyl or heterocyclyl-C$_1$–C$_6$-alkyl having 1 to 4 heteroatoms that are 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, and C$_1$–C$_6$-halogenoalkylthio;

R$^{10}$ represents halogen, C$_1$–C$_6$-alkyl, C$_1$–C$_6$-alkylcarbonyl, C$_1$–C$_6$-alkoxycarbonyl, C$_3$–C$_7$-cycloalkyl, or C$_3$–C$_7$-cycloalkyl-C$_1$–C$_6$-alkyl; or represents aryl or aryl-C$_1$–C$_6$-alkyl that is optionally mono- or polysubstituted in the aryl moiety by identical or different substituents selected from the group consisting of halogen and C$_1$–C$_6$-alkyl;

R$^{11}$ represents hydrogen or C$_1$–C$_6$-alkyl;

R$^{12}$ and R$^{13}$ independently of one another represent hydrogen, hydroxyl, C$_1$–C$_6$-alkyl, or C$_1$–C$_6$-alkoxy;

R$^{14}$ represents hydrogen, C$_1$–C$_6$-alkyl, or C$_1$–C$_6$-halogenoalkyl;

R$^{15}$ represents hydrogen, C$_1$–C$_6$-alkyl, C$_1$–C$_6$-alkoxy, cyano, or di(C$_1$–C$_6$-alkyl)amino;

R$^{16}$ represents hydrogen; represents —NR$^4$R$^5$; represents C$_1$–C$_6$-halogenoalkyl, C$_2$–C$_{16}$-halogenoalkenyl, or C$_2$–C$_{10}$-halogenoalkynyl; represents C$_1$–C$_{16}$-alkyl, C$_2$–C$_{10}$-alkenyl, or C$_2$–C$_6$-alkynyl, each of which is optionally mono- or poly-substituted by identical or different substituents selected from the group consisting of amino, hydroxyl, cyano, nitro, C$_1$–C$_6$-alkoxy, C$_1$–C$_6$-halogenoalkoxy, C$_1$–C$_6$-alkylthio, C$_1$–C$_6$-halogenoalkylthio, C$_1$–C$_6$-alkoxycarbonyl, C$_2$–C$_6$-alkenyloxycarbonyl, C$_1$–C$_6$-alkylcarbonyloxy, oxy(C$_1$–C$_6$alkylene)oxy, aryloxy, halogenoaryloxy, —CONR$^4$R$^5$, —NR$^4$R$^5$, —ONR$^4$R$^5$, and —C(R$^{14}$)=N—OR$^{14}$; or represents aryl, aryl-C$_1$–C$_6$-alkyl, C$_3$–C$_7$-cycloalkyl, C$_3$–C$_7$-cycloalkyl-C$_1$–C$_6$-alkyl, or 4- to 6-membered saturated or unsaturated heterocyclyl or heterocyclyl-C$_1$–C$_6$-alkyl having 1 to 4 heteroatoms that are 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, C$_1$–C$_6$-halogenoalkylthio, C$_1$–C$_6$-alkoxycarbonyl, and C$_1$–C$_6$-alkylcarbonyloxy, R$^{17}$ represents hydrogen or C$_1$–C$_4$-alkyl; and R$^{18}$ represents hydrogen, hydroxyl, amino, —SO$_2$R$^8$, C$_1$–C$_4$-alkyl, or C$_2$–C$_4$-alkenyl; or represents C$_3$–C$_6$-cycloalkyl, C$_3$–C$_6$-cycloalkyl-C$_1$–C$_4$-alkyl, aryl, aryl-C$_1$–C$_4$-alkyl, heteroaryl or heteroaryl-C$_1$–C$_4$-alkyl having 1 to 3 heteroatoms that are 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, hydroxyl, C$_1$–C$_4$-alkyl, C$_1$–C$_4$-halogenoalkyl having 1 to 9 fluorine, chlorine, and/or bromine atoms, C$_1$–C$_4$-alkoxy, C$_1$–C$_4$-halogenoalkoxy having 1 to 9 fluorine, chlorine, and/or bromine atoms, C$_1$–C$_4$-alkylthio, C$_1$–C$_4$-halogenoalkylthio having 1 to 9 fluorine, chlorine, and/or bromine atoms, and oxy(C$_1$–C$_4$-alkylene)oxy; or R$^{17}$ and R$^{18}$ together with the nitrogen atom to which they are attached represent a 5- or 6-membered saturated or unsaturated heterocycle that optionally contains 1 or 2 further heteroatoms that are 0 to 2 nitrogen atoms, 0 or 1 oxygen atom, and/or 0 or 1 sulphur atom and that are optionally mono- to trisubstituted by identical or different C$_1$–C$_4$-alkyl;

except for the compound 2-{[4-(3,5-dmethyl-1H-pyrazol-1-yl)-2-pyrimidinyl]thio}acetamide.

27. A method according to claim 26 wherein R represents a carboxylic acid bioisostere selected from the group consisting of

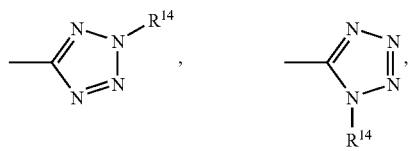

147

-continued

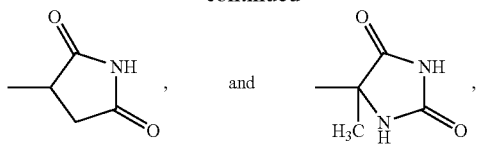

where $R^{14}$ represents hydrogen, alkyl, or halogenoalkyl.

28. A method according to claim 24 in which $R^1$ and $R^2$ independently of one another represent hydrogen, fluorine, chlorine, bromine, nitro, cyano, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_2$–$C_4$-alkenyl, $C_2$–$C_4$-alkynyl, —S(O)$_p$R$^3$, —NR$^4$R$^5$, —COR$^6$, —CO$_2$R$^7$, —CSR$^6$, —CONR$^4$R$^5$, —NHCO$_2$R$^8$, or $C_3$–$C_6$-cycloalkyl; or represent aryl aryl-$C_1$–$C_4$-alkyl, or 5- or 6-membered saturated or unsaturated heterocyclyl having 1 to 3 heteroatoms that are 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy and $C_1$–$C_4$-halogenoalkoxy having 1 to 9 fluorine, chlorine, and/or bromine atoms; or $R^1$ and $R^2$ together represent $C_3$–$C_5$-alkylene or $C_3$–$C_4$-alkenylene, where the carbon chain is optionally interrupted by 1 or 2 heteroatoms that are 0 to 2 nitrogen atoms and/or 0 or 1 oxygen atom, and where the resultant ring is optionally mono- to tetrasubstituted by identical or different substituents selected from the group consisting of fluorine, chlorine, bromine, and $C_1$–$C_4$-alkyl;

X represents fluorine, chlorine, bromine, iodine, nitro, cyano, hydroxyl, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_2$–$C_4$-alkenyl, $C_2$–$C_4$-alkynyl, —S(O)$_p$R$^3$, —SO$_2$NR$^4$R$^5$, —NR$^4$R$^5$, —COR$^6$, —CO$_2$R$^7$, —CSR$^6$, —CONR$^4$R$^5$, —NHCO$_2$R$^8$, or $C_3$–$C_6$-cycloalkyl; or represents aryl, aryl-$C_1$–$C_4$-alkyl, 5- or 6-membered saturated or unsaturated heterocyclyl having 1 to 3 heteroatoms that are 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, and $C_1$–$C_4$-halogenoalkoxy having 1 to 9 fluorine, chlorine, and/or bromine atoms; or, when n represents 2 or 3, two adjacent radicals X together optionally represent $C_3$–$C_4$-alkylene or $C_3$–$C_4$-alkenylene, where the carbon chain may be interrupted by 1 or 2 heteroatoms, which may be 0 to 2 nitrogen atoms, and/or 0 or 1 oxygen atom;

n represents 0, 1, 2, or 3, where X represents identical or different radicals when n represents 2 or 3;

Y represents a direct bond, oxygen, —S(O)$_p$—, or —NR$^9$—;

p represents 0, 1, or 2;

Z represents —(CH$_2$)$_r$—, —(CH$_2$)$_t$—(CHR$^{10}$)—(CH$_2$)$_w$—, (—CH$_2$)$_r$—C(O)—(CH$_2$)$_t$—, —(CH$_2$)$_r$—O—(CH$_2$)$_t$—, —(CH$_2$)$_r$—S(O)$_p$(CH$_2$)$_r$—, —(CH$_2$)$_r$—N(R$^{11}$)—(CH$_2$)$_r$—, or —(CH$_2$)$_t$—C(R$^{12}$)=C(R$^{13}$)—(CH$_2$)$_w$—;

r represents 1, 2, 3, or 4;

t and w independently of one another represent 0, 1, 2, 3, or 4;

R represents the group

or represents a carboxylic acid bioisostere (acid mimic) selected from the group consisting of

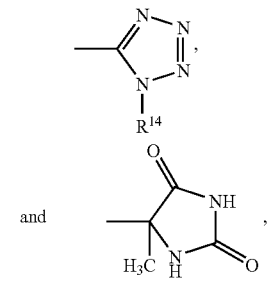

A represents oxygen or sulphur;

E represents —OR$^{16}$, —SR$^{16}$, —O—M, or —S—M,

M represents ammonium that is optionally mono- to tetrasubstituted by identical or different substituents selected from the group consisting of $C_1$–$C_6$-alkyl, phenyl, benzyl, and phenylethyl; or represents a sodium cation (Na$^+$) or a potassium cation (K$^+$);

M represents a magnesium cation (Mg$^{2+}$) or a calcium cation (Ca$^{2+}$) forming a salt with two molecules of a compound of formula (I), $R^3$ represents hydrogen, $C_1$–$C_4$-alkyl, $C_1$–$C_4$-halogenoalkyl having 1 to 9 fluorine, chlorine, and/or bromine atoms, $C_3$–$C_6$-cycloalkyl, or $C_3$–$C_6$-cycloalkyl-$C_1$–$C_4$-alkyl; or represents aryl (in particular phenyl), aryl-$C_1$–$C_4$-alkyl, 5- or 6-membered saturated or unsaturated heterocyclyl or heterocyclyl-$C_1$–$C_4$-alkyl having 1 to 3 heteroatoms, which contains 0 to 3 nitrogen atoms, 0 to 2 nonadjacent oxygen atoms and/or 0 to 2 nonadjacent sulphur atoms, each of which radicals is optionally mono- to tetrasubstituted by identical or different radicals selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_{12}$–$C_4$-halogenoalkoxy having 1 to 9 fluorine, chlorine, and/or bromine atoms, $C_1$–$C_4$-alkylthio, and $C_1$–$C_4$-halogenoalkylthio having 1 to 9 fluorine, chlorine, and/or bromine atoms;

$R^4$ represents hydrogen, $C_1$–$C_4$-alkyl, $C_1$–$C_4$-halogenoalkyl having 1 to 9 fluorine, chlorine, and/or bromine atoms, $C_3$–$C_6$-cycloalkyl, or $C_1$–$C_4$-alkylcarbonyl;

$R^5$ represents hydrogen, amino, formyl, $C_1$–$C_4$-alkyl, $C_2$–$C_4$-alkenyl, $C_2$–$C_4$-alkynyl, $C_1$–$C_4$-halogenoalkyl having 1 to 9 fluorine, chlorine, and/or bromine atoms, $C_3$–$C_6$-cycloalkyl, $C_1$–$C_4$-alkoxy, $C_1$–$C_4$-alkoxy-$C_1$–$C_4$-alkyl, $C_1$–$C_4$-alkylcarbonyl, $C_1$–$C_4$-alkoxycarbonyl, or oxamoyl; or $R^4$ and $R^5$ together represent $C_1$–$C_4$-alkylidene; or represent benzylidene that is optionally mono- to tetrasubstituted by identical or different substituents selected from the group consisting of fluorine, chlorine, bromine, nitro, $C_1$–$C_4$-alkyl, and $C_1$–$C_4$-halogenoalkyl having 1 to 9 fluorine, chlorine, and/or bromine atoms; or $R^4$ and $R^5$ together with the nitrogen atom to which they are attached represent a 5- or 6-membered saturated or unsaturated heterocycle that optionally contains a further nitrogen, oxygen, or sulphur atom and that is optionally mono- to tetrasubstituted by identical or different $C_1$–$C_4$-alkyl;

$R^6$ represents hydrogen, $C_1$–$C_4$-alkyl, $C_1$–$C_4$-halogenoalkyl having 1 to 9 fluorine, chlorine, and/or bromine atoms, or aryl-$C_1$–$C_4$-alkyl;

$R^7$ represents hydrogen, $C_1$–$C_4$-alkyl, $C_1$–$C_4$-halogenoalkyl having 1 to 9 fluorine, chlorine, and/or bromine atoms, $C_3$–$C_6$-cycloalkyl, $C_3$–$C_6$-cycloalkyl-$C_1$–$C_4$-alkyl, aryl, or aryl-$C_1$–$C_4$-alkyl;

$R^8$ represents $C_1$–$C_4$-alkyl or $C_1$–$C_4$-halogenoalkyl having 1 to 9 fluorine, chlorine, and/or bromine atoms;

$R^9$ represents hydrogen, $C_1$–$C_4$-alkyl, $C_1$–$C_4$-halogenoalkyl having 1 to 9 fluorine, chlorine, and/or bromine atoms, $C_3$–$C_6$-cycloalkyl, or $C_3$–$C_6$-cycloalkyl-$C_1$–$C_4$-alkyl; or represents aryl, aryl-$C_1$–$C_4$-alkyl, or 5- or 6-membered saturated or unsaturated heterocyclyl or heterocyclyl-$C_1$–$C_4$-alkyl having in each case 1 to 3 heteroatoms that are 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, or $C_1$–$C_4$-halogenoalkylthio having 1 to 9 fluorine, chlorine, and/or bromine atoms;

$R^{10}$ represents fluorine, chlorine, bromine, iodine, $C_1$–$C_4$-alkyl, $C_1$–$C_4$-alkylcarbonyl, $C_1$–$C_4$-alkoxycarbonyl, $C_3$–$C_6$-cycloalkyl, or $C_3$–$C_6$-cycloalkyl-$C_1$–$C_4$-alkyl; or represents aryl or aryl-$C_1$–$C_4$-alkyl, each of which radicals is optionally mono- to tetrasubstituted in the aryl moiety by identical or different substituents selected from the group consisting of fluorine, chlorine, bromine, and $C_1$–$C_4$-alkyl;

$R^{11}$ represents hydrogen or $C_1$–$C_4$-alkyl;

$R^{12}$ and $R^{13}$ independently of one another represent hydrogen, hydroxyl, $C_1$–$C_4$-alkyl, or $C_1$–$C_4$-alkoxy;

$R^{14}$ represents hydrogen, $C_1$–$C_4$-alkyl, or $C_1$–$C_4$-halogenoalkyl having 1 to 9 fluorine, chlorine, and/or bromine atoms; and $R^{16}$ represents hydrogen; represents $C_1$–$C_{16}$-halogenoalkyl having 1 to 31 fluorine, chlorine, and/or bromine atoms, $C_2$–$C_{12}$-halogenoalkenyl having 1 to 21 fluorine, chlorine, and/or bromine atoms, $C_2$–$C_8$-halogenoalkynyl having 1 to 11 fluorine, chlorine, and/or bromine atoms; represents $C_1$–$C_6$-alkyl, decyl, dodecyl, tetradecyl, hexadecyl, $C_2$–$C_6$-alkenyl, decenyl, or $C_2$–$C_4$-alkynyl, each of which is optionally mono- to tetrasubstituted by identical or different substituents selected from the group consisting of amino, hydroxyl, cyano, nitro, $C_1$–$C_4$-alkoxy, $C_1$–$C_4$-halogenoalkoxy having 1 to 9 fluorine, chlorine, and/or bromine atoms, $C_1$–$C_4$-alkylthio, $C_1$–$C_4$-halogenoalkylthio having 1 to 9 fluorine, chlorine, and/or bromine atoms, $C_1$–$C_4$-alkoxycarbonyl, $C_2$–$C_4$-alkenyloxycarbonyl, $C_1$–$C_4$-alkylcarbonyloxy, oxy($C_1$–$C_4$-alkylene)oxy, aryloxy, halogenoaryloxy, —$CONR^4R^5$, —$NR^4R^5$, —$ONR^4R^5$, and —$C(R^{14})$=N—$OR^{14}$; or represents aryl, aryl-$C_1$–$C_4$-alkyl, $C_3$–$C_6$-cycloalkyl, $C_3$–$C_6$-cycloalkyl-$C_1$–$C_4$-alkyl, or 4- to 6-membered saturated or unsaturated heterocyclyl or heterocyclyl-$C_1$–$C_4$-alkyl having 1 to 3 heteroatoms that are 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, $C_1$–$C_4$-halogenoalkylthio having 1 to 9 fluorine, chlorine, and/or bromine atoms, $C_1$–$C_4$-alkoxycarbonyl, and $C_1$–$C_4$-alkylcarbonyloxy.

29. A method according to claim 28 in which one or both of $R^1$ and $R^2$ independently represent phenyl that is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy and $C_1$–$C_4$-halogenoalkoxy having 1 to 9 fluorine, chlorine, and/or bromine atoms.

30. A method according to claim 28 in which X represents one or more phenyl that is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, and $C_1$–$C_4$-halogenoalkoxy having 1 to 9 fluorine, chlorine, and/or bromine atoms.

31. A method according to claim 28 in which $R^3$ represents phenyl that is optionally mono- to tetrasubstituted by identical or different radicals selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, and $C_1$–$C_4$-halogenoalkylthio having 1 to 9 fluorine, chlorine, and/or bromine atoms.

32. A method according to claim 28 in which $R^7$ represents phenyl.

33. A method according to claim 28 in which $R^9$ represents phenyl that is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, or $C_1$–$C_4$-halogenoalkylthio having 1 to 9 fluorine, chlorine, and/or bromine atoms.

34. A method according to claim 28 in which $R^{10}$ represents phenyl that is optionally mono- to tetrasubstituted by identical or different substituents selected from the group consisting of fluorine, chlorine, bromine, and $C_1$–$C_4$-alkyl.

35. A method according to claim 28 in which $R^{16}$ represents phenyl that is optionally mono- to tetrasubstituted by identical or different substituents selected from the group consisting of fluorine, chlorine, bromine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, $C_1$–$C_4$-halogenoalkylthio having 1 to 9 fluorine, chlorine, and/or bromine atoms, $C_1$–$C_4$-alkoxycarbonyl, and $C_1$–$C_4$-alkylcarbonyloxy.

36. A method according to claim 28 wherein R represents a carboxylic acid bioisostere selected from the group consisting of

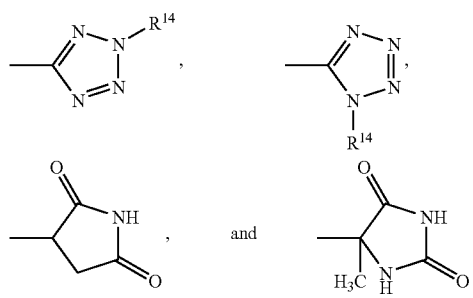

where $R^{14}$ represents hydrogen, alkyl, or halogenoalkyl.

37. A method according to claim 24 in which $R^1$ and $R^2$ independently of one another represent hydrogen, fluorine, chlorine, bromine, nitro, cyano, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, methoxy, ethoxy, n-propoxy, isopropoxy, n-butoxy, isobutoxy, sec-butoxy, tert-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, —COMe, —$CO_2Me$, —$CO_2Et$, amino, cyclopentyl, or cyclohexyl; or represent phenyl, benzyl, pyridinyl, or furyl, each of which is optionally mono- to trisubstituted by identical or different substituents selected from the group consisting of fluorine, chlorine, bromine, methyl, ethyl, methoxy, ethoxy, trifluoromethyl, and trifluoromethoxy; or $R^1$ and $R^2$ together represent propylene, butylene, propenylene, butadienylene, —$(CH_2)_2$—O—$CH_2$—, —$(CH_2)_2$—NH—$CH_2$—, —CH=CH—N=CH—, or —CH=CCl—CH=CH—;

X represents fluorine, chlorine, bromine, iodine, nitro, cyano, hydroxyl, methyl, ethyl, n-propyl, isopropyl, n-butyl, sec-butyl, isobutyl, tert-butyl, —$CF_3$, —$CCl_3$, —$OHF_2$, —$CClF_2$, —$CHCl_2$, —$CF_2CHFCl$, —$CF_2CH_2F$, —$CF_2CCl_3$, —$CH_2CF_3$, —$CF_2CHFCE_3$, —$CH_2CF_2H$, —$CH_2CF_2CF_3$, —$CF_2CF_2H$, methoxy, ethoxy, n-propoxy, isopropoxy, n-butoxy, isobutoxy, sec-butoxy, tert-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, vinyl, ethynyl, —$SO_2NH_2$, —$SO_2NHMe$, —$SO_2NMe_2$, amino, —NHMe, —$NMe_2$, —CHO, —COMe, —$CO_2Me$, —$CO_2Et$, —$CONH_2$, —CONHMe, —$CONMe_2$, —NHCOMe, cyclopentyl, or cyclohexyl; or represents phenyl, benzyl, furyl, thienyl, pyrrolyl, oxazolyl, isoxazyl, imidazyl, pyrazyl, thiazolyl, pyridyl, pyrimidinyl, pyridazyl, triazinyl, or triazyl, each of which is optionally mono- to trisubstituted by identical or different substituents selected from the group consisting of fluorine, chlorine, bromine, methyl, ethyl, methoxy, ethoxy, trifluoromethyl, and trifluoromethoxy; or, when n represents 2 or 3, two adjacent radicals X together optionally represent propylene, butylene, propenylene, butadienylene, —$(CH_2)_2$—O—$CH_2$—, —$(CH_2)_2$—NH—$CH_2$—, or —CH=OH—N=CH—;

n represents 0, 1, 2, or 3, where X represents identical or different radicals when n represents 2 or 3;

Y represents a direct bond, oxygen, —$S(O)_p$—, or —$NR^9$—;

p represents 0, 1, or 2;

Z represents —$OH_2$—, —$(CH_2)_2$—, —$(CH_2)_3$—, —$(CH_2)_4$—, —$(CHR^{10})$—, —$CH_2$—O(O)—$CH_2$—, —$CH_2$—NH—, —CH=CH—, —CH=CH—, —CH=C(OH)—, —CH=O(OMe)—, or —$CH_2$—C(OMe)=CH—;

R represents the group

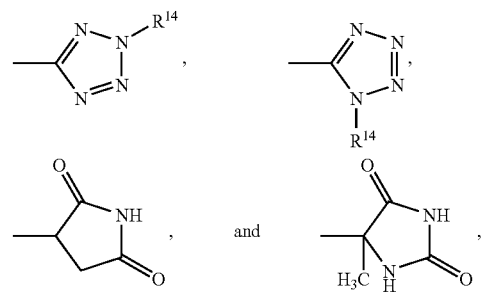

or represents a carboxylic acid bioisostere (acid mimic) selected from the group consisting of A represents oxygen or sulphur;

E represents —$OR^{16}$, —$SR^{16}$, —OM, or —$NR^{17}R^{18}$,

M represents tetrabutylammonium or trimethylbenzylammonium; or represents a sodium cation ($Na^+$) or a potassium cation ($K^+$); or M represents a magnesium cation ($Mg^{2+}$) or a calcium cation ($Ca^{2+}$) forming a salt with two molecules of a compound of formula (I), $R^4$ represents hydrogen, methyl, ethyl, n-propyl, isopropyl, n-butyl, sec-butyl, isobutyl, tert-butyl, or —COMe;

$R^5$ represents hydrogen, amino, formyl, methyl, ethyl, n-propyl, isopropyl, n-butyl, sec-butyl, isobutyl, tert-butyl, vinyl, allyl, propargyl, methoxy, methoxymethyl, —COMe, —COEt, tert-butoxycarbonyl, or oxamoyl; or $R^4$ and $R^5$ together represent ethylidene, isopropylidene, sec-butylidene, benzylidene, or nitrobenzylidene; or $R^4$ and $R^5$ together with the nitrogen atom to which they are attached represent a 5- or 6-membered saturated heterocycle selected from the group consisting of morpholine, piperidine, thiomorpholine, and pyrrolidine, each of which is optionally mono- or disubstituted by identical or different substituents selected from the group consisting of methyl, ethyl, n-propyl, isopropyl, n-butyl, sec-butyl, isobutyl, and tert-butyl;

$R^9$ represents hydrogen, methyl, ethyl, n-propyl, isopropyl, n-butyl, sec-butyl, isobutyl, tert-butyl, —$CH_2CF_3$, —$CH_2CF_2H$, —$CH_2CF_2CF_3$, cyclopropyl, cyclopentyl, or cyclohexyl;

$R^{10}$ represents fluorine, chlorine, bromine, methyl, ethyl, n-propyl, isopropyl, n-butyl, sec-butyl, isobutyl, tert-butyl, —COMe, —COEt, —$CO_2Me$, —$CO_2Et$, or cyclohexyl; or represents phenyl or benzyl that are optionally mono- to tetrasubstituted in the aryl moiety by identical or different substituents selected from the group consisting of fluorine, chlorine, bromine, and methyl;

$R^{14}$ represents hydrogen, methyl, ethyl, n-propyl, isopropyl, n-butyl, sec-butyl, isobutyl, tert-butyl, —$CH_2CF_3$, —$CH_2CF_2H$, or —$CH_2CF_2CF_3$;

$R^{16}$ represents hydrogen; represents $C_1$-$C_{12}$-halogenoalkyl having 1 to 23 fluorine, chlorine, and/or bromine atoms, $C_2$-$C_{10}$-halogenoalkenyl having 1 to 17 fluorine, chlorine, and/or bromine atoms, $C_2$-$C_6$-halogenoalkynyl having 1 to 7 fluorine, chlorine, and/or bromine atoms; represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethynyl, propargyl, or butynyl, each of which is optionally mono- to trisubstituted by identical or different radicals selected from the group consisting of fluorine, chlorine, bromine, amino, hydroxyl, cyano, nitro, methoxy, ethoxy, isopropoxy, trifluoromethoxy, —$OCH_2CF_3$, trichloromethoxy, difluoromethoxy, methylthio, trifluoromethylthio, methoxycarbonyl, ethoxycarbonyl, isopropoxycarbonyl, tert-butoxycarbonyl, methylcarbonyloxy, —O—$(CH_2)_2$—O—, phenoxy, fluorophenoxy, —$CONR^4R^5$, —$NR^4R^5$, —$ONR^4R^5$, and —CH=N—$OCH_3$; or represents phenyl, benzyl, cyclopropyl, cyclopropylmethyl, cyclobutyl, cyclobutylmethyl, cyclopentyl, cyclopentylmethyl, cyclohexyl, cyclohexylmethyl, furyl, thienyl, oxazolyl, imidazyl, pyrazyl, thiazolyl, pyridinyl, pyrimidinyl, pyridazyl, or tetrahydropyranyl, each of which is optionally mono- to trisubstituted by identical or different substituents selected from the group consisting of fluorine, chlorine, bromine, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_2H$, —$CF_2CHFCF_3$, —$CF_2CF_2H$, —$CH_2CF_2CF_3$, —$CH_2CF_3$, methoxy, ethoxy, n-propoxy, n-butoxy, trifluoromethoxy, trichloromethoxy, methylthio, trifluoromethylthio, —$CO_2Me$, —$CO_2Et$, methylcarbonyloxy, and ethylcarbonyloxy;

$R^{17}$ represents hydrogen, methyl, or ethyl; and $R^{18}$ represents hydrogen, hydroxyl, amino, —$SO_2Me$, —$SO_2Et$, methyl, ethyl, n-propyl, isopropyl, n-butyl, sec-butyl, isobutyl, tert-butyl, or allyl; or represents phenyl, benzyl, phenylethyl, cyclopropyl, cyclopropylmethyl, cyclohexyl, pyridinyl, pyridinylmethyl, pyridinylethyl, furyl, or furfuryl, each of which is optionally mono- to trisubstituted by identical or different radicals selected from the group consisting of fluorine, chlorine, hydroxyl, methyl, ethyl, n-propyl, isopropyl, n-butyl, sec-butyl, isobutyl, tert-butyl, trifluoromethyl, trichloromethyl, methoxy, ethoxy, trifluoromethoxy, methylthio, trifluoromethylthio, and —O—$CH_2$—O—; or v$R^{17}$ and $R^{18}$ together with the nitrogen atom to which they are attached represent a 5- or 6-membered saturated heterocycle selected from the group consisting of piperazine, morpholine, piperidine, and pyrrolidine, each of which is optionally mono- to trisubstituted by identical or different substituents selected from the group consisting of methyl, ethyl, n-propyl, and isopropyl; except for the compound 2-{[4-(3,5-dimethyl-1H-pyrazol-1-yl)-2-pyrimidinyl]thio}-acetamide.

38. A method according to claim 37 wherein R represents a carboxylic acid bioisostere selected from the group consisting of

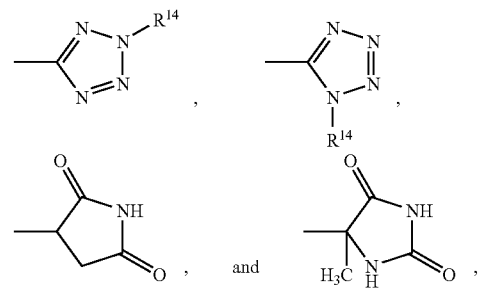

where $R^{14}$ represents hydrogen, alkyl, or halogenoalkyl.

39. A method according to claim 24 wherein the pyrazolylpyrimidine is a compound of formula (I-m)

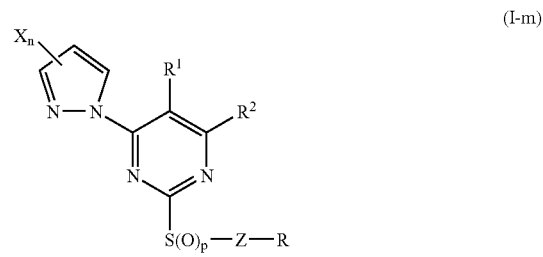

(I-m)

in which $R^1$, $R^2$, X, n, p, Z, and R have the meanings given in claim 24 for formula (I).

40. A method according to claim 24 wherein the pyrazolylpyrimidine is a compound of formula (I-n)

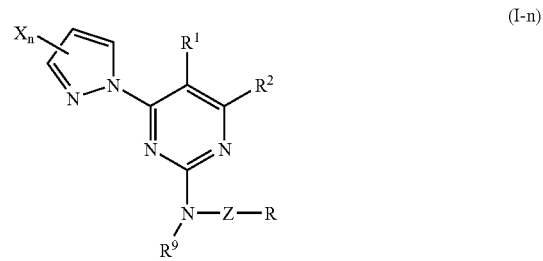

(I-n)

in which $R^1$, $R^2$, X, n, Z, R, and $R^9$ have the meanings given in claim 24 for formula (I).

41. A method according to claim 24 wherein the pyrazolylpyrimidine is a compound of formula (I-o)

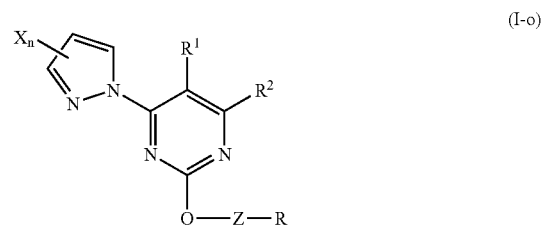

(I-o)

in which $R^1$, $R^2$, X, n, Z, and R have the meanings given in claim 24 for formula (I).

42. A method according to claim 24 wherein the pyrazolylpyrimidine is a compound of formula (I-p)

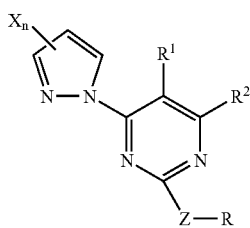

(I-p)

in which $R^1$, $R^2$, X, n, Z and R have the meanings given in claim 24 for formula (I).

43. A method according to claim 24 wherein the pyrazolylpyrimidine is a compound of formula (I-q)

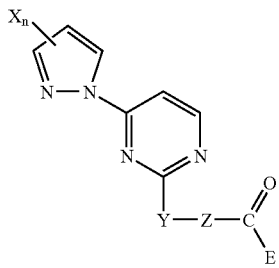

(I-q)

in which

X represents fluorine, chlorine, bromine, nitro, cyano, hydroxyl, methyl, ethyl, trifluoromethyl, methoxy, ethoxy, isopropoxy, trifluoromethoxy, trifluoromethylthio, vinyl, ethynyl, —SO$_2$Me, —NH$_2$, —NHMe, —NMe$_2$, or —COMe; or represents furyl, phenyl, or chlorophenyl; or, when n represents 2 or 3, two adjacent radicals X together optionally represent butylene or butadienylene, n represents 0, 1, 2, or 3, where X represents identical or different radicals when n represents 2 or 3, Y represents —S— or —NR$^9$—, Z represents —CH$_2$— or —(CH$_2$)$_2$—, E represents hydroxyl, methoxy, ethoxy, n-propoxy, isopropoxy, n-butoxy, isobutoxy, sec-butoxy, tert-butoxy, —NH—SO$_2$Me, —NH—SO$_2$Et, —OCH$_2$CHF$_2$, —OCH$_2$CF$_3$, —OCH$_2$CF$_2$CHF$_2$, —OCH$_2$(CF$_2$)$_2$CHF$_2$, —OCH(CF$_3$)$_2$, —OCH(CH$_3$)CF$_3$, —O(CH$_2$)$_2$CF$_3$, —OCH$_2$CH$_2$Cl, —OCH$_2$CHCl$_2$, or —OCH$_2$CCl$_3$, and R$^9$ represents hydrogen, methyl, ethyl, n-propyl, —CH$_2$CF$_3$, —CH$_2$CF$_2$CF$_3$, or cyclopropyl.

* * * * *